United States Patent
Honda et al.

(10) Patent No.: US 8,063,034 B2
(45) Date of Patent: Nov. 22, 2011

(54) OXADIAZOLE DERIVATIVES AND THIADIAZOLE DERIVATIVES HAVING NEOVASCULARIZATION INHIBITORY ACTIVITY

(75) Inventors: Takahiro Honda, Ikoma (JP); Koushi Fujisawa, Ikoma (JP); Hiroyuki Aono, Ikoma (JP); Masakazu Ban, Ikoma (JP)

(73) Assignee: Santen Pharmaceutical Co., Ltd., Osaka-Shi, Osaka (JP)

( * ) Notice: Subject to any disclaimer, the term of this patent is extended or adjusted under 35 U.S.C. 154(b) by 131 days.

(21) Appl. No.: 12/449,159

(22) PCT Filed: Jan. 29, 2008

(86) PCT No.: PCT/JP2008/051312
§ 371 (c)(1),
(2), (4) Date: Jul. 23, 2009

(87) PCT Pub. No.: WO2008/093677
PCT Pub. Date: Aug. 7, 2008

(65) Prior Publication Data
US 2010/0016354 A1    Jan. 21, 2010

(30) Foreign Application Priority Data

Jan. 29, 2007  (JP) ................................. 2007-018059
Mar. 28, 2007  (JP) ................................. 2007-083153

(51) Int. Cl.
*A61K 31/397* (2006.01)
*A61K 31/4245* (2006.01)
*C07D 271/07* (2006.01)
*C07D 413/08* (2006.01)

(52) U.S. Cl. ............ 514/210.2; 514/326; 514/364; 546/209; 548/131

(58) Field of Classification Search .......... 548/131, 548/134; 514/210.2, 326, 364; 546/209
See application file for complete search history.

(56) References Cited

U.S. PATENT DOCUMENTS

| | | |
|---|---|---|
| 7,534,802 B2 | 5/2009 | Honda et al. |
| 2002/0127605 A1 | 9/2002 | Hamilton et al. |
| 2005/0065118 A1 | 3/2005 | Wang et al. |
| 2006/0194836 A1 | 8/2006 | Honda et al. |
| 2007/0185133 A1 | 8/2007 | Smith et al. |

FOREIGN PATENT DOCUMENTS

| | | |
|---|---|---|
| WO | WO 97/30035 A1 | 8/1997 |
| WO | WO 98/35958 A1 | 8/1998 |
| WO | WO 98/50356 A1 | 11/1998 |
| WO | WO 00/27819 A2 | 5/2000 |
| WO | WO 01/55114 A1 | 8/2001 |
| WO | WO 2004/052280 A2 | 6/2004 |
| WO | WO 2005/004818 A2 | 1/2005 |

OTHER PUBLICATIONS

Patani et al, Chem. Rev., 1996, 96(8), pp. 3147-3176, esp. p. 3158.*
Zarghi, et al., Chem. Pharm. Bull., 56(4), 2008, 509-512, esp. p. 510.*
Ouyang et al, Bioorg. & Med. Chem. Lett., vol. 16, 2006, pp. 1191-1196.*
Ouyang, et al., Bioorg. Med. Chem. Lett., vol. 16, 2206, pp. 1191-1196.*
N. Shoten, "Molecular Mechanism of Symptom and Pathology", *Molecular Medicine*, vol. 35, Extra Edition, pp. 73-74 (1998) (with English translation of relevant portion).
K. Shuppan, "Forefront Drug Development", *Extra Edition of Protein, Nucleic Acid, and Enzyme*, pp. 1182-1187 (2000) (with English translation of relevant portion).
A.S. Kiselyov et al, "Hetaryl imidazoles: A novel dual inhibitors of VEGF receptors I and II", *Biorganic & Medicinal Chemistry Letters*, 16, pp. 1440-1444 (2006).
A.S. Kiselyov et al, "Inhibitors of VEGF receptors-1 and -2 based on the 2-((pyridin-4-yl))ethyl)pyridine template", *Biorganic & Medicinal Chemistry Letters*, 16, pp. 1913-1919 (2006).
X. Ouyang et al, "Oxadiazole derivatives as a novel class of antimitotic agents: Synthesis, inhibition of tubulin of polymerization . . . ", *Biorganic & Medicinal Chemistry Letters*, 16, pp. 1191-1196 (2006).
Wermuth C.G, "Molecular Variations Based on Isosteric Replacements," *Practice of Medicinal Chemistry*, XX, XX, Jan. 1, 1996, pp. 203 to 237.
Supplementary European Search Report dated Apr. 1, 2011 for EP 08 70 4094.

* cited by examiner

*Primary Examiner* — Susannah Chung
(74) *Attorney, Agent, or Firm* — Holtz, Holtz, Goodman & Chick, PC

(57) ABSTRACT

The present invention relates to Compounds represented by the formula (I) or salts thereof. In the formula (I), the ring A represents a benzene ring, a thiophene ring, or a pyridine ring; $R_a$ represents a hydrogen atom, a halogen atom, an alkyl group, or an alkoxy group; the ring B represents a pyridine ring, a pyrimidine ring, or a quinoline ring; the ring C represents a benzene ring; a pyridine ring, a quinoline ring, or an isoquinoline ring; X and Y, the same or different, represent an oxygen atom or a sulfur atom, with the proviso that the case X is a sulfur atom and Y is an oxygen atom be excluded; $R_1$ represents a hydrogen atom, a halogen atom, an amino group, a cycloalkylamino group, an alkylcarbonylamino group, an alkyloxycarbonylamino group, an alkylaminocarbonyl group, or a non-aromatic heterocyclic group; and $R_2$ and $R_2'$, the same or different, represent a hydrogen atom, a halogen atom, an alkyl group, a halogeno-alkyl group, or a halogeno-alkoxy group.

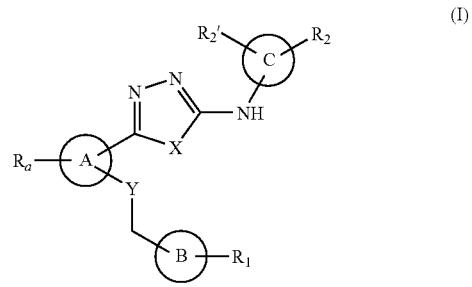

6 Claims, No Drawings

OXADIAZOLE DERIVATIVES AND THIADIAZOLE DERIVATIVES HAVING NEOVASCULARIZATION INHIBITORY ACTIVITY

This application is the United States national phase application of International Application PCT/JP2008/051312 filed Jan. 29, 2008.

TECHNICAL FIELD

The present invention relates to a novel compound having an oxadiazole ring or a thiadiazole ring or a salt thereof useful as a pharmaceutical. These compounds are useful as therapeutic agents for diseases associated with neovascularization, particularly, as therapeutic agents for cancer, rheumatoid arthritis, age-related macular degeneration, diabetic retinopathy, retinopathy of prematurity, retinal vein occlusion, polypoidal choroidal vasculopathy, diabetic macular edema, plaque psoriasis, atherosclerosis, and the like.

BACKGROUND ART

Neovascularization is a phenomenon in which a new blood vessel network is formed from an existing vessel, which is predominantly observed in microvessels. Neovascularization is a physiological phenomena and essential for angiogenesis during the embryonic stage but is not observed in adults except for limited sites such as endometrium and follicle and limited periods such as a course of healing of wounds. However, pathologic neovascularization is observed in diseases such as cancer, rheumatoid arthritis, age-related macular degeneration, diabetic retinopathy, retinopathy of prematurity, retinal vein occlusion, polypoidal choroidal vasculopathy, diabetic macular edema, plaque psoriasis, and atherosclerosis and is associated closely with pathologic progress of each of the diseases. The neovascularization is regulated by a balance between a promoting factor and a suppressing factor, and it is considered that the neovascularization occurs due to disruption of the balance (see Non-Patent Publication 1 and Non-Patent Publication 2).

The vascular endothelial growth factor (hereinafter, referred to as "VEGF") is a factor that promotes construction of a capillary vessel network by way of proliferation, migration, and tube formation of vascular endothelial cells by specifically acting on receptors (Flt-1, KDR/Flk-1, etc.) existing on a surface of vascular endothelial cells and has a remarkably important role in occurrence of neovascularization. Therefore, many trials for treating the diseases associated with neovascularization by controlling occurrence of neovascularization through inhibition of VEGF have been reported. Examples of drugs to be used for such treatment include indolin-2-one derivatives (see Patent Publication 1), phthalazine derivatives (see Patent Publication 2), quinazoline derivatives (see Patent Publication 3), anthranilamide derivatives (see Patent Publication 4), the 2-aminonicotinic acid derivatives (see Patent Publication 5), 4-pyridylalkylthio derivatives (see Patent Publication 6), and the like.

Meanwhile, since compounds having an oxadiazole ring or a thiadiazole ring exhibit useful bioactivity, applications of the compounds to many pharmaceutical products and the like have been tried. Among the applications, each of the oxadiazole derivatives reported in Patent Publication 7 and Non-Patent Publications 3 and 4 is proved to have neovascularization inhibitory activity by way of the inhibition of VEGF receptor tyrosine kinase. Each of the compounds disclosed in the publications is characterized by having a 4-pyridylalkylamino group or a 4-pyridylethyl group. However, synthesis and neovascularization inhibitory activity of the compounds having the 4-pyridylalkyloxy group, 4-pyridylalkylthio group, or the like are not disclosed at all.

Non-Patent Publication 1: Molecular Medicine, vol. 35, Extra Edition, "Molecular Mechanism of Symptom and Pathology", Nakayama Shoten, 73-74 (1998)

Non-Patent Publication 2: Extra Edition of Protein, Nucleic Acid, and Enzyme, "Forefront Drug Development", Kyoritsu Shuppan, 118, 2-1187 (2000)

Non-Patent Publication 3: Bioorg, Med. Chem. Lett., 16 (5), 1440-1444 (2006)

Non-Patent Publication 4: Bioorg, Med. Chem. Lett., 16 (7), 1913-1919 (2006)

Patent Publication 1: International Publication WO98/50356

Patent Publication 2: International Publication WO98/35958

Patent Publication 3: International Publication WO97/30035

Patent Publication 4: International Publication WO00/27819

Patent Publication 5: International Publication WO01/55114

Patent Publication 6: International Publication WO04/078723

Patent Publication 7: International Publication WO04/052280

DISCLOSURE OF THE INVENTION

Problems to be Solved

It is a very interesting object to study on syntheses of novel oxadiazole derivatives and thiadiazole derivatives each having a 4-pyridylalkyloxy group or a 4-pyridylalkylthio group as well as to find pharmacological actions of the compounds.

Means for Solving the Problems

The present inventors made the studies of the synthesis of novel oxadiazole derivatives and thiadiazole derivatives each having a 4-pyridylalkyloxy group or a 4-pyridylalkylthio group and succeeded in creating a large number of novel compounds.

Further, as a result of various studies on pharmacological actions of the compounds, the inventors found that the compounds have a neovascularization inhibitory action and are useful as therapeutic agents for diseases associated with neovascularization, particularly, as therapeutic agents for cancer, rheumatoid arthritis, age-related macular degeneration, diabetic retinopathy, retinopathy of prematurity, retinal vein occlusion, polypoidal choroidal vasculopathy, diabetic macular edema, plaque psoriasis, atherosclerosis, and the like, thereby accomplished the present invention.

Specifically, the present invention relates to a compound represented by the general formula (I) or a salt thereof (hereinafter referred to as "the present compound" unless otherwise noted) and a pharmaceutical composition comprising the present compound. As more detailed description of pharmaceutical application of the present compound, the present invention relates to a therapeutic agent comprising the present compound as an active ingredient and used for a disease associated with neovascularization, such as a therapeutic agent for cancer, rheumatoid arthritis, age-related macular degeneration, diabetic retinopathy, retinopathy of prematurity, retinal vein occlusion, polypoidal choroidal vasculopa thy, diabetic macular edema, plaque psoriasis, atherosclerosis, or the like:

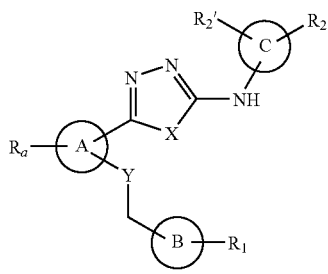

(I)

[wherein, the ring A represents a benzene ring, a thiophene ring, or a pyridine ring;

$R_a$ represents a hydrogen atom, a halogen atom, an alkyl group, or an alkoxy group;

the ring B represents a pyridine ring, a pyrimidine ring, or a quinoline ring;

the ring C represents a benzene ring, a pyridine ring, a quinoline ring, or an isoquinoline ring;

X and Y, the same or different, represent an oxygen atom or a sulfur atom, with the proviso that the case X is a sulfur atom and Y is an oxygen atom be excluded;

$R_1$ represents a hydrogen atom, a halogen atom, an amino group, a cycloalkylamino group, an alkylcarbonylamino group, an alkyloxycarbonylamino group, an alkylaminocarbonyl group, or a non-aromatic heterocyclic group;

$R_2$ and $R_2'$, the same or different, represent a hydrogen atom, a halogen atom, an alkyl group, a halogeno-alkyl group, or a halogeno-alkoxy group].

Advantageous Effect of the Invention

The present invention provides novel oxadiazole derivatives and thiadiazole derivatives having a 4-pyridylalkyloxy group, a 4-pyridylalkylthio group or the like or a salt thereof useful as a pharmaceutical. The novel cyclic compounds according to the present invention have an excellent neovascularization inhibitory action and are useful as therapeutic agents for diseases associated with neovascularization, such as therapeutic agents for cancer, rheumatoid arthritis, age-related macular degeneration, diabetic retinopathy, retinopathy of prematurity, retinal vein occlusion, polypoidal choroidal vasculopathy, diabetic macular edema, plaque psoriasis, atherosclerosis, and the like.

Also, the present compounds have been confirmed to have a tyrosine kinase (KDR) inhibitory action that is apparently excellent as compared to compounds wherein the X atom and the Y atom in the compounds represented by the general formula (I) are a sulfur atom and an oxygen atom, respectively. In other words, the present compounds have apparently excellent neovascularization inhibitory action as compared to the compounds having the similar structure.

The present compounds have been confirmed to have the apparently excellent neovascularization inhibitory action.

BEST MODE FOR CARRYING OUT THE INVENTION

Each of groups used in claims and the specification has the following meaning throughout the claims and the specification.

The term "halogen atom" means fluorine, chlorine, bromine, or iodine.

The term "alkyl" means straight-chain or branched alkyl having 1 to 6 carbon atoms. Specific examples thereof include methyl, ethyl, n-propyl, n-butyl, n-pentyl, n-hexyl, isopropyl, isobutyl, sec-butyl, tert-butyl, isopentyl, and the like.

The term "cycloalkyl" means cycloalkyl having 3 to 8 carbon atoms. Specific examples thereof include cyclopropyl, cyclobutyl, cyclopentyl, cyclohexyl, cycloheptyl, cyclooctyl, and the like.

The term "alkoxy" means straight-chain or branched alkoxy having 1 to 6 carbon atoms. Specific examples thereof include methoxy, ethoxy, n-propoxy, n-butoxy, n-pentyloxy, n-hexyloxy, isopropoxy, isobutoxy, sec-butoxy, tert-butoxy, isopentyloxy, and the like.

The term "non-aromatic heterocyclic ring" means a monocyclic non-aromatic heterocyclic ring or a bicyclic or tricyclic condensed polycyclic non-aromatic heterocyclic ring having one or a plurality of heteroatoms (nitrogen atom, oxygen atom, sulfur atom) in the ring.

Specific examples of the monocyclic non-aromatic heterocyclic ring include a saturated non-aromatic heterocyclic ring having one heteroatom in the ring, such as pyrrolidine, tetrahydrofuran, tetrahydrothiophene, piperidine, tetrahydropyran, and homopiperazine; a saturated non-aromatic heterocyclic ring having two heteroatoms in the ring, such as imidazolidine, oxazolidine, thiazolidine, pyrazolidine, piperazine, morpholine, thiomorpholine, homopiperidine, and homomorpholine; an unsaturated non-aromatic heterocyclic ring having one heteroatom in the ring, such as pyrroline, dihydrofuran, dihydrothiophene, tetrahydropyridine, dihydropyridine, dihydropyran, and pyran; and an unsaturated non-aromatic heterocyclic ring having two heteroatoms, such as imidazoline, oxazoline, thiazoline, and pyrazoline, and specific examples of the bicyclic or tricyclic condensed polycyclic non-aromatic heterocyclic ring include chromane, indoline, isoindoline, xanthine, and the like.

The term "cycloalkylamino" means monocycloalkylamino having 3 to 8 carbon atoms or dicycloalkylamino having 6 to 16 carbon atoms. Specific examples of monoalkylamino include cyclopropylamino, cyclobutylamino, cyclohexylamino, and the like, and specific examples of dicycloalkylamino include dicyclopropylamino, dicyclobutylamino, dicyclohexylamino, and the like.

The term "alkylcarbonyl" means straight-chain or branched alkylcarbonyl having 2 to 7 carbon atoms. Specific examples thereof include methylcarbonyl, ethylcarbonyl, n-propylcarbonyl, n-butylcarbonyl, n-pentylcarbonyl, n-hexylcarbonyl, isopropylcarbonyl, isobutylcarbonyl, sec-butylcarbonyl, tert-butylcarbonyl, isopentylcarbonyl, and the like.

The term "alkyloxycarbonyl" means straight-chain or branched alkyloxycarbonyl having 2 to 7 carbon atoms. Specific examples thereof include methoxycarbonyl, ethoxycarbonyl, n-propoxycarbonyl, n-butoxycarbonyl, n-pentyloxycarbonyl, n-hexyloxycarbonyl, isopropoxycarbonyl, isobutoxycarbonyl, sec-butoxycarbonyl, tert-butoxycarbonyl, isopentyloxycarbonyl, and the like.

The term "alkylcarbonylamino" means amino having one alkylcarbonyl or a plurality of, the same or different, alkylcarbonyls as a substituent or substituents.

The term "alkyloxycarbonylamino" means amino having one alkyloxycarbonyl or a plurality of, the same or different, alkyloxycarbonyls as a substituent or substituents.

The term "alkylaminocarbonyl" means monoalkylaminocarbonyl having 2 to 7 carbon atoms or dialkylaminocarbonyl having 3 to 13 carbon atoms. Specific examples of monoalkylaminocarbonyl include methylaminocarbonyl, ethylaminocarbonyl, propylaminocarbonyl, butylaminocarbonyl, hexylaminocarbonyl, and the like, and specific examples of dialkylaminocarbonyl include dimethylaminocarbonyl, diethylaminocarbonyl, dipropylaminocarbonyl, dibutylaminocarbonyl, dihexylaminocarbonyl, ethylmethylaminocarbonyl, and the like.

The term "halogeno-alkyl" means alkyl having one halogen atom or a plurality of, the same or different, halogen atoms as a substituent or substituents.

The term "halogeno-alkoxy" means alkoxy having one halogen atom or a plurality of, the same or different, halogen atoms as a substituent or substituents.

In the case where the present compound has a free amino group, a free cycloalkylamino group, an free alkylcarbonylamino group, an free alkyloxycarbonylamino group, or an free alkylaminocarbonyl group as a substituent, the substituent may be protected by a protective group. Also, in the case where the non-aromatic heterocyclic ring has a free nitrogen atom, the nitrogen atom may be protected by a protective group.

The term "a protective group of a free amino group, a free cycloalkylamino group, a free alkylcarbonylamino group, a free alkyloxycarbonylamino group, a free alkylaminocarbonyl group, or a free nitrogen atom of a non-aromatic heterocyclic group" means that widely used as a protective group of a free amino group, a free cycloalkylamino group, a free alkylcarbonylamino group, a free alkyloxycarbonylamino group, or a free nitrogen atom of a non-aromatic heterocyclic group, such as a non-substituted alkenyl group such as an aryl group; a hydrocarbonyl group such as a formyl group; a substituted or non-substituted alkylcarbonyl group, a substituted or non-substituted arylcarbonyl group, or a non-substituted aromatic heterocyclic carbonyl group such as an acetyl group, a trichloroacetyl group, a trifluoroacetyl group, a benzoyl group, a 4-chlorobenzoyl group, or a picolinoyl group; a substituted or non-substituted alkyloxycarbonyl or a substituted or non-substituted aryloxycarbonyl group such as a methoxycarbonyl group, an isobutoxycarbonyl group, a tert-butoxycarbonyl group, a 2,2,2-trichloroethoxycarbonyl group, a benzyloxycarbonyl group, a diphenylmethoxycarbonyl group, a phenoxycarbonyl group, or a m-nitrophenoxycarbonyl group; and a substituted or non-substituted alkylsulfonyl group or a substituted or non-substituted arylsulfonyl group such as a methylsulfonyl group, a benzylsulfonyl group, a phenylsulfonyl group, a 4-chlorophenylsulfonyl group, a tolylsulfonyl group, or a 2,4,6-trimethylphenylsulfonyl group.

Each of the substituted alkyl group, substituted alkylcarbonyl group, substituted arylcarbonyl group, substituted alkyloxycarbonyl group, substituted aryloxycarbonyl group, substituted alkylsulfonyl group, or substituted arylsulfonyl group means an alkyl group, an alkylcarbonyl group, an arylcarbonyl group, an alkyloxycarbonyl group, an aryloxycarbonyl group, an alkylsulfonyl group, or an arylsulfonyl group that is substituted by one or a plurality of groups selected from a halogen atom, an alkoxy group, an alkyl group, an aryl group, a halogeno-aryl group, an alkoxyaryl group, and a nitro group.

The term "plurality of groups" used in the present invention means preferably two or three groups, more preferably two groups which may be the same or different.

The term "group" used in the present invention includes a hydrogen atom, a halogen atom, and an oxo ligand.

The term "salt" of the present compounds is not particularly limited insofar as the salt is pharmaceutically acceptable and includes a salt with an inorganic acid such as hydrochloric acid, hydrobromic acid, hydroiodic acid, nitric acid, sulfuric acid, or phosphoric acid, a salt with an organic acid such as acetic acid, fumaric acid, maleic acid, succinic acid, citric acid, tartaric acid, adipic acid, gluconic acid, glucoheptic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid, or sulfosalicylic acid, a quaternary ammonium salts with methyl bromide, methyl iodide, or the like, a salt with a halogen ion such as a bromine ion, a chlorine ion, or an iodine ion, a salt with an alkali metal such as lithium, sodium, or potassium, a salt with an alkaline earth metal such as calcium or magnesium, a salt with a metal such as iron, zinc, or the like, a salt with ammonia, a salt with an organic amine such as triethylenediamine, 2-aminoethanol, or 2,2-iminobis (ethanol), 1-deoxy-1-(methylamino)-2-D-sorbitol, 2-amino-2-(hydroxymethyl)-1,3-propanediol, procaine, or N,N-bis(phenylmethyl)-1,2-ethanediamine, and the like.

In the case where a geometrical isomer or an optical isomer is present in the present compounds, such isomers are included within the scope of the present invention.

The present compound may be in the form of a hydrate and/or a solvate.

In the case where a proton tautomerism is present in the present compounds, such proton tautomers are included in the present invention.

(a) Preferred examples of the present compound include compounds in which the respective groups are as defined below or in the compounds represented by the general formula (I') or salts thereof:

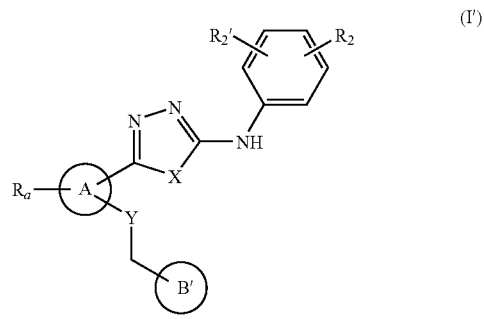

(a1) the ring A represents

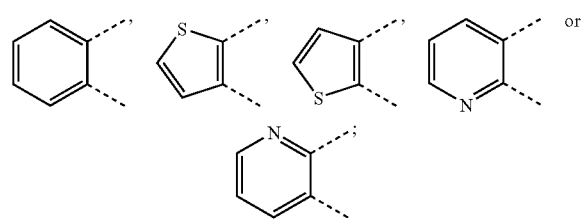

and/or (a2) $R_a$ represents a hydrogen atom, a halogen atom, an alkyl group, or an alkoxy group; and/or (a3) the ring B' represents

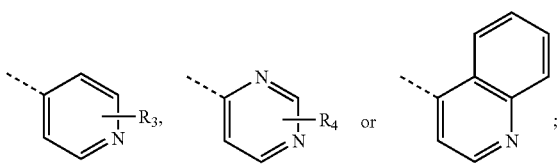

and/or
(a4) X and Y, the same or different, represent an oxygen atom or a sulfur atom, with the proviso that the case X is a sulfur atom and Y is an oxygen atom be excluded; and/or
(a5) $R_2$ and $R_2'$, the same or different, represent a hydrogen atom, a halogen atom, an alkyl group, a halogeno-alkyl group, or a halogeno-alkoxy group; and/or
(a6) $R_3$ represents a hydrogen atom, a halogen atom, an amino group, a cycloalkylamino group, an alkylcarbonylamino group, an alkyloxycarbonylamino group, an alkylaminocarbonyl group, or a non-aromatic heterocyclic group; and/or
(a7) $R_4$ represents a hydrogen atom, a halogen atom, an amino group, a cycloalkylamino group, an alkylcarbonylamino group, an alkyloxycarbonylamino group, an alkylaminocarbonyl group, or a non-aromatic heterocyclic group.

That is, in the compounds represented by the general formula (I'), preferred examples include compounds which comprise one or a combination of two or more selected from the above (a1), (a2), (a3), (a4), (a5), (a6), and (a7) or salts thereof.

(b) More preferred examples in the present compounds include a compound represented by the general formula (I') defined in (a) or the salt thereof in which the groups are as described below.

(b1) the ring A represents

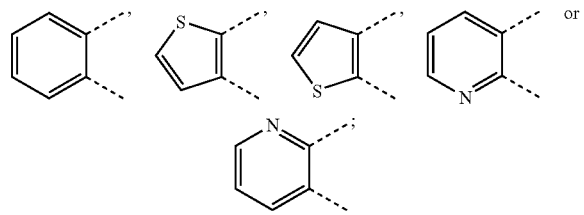

and/or
(b2) $R_a$ represents a hydrogen atom, a halogen atom, or an alkoxy group; and/or
[b3] the ring B' represents

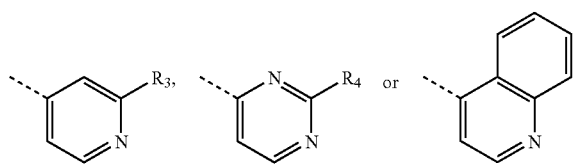

and/or
(b4) X and Y, the same or different, represent an oxygen atom or a sulfur atom, with the proviso that the case X is a sulfur atom and Y is an oxygen atom be excluded; and/or
(b5) $R_2$ and $R_2'$, the same or different, represent a hydrogen atom, a halogen atom, an alkyl group, a halogeno-alkyl group, or a halogeno-alkoxy group; and/or (b6) $R_3$ represents a hydrogen atom, a halogen atom, an amino group, a cycloalkylamino group, an alkylcarbonylamino group, an alkyloxycarbonylamino group, an alkylaminocarbonyl group, or a non-aromatic heterocyclic group; and/or
(b7) $R_4$ represents a hydrogen atom or an amino group.

That is, in the compounds represented by the general formula (I') defined in (a), more preferred examples include compounds which comprise one or a combination of two or more selected from the above (b1), (b2), (b3), (b4), (b5), (b6), and (b7) or salts thereof.

(c) More preferred examples in the present compounds include a compound represented by the general formula (I') defined in (b) or the salt thereof in which the groups are as described below.

(c1) the ring A represents

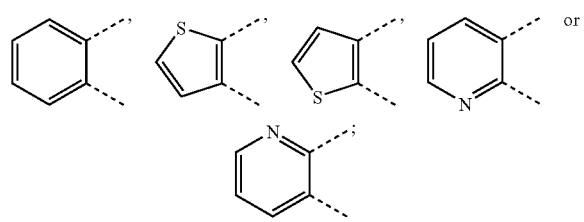

and/or
(c2) $R_a$ represents a hydrogen atom, a bromine atom, or a methoxy group; and/or
[c3] the ring B' represents

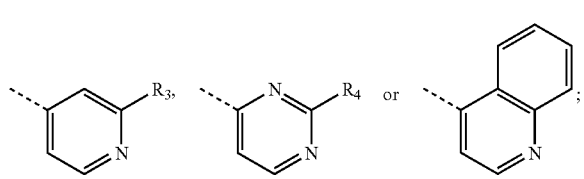

and/or
(c4) X and Y, the same or different, represent an oxygen atom or a sulfur atom, with the proviso that the case X is a sulfur atom and Y is an oxygen atom be excluded; and/or
(c5) $R_2$ and $R_2'$, the same or different, represent a hydrogen atom, a bromine atom, tert-butyl group, a trifluoromethyl group, or a trifluoromethoxy group; and/or
(c6) $R_3$ represents a hydrogen atom, a fluorine atom, an amino group, a cyclopropylamino group, a methylcarbonylamino group, a tert-butoxycarbonylamino group, a methylaminocarbonyl group, or a morpholin-4-yl group; and/or
(c7) $R_4$ represents a hydrogen atom or an amino group.

That is, in the compounds represented by the general formula (I') defined in (b), more preferred examples include compounds which comprise one or a combination of two or more selected from the above (c1), (c2), (c3), (c4), (c5), (c6), and (c7) or salts thereof.

(d) Specific examples of particularly preferred compounds or salts thereof in the present compounds are as follows.
N-phenyl-5-(2-(pyridin-4-yl)methoxyphenyl)-1,3,4-oxadiazol-2-amine,
N-(4-chlorophenyl)-5-(2-(pyridin-4-yl)methoxyphenyl)-1, 3,4-oxadiazol-2-amine,
5-(2-(pyridin-4-yl)methoxyphenyl)-N-(3-trifluoromethylphenyl)-1,3,4-oxadiazol-2-amine, N-phenyl-5-(2-(quinolin-4-yl)methoxyphenyl)-1,3,4-oxadiazol-2-amine,
N-phenyl-5-(3-(pyridin-4-yl)methoxythiophen-2-yl)-1,3,4-oxadiazol-2-amine,
5-(2-(2-acetamidopyridin-4-yl)methoxyphenyl)-N-phenyl-1,3,4-oxadiazol-2-amine,
5-(2-(2-t-butoxycarbonylaminopyridin-4-yl)methylthiopyridin-3-yl)-N-phenyl-1,3,4-oxadiazol-2-amine,
5-(2-(quinolin-4-yl)methoxyphenyl)-N-(3-trifluoromethylphenyl)-1,3,4-oxadiazol-2-amine,
5-(2-(2-acetamidopyridin-4-yl)methoxyphenyl)-N-(3-trifluoromethylphenyl)-1,3,4-oxadiazol-2-amine,
N-phenyl-5-(2-(pyridin-4-yl)methylthiophenyl)-1,3,4-oxadiazol-2-amine,
5-(2-(pyridin-4-yl)methylthiophenyl)-N-(3-trifluoromethylphenyl)-1,3,4-oxadiazol-2-amine,
N-(4-t-butylphenyl)-5-(2-(pyridin-4-yl)methylthiophenyl)-1,3,4-oxadiazol-2-amine,
N-phenyl-5-(2-(pyridin-4-yl)methylthiophenyl)-1,3,4-thiadiazol-2-amine,
N-(4-chlorophenyl)-5-(2-(pyridin-4-yl)methylthiophenyl)-1,3,4-thiadiazol-2-amine,
N-(3-chlorophenyl)-5-(2-(pyridin-4-yl)methylthiophenyl)-1,3,4-thiadiazol-2-amine,
5-(2-(pyridin-4-yl)methylthiophenyl)-N-(4-trifluoromethylphenyl)-1,3,4-thiadiazol-2-amine,
N-(4-t-butylphenyl)-5-(2-(pyridin-4-yl)methylthiophenyl)-1,3,4-thiadiazol-2-amine,
N-phenyl-5-(2-(quinolin-4-yl)methylthiophenyl)-1,3,4-oxadiazol-2-amine,
N-(4-chlorophenyl)-5-(2-(pyridin-4-yl)methylthiophenyl)-1,3,4-oxadiazol-2-amine,
N-(4-chlorophenyl)-5-(2-(quinolin-4-yl)methylthiophenyl)-1,3,4-oxadiazol-2-amine,
5-(2-(quinolin-4-yl)methylthiophenyl)-N-(3-trifluoromethylphenyl)-1,3,4-oxadiazol-2-amine,
5-(2-(2-acetamidopyridin-4-yl)methylthiophenyl)-N-phenyl-1,3,4-oxadiazol-2-amine,
5-(2-(2-acetamidopyridin-4-yl)methylthiophenyl)-N-(4-chlorophenyl)-1,3,4-oxadiazol-2-amine,
5-(2-(2-acetamidopyridin-4-yl)methylthiophenyl)-N-(3-trifluoromethylphenyl)-1,3,4-oxadiazol-2-amine,
5-(2-(2-aminopyrimidin-4-yl)methylthiophenyl)-N-phenyl-1,3,4-oxadiazol-2-amine,
5-(2-(2-fluoropyridin-4-yl)methylthiophenyl)-N-phenyl-1,3,4-oxadiazol-2-amine,
N-phenyl-5-(2-(quinolin-4-yl)methylthiophenyl)-1,3,4-thiadiazol-2-amine,
N-(4-chlorophenyl)-5-(2-(quinolin-4-yl)methylthiophenyl)-1,3,4-thiadiazol-2-amine,
N-(3-chlorophenyl)-5-(2-(quinolin-4-yl)methylthiophenyl)-1,3,4-thiadiazol-2-amine,
5-(2-(quinolin-4-yl)methylthiophenyl)-N-(4-trifluoromethylphenyl)-1,3,4-thiadiazol-2-amine,
5-(2-(2-acetamidopyridin-4-yl)methylthiophenyl)-N-phenyl-1,3,4-thiadiazol-2-amine,
5-(2-(2-fluoropyridin-4-yl)methylthiophenyl)-N-phenyl-1,3,4-thiadiazol-2-amine,
5-(2-(2-cyclopropylaminopyridin-4-yl)methylthiophenyl)-N-phenyl-1,3,4-oxadiazol-2-amine,
5-(2-(2-morpholinopyridin-4-yl)methylthiophenyl)-N-phenyl-1,3,4-oxadiazol-2-amine,
5-(2-(2-morpholinopyridin-4-yl)methylthiophenyl)-N-phenyl-1,3,4-thiadiazol-2-amine,
5-(2-(2-t-butoxycarbonylaminopyridin-4-yl)methylthiopyridin-3-yl)-N-(4-chlorophenyl)-1,3,4-oxadiazol-2-amine,
5-(2-(2-t-butoxycarbonylaminopyridin-4-yl)methylthiopyridin-3-yl)-N-(3-trifluoromethylphenyl)-1,3,4-oxadiazol-2-amine,
N-phenyl-5-(2-(pyridin-4-yl)methylthiopyridin-3-yl)-1,3,4-oxadiazol-2-amine,
N-(4-chlorophenyl)-5-(2-(pyridin-4-yl)methylthiopyridin-3-yl)-1,3,4-oxadiazol-2-amine,
5-(2-(pyridin-4-yl)methylthiopyridin-3-yl)-N-(3-trifluoromethylphenyl)-1,3,4-oxadiazol-2-amine,
N-phenyl-5-(2-(quinolin-4-yl)methylthiopyridin-3-yl)-1,3,4-oxadiazol-2-amine,
N-(4-chlorophenyl)-5-(2-(quinolin-4-yl)methylthiopyridin-3-yl)-1,3,4-oxadiazol-2-amine,
5-(2-(quinolin-4-yl)methylthiopyridin-3-yl)-N-(3-trifluoromethylphenyl)-1,3,4-oxadiazol-2-amine,
5-(2-(2-acetamidopyridin-4-yl)methylthiopyridin-3-yl)-N-phenyl-1,3,4-oxadiazol-2-amine,
5-(2-(2-acetamidopyridin-4-yl)methylthiopyridin-3-yl)-N-(4-chlorophenyl)-1,3,4-oxadiazol-2-amine,
5-(2-(2-acetamidopyridin-4-yl)methylthiopyridin-3-yl)-N-(3-trifluoromethylphenyl)-1,3,4-oxadiazol-2-amine,
5-(2-(2-methylaminocarbonylpyridin-4-yl)methylthiopyridin-3-yl)-N-phenyl-1,3,4-oxadiazol-2-amine,
N-(4-chlorophenyl)-5-(2-(2-methylaminocarbonylpyridin-4-yl)methylthiopyridin-3-yl)-1,3,4-oxadiazol-2-amine,
5-(2-(2-methylaminocarbonylpyridin-4-yl)methylthiopyridin-3-yl)-N-(3-trifluoromethylphenyl)-1,3,4-oxadiazol-2-amine,
N-(2-chloro-5-trifluoromethylphenyl)-5-(2-(pyridin-4-yl)methoxyphenyl)-1,3,4-oxadiazol-2-amine,
N-(4-t-butylphenyl)-5-(2-(pyridin-4-yl)methoxyphenyl)-1,3,4-oxadiazol-2-amine,
5-(3-(pyridin-4-yl)methoxythiophen-2-yl)-N-(3-trifluoromethylphenyl)-1,3,4-oxadiazol-2-amine,
5-(2-(2-aminopyridin-4-yl)methylthiopyridin-3-yl)-N-phenyl-1,3,4-oxadiazol-2-amine hydrochloride,
5-(2-(2-aminopyridin-4-yl)methylthiopyridin-3-yl)-N-(4-chlorophenyl)-1,3,4-oxadiazol-2-amine hydrochloride,
5-(2-(2-aminopyridin-4-yl)methylthiopyridin-3-yl)-N-(3-trifluoromethylphenyl)-1,3,4-oxadiazol-2-amine hydrochloride,
5-(5-bromo-2-(pyridin-4-yl)methoxyphenyl)-N-phenyl-1,3,4-oxadiazol-2-amine,
5-(5-methoxy-2-(pyridin-4-yl)methoxyphenyl)-N-phenyl-1,3,4-oxadiazol-2-amine,
N-phenyl-5-(3-(pyridin-4-yl)methoxypyridin-2-yl)-1,3,4-oxadiazol-2-amine,
5-(3-(pyridin-4-yl)methoxypyridin-2-yl)-N-(3-trifluoromethylphenyl)-1,3,4-oxadiazol-2-amine,
5-(2-(2-acetamidopyridin-4-yl)methylthiopyridin-3-yl)-N-(4-trifluoromethoxyphenyl)-1,3,4-oxadiazol-2-amine,
N-(4-(2-(5-phenylamino-1,3,4-oxadiazol-2-yl)thiophen-3-yloxy)methylpyridin-2-yl)acetamide,
N-(4-(2-(5-(3-trifluoromethylphenyl)amino-1,3,4-oxadiazol-2-yl)thiophen-3-yl)oxymethylpyridin-2-yl)acetamide,
5-(2-(2-acetamidopyridin-4-yl)methylthiophenyl)-N-(4-trifluoromethylphenyl)-1,3,4-thiadiazol-2-amine,
5-(2-(2-acetamidopyridin-4-yl)methylthiophenyl)-N-(4-chlorophenyl)-1,3,4-thiadiazol-2-amine,
5-(2-(pyridin-4-yl)methylthiophenyl)-N-(3-trifluoromethylphenyl)-1,3,4-thiadiazol-2-amine,
5-(2-(2-acetamidopyridin-4-yl)methylthiophenyl)-N-(3-trifluoromethylphenyl)-1,3,4-thiadiazol-2-amine,
5-(2-(2-acetamidopyridin-4-yl)methylthiophenyl)-N-(3-chlorolphenyl)-1,3,4-thiadiazol-2-amine, 5-(2-(pyridin-4-yl)methylthiophenyl)-N-(4-trifluoromethoxyphenyl)-1,3,4-oxadiazol-2-amine,
5-(2-(pyridin-4-yl)methylthiophenyl)-N-(4-trifluoromethoxyphenyl)-1,3,4-thiadiazol-2-amine,
5-(2-(2-acetamidopyridin-4-yl)methylthiophenyl)-N-(4-trifluoromethoxyphenyl)-1,3,4-thiadiazol-2-amine,
5-(2-(2-acetamidopyridin-4-yl)methylthiophenyl)-N-(4-trifluoromethoxyphenyl)-1,3,4-oxadiazol-2-amine,
N-phenyl-5-(3-(pyridin-4-yl)methylthiothiophen-2-yl)-1,3,4-oxadiazol-2-amine,
5-(3-(2-acetamidopyridin-4-yl)methylthiothiophen-2-yl)-N-phenyl-1,3,4-oxadiazol-2-amine,
N-phenyl-5-(3-(quinolin-4-yl)methylthiothiophen-2-yl)-1,3,4-oxadiazol-2-amine,
N-phenyl-5-(3-(pyridin-4-yl)methylthiothiophen-2-yl)-1,3,4-thiadiazol-2-amine,
5-(3-(2-acetamidopyridin-4-yl)methylthiothiophen-2-yl)-N-phenyl-1,3,4-thiadiazol-2-amine,
N-phenyl-5-(3-(quinolin-4-yl)methylthiothiophen-2-yl)-1,3,4-thiadiazol-2-amine,
N-(4-chlorophenyl)-5-(3-(pyridin-4-yl)methylthiothiophen-2-yl)-1,3,4-oxadiazol-2-amine,
5-(3-(2-acetamidopyridin-4-yl)methylthiothiophen-2-yl)-N-(4-chlorophenyl)-1,3,4-oxadiazol-2-amine,
N-(4-chlorophenyl)-5-(3-(quinolin-4-yl)methylthiothiophen-2-yl)-1,3,4-oxadiazol-2-amine,
N-(4-chlorophenyl)-5-(3-(pyridin-4-yl)methylthiothiophen-2-yl)-1,3,4-thiadiazol-2-amine,
5-(3-(pyridin-4-yl)methylthiothiophen-2-yl)-N-(4-trifluoromethoxyphenyl)-1,3,4-oxadiazol-2-amine,
5-(3-(2-acetamidopyridin-4-yl)methylthiothiophen-2-yl)-N-(4-trifluoromethoxyphenyl)-1,3,4-oxadiazol-2-amine,
5-(3-(quinolin-4-yl)methylthiothiophen-2-yl)-N-(4-trifluoromethoxyphenyl)-1,3,4-oxadiazol-2-amine,
5-(3-(pyridin-4-yl)methylthiothiophen-2-yl)-N-(3-trifluoromethylphenyl)-1,3,4-oxadiazol-2-amine,
5-(3-(2-acetamidopyridin-4-yl)methylthiothiophen-2-yl)-N-(3-trifluoromethylphenyl)-1,3,4-oxadiazol-2-amine,
5-(3-(quinolin-4-yl)methylthiothiophen-2-yl)-N-(3-trifluoromethylphenyl)-1,3,4-oxadiazol-2-amine,
5-(3-(pyridin-4-yl)methylthiothiophen-2-yl)-N-(3-trifluoromethylphenyl)-1,3,4-thiadiazol-2-amine,
5-(3-(2-acetamidopyridin-4-yl)methylthiothiophen-2-yl)-N-(3-trifluoromethylphenyl)-1,3,4-thiadiazol-2-amine,
N-(4-chlorophenyl)-5-(2-(pyridin-4-yl)methylthiothiophen-3-yl)-1,3,4-oxadiazol-2-amine,
5-(2-(2-acetamidopyridin-4-yl)methylthiothiophen-3-yl)-N-(4-chlorophenyl)-1,3,4-oxadiazol-2-amine,
5-(2-(2-acetamidopyridin-4-yl)methylthiothiophen-3-yl)-N-(3-trifluoromethylphenyl)-1,3,4-oxadiazol-2-amine,
5-(3-(pyridin-4-yl)methylthiothiophen-2-yl)-N-(4-trifluoromethoxylphenyl)-1,3,4-thiadiazol-2-amine, and
5-(3-(2-acetamidopyridin-4-yl)methylthiothiophen-2-yl)-N-(4-trifluoromethoxylphenyl)-1,3,4-thiadiazol-2-amine.

It is possible to produce the present compound by the following three general methods A, B, and C. Specific production methods will be described in detail in [Production Examples] in Examples described later in this specification. The term "$R_{alkyl}$" used in a synthetic route described below represents an alkyl group such as a methyl group and an ethyl group, and the term "Hal" represents a halogen atom such as bromine.

It is possible to synthesize the present compound (I) by the general synthetic route A depending on the types of $R_1$ group and $R_2$ group. Specific methods (A-1 to -7) of the general synthetic route A are described below.

General Synthetic Route A

It is possible to produce the present compound (I) in accordance with the synthetic route A-1. That is, in the case where X is an oxygen atom, it is possible to obtain the compound (I; X=O) by reacting a compound (II; X=O) in an organic solvent such as methylene chloride using triphenylphosphine, carbon tetrachloride and an organic base such as triethylamine at a temperature from room temperature to 100° C. for one hour to 24 hours. Also, in the case where X is a sulfur atom, it is possible to obtain the compound (I; X=S) by reacting a compound (II; X=S) with concentrated sulfuric acid in an organic solvent such as ethanol at a temperature from room temperature to 100° C. for one hour to 24 hours.

Synthetic Route A-1

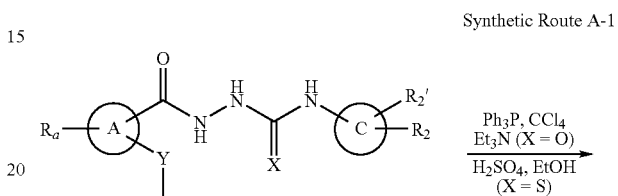

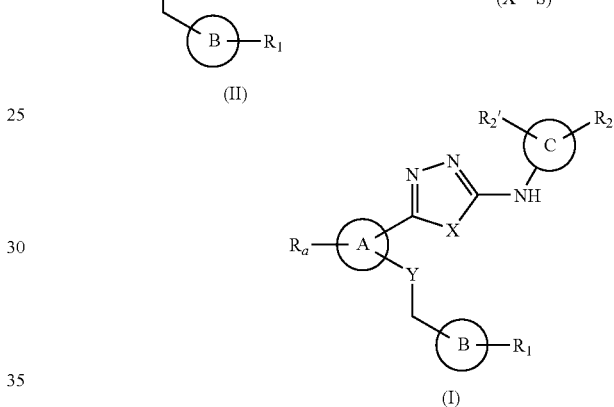

It is possible to produce the compound (II) in accordance with the synthetic route A-2. That is, it is possible to obtain the compound (II) by reacting a compound (III) with isocyanate (IV; X=O) or isothiocyanate (IV; X=S) in an organic solvent such as methanol at a temperature from room temperature to 100° C. for one hour to 24 hours.

Synthetic Route A-2

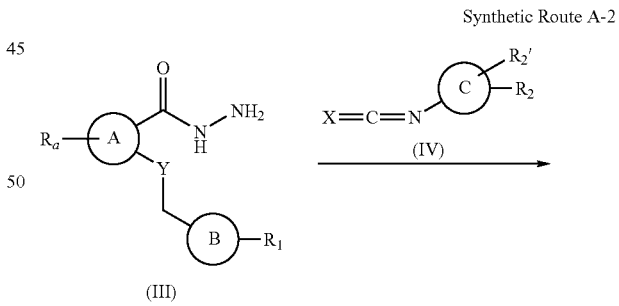

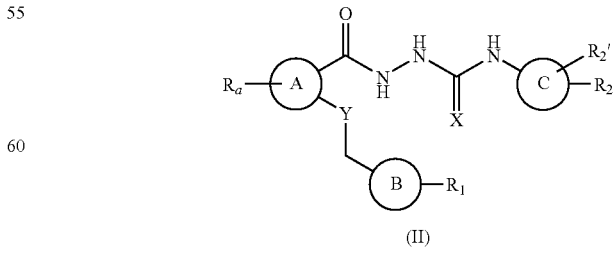

It is possible to produce the compound (III) in accordance with the synthetic route A-3. That is, it is possible to obtain the compound (III) by reacting a compound (V) with a hydrazine hydrate (VI) in an organic solvent such as methylene chloride or methanol at room temperature or under reflux conditions for one hour to 24 hours.

Synthetic Route A-3

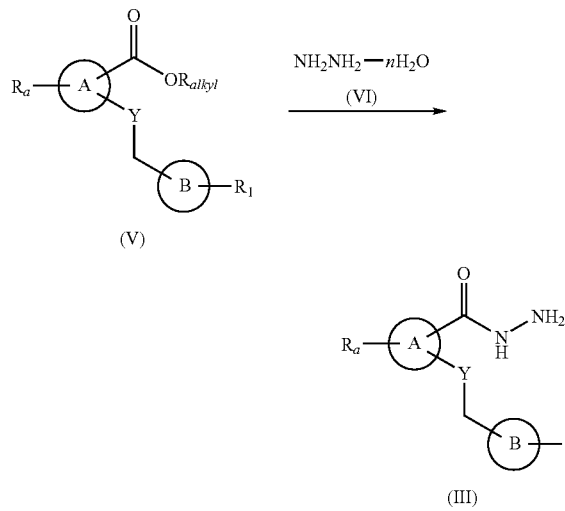

It is possible to produce the compound (V) in accordance with the synthetic route A-4. That is, it is possible to obtain the compound (V) by reacting a compound (VII) with a compound (VIII) in an organic solvent such as tetrahydrofuran in the presence of a base such as potassium carbonate at a temperature from room temperature to 100° C. for one hour to 24 hours.

Synthetic Route A-4

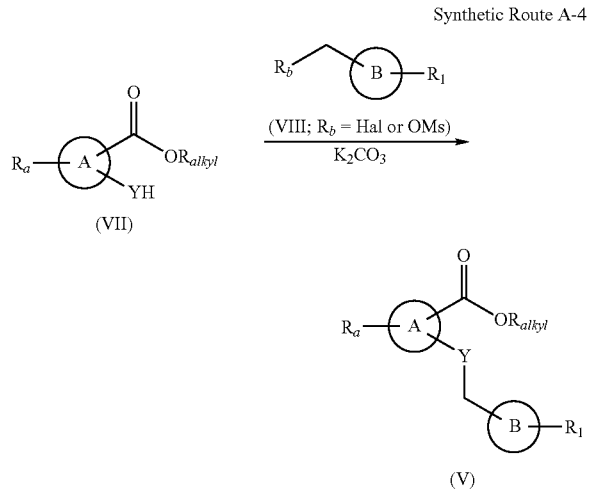

It is also possible to produce the compound (II) used in the synthetic route A-1 in accordance with the synthetic route A-5. That is, it is possible to obtain the compound (II) by subjecting a compound (IX) and semicarbazide (X; atom X=O) or thiosemicarbazide (X; atom X=S) to dehydration condensation in an organic solvent such as N,N-dimethylformamide using water-soluble carbodiimide such as EDC-HCl and a base such as triethylamine for one hour to 24 hours.

Synthetic Route A-5

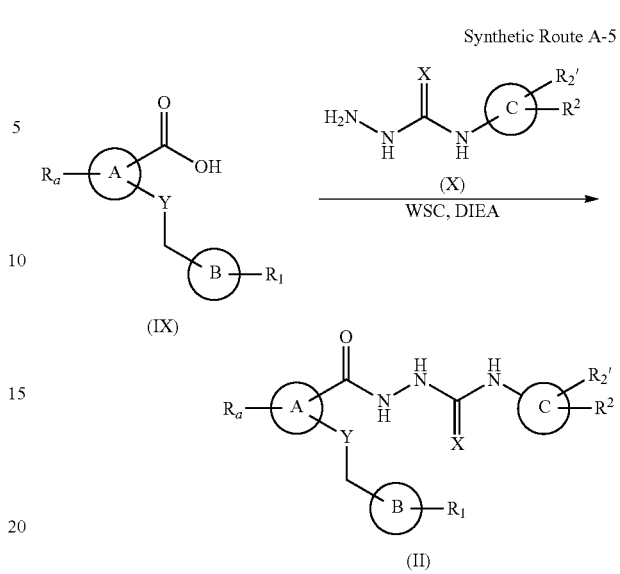

It is possible to produce the compound (IX) in accordance with the synthetic route A-6. That is, it is possible to obtain the compound (IX) by subjecting the compound (V) produced by the synthetic route A-4 to hydrolysis in an organic solvent such as ethanol in the presence of a base such as an aqueous sodium hydroxide solution at a temperature from room temperature to 100° C. for one hour to 24 hours.

Synthetic Route A-6

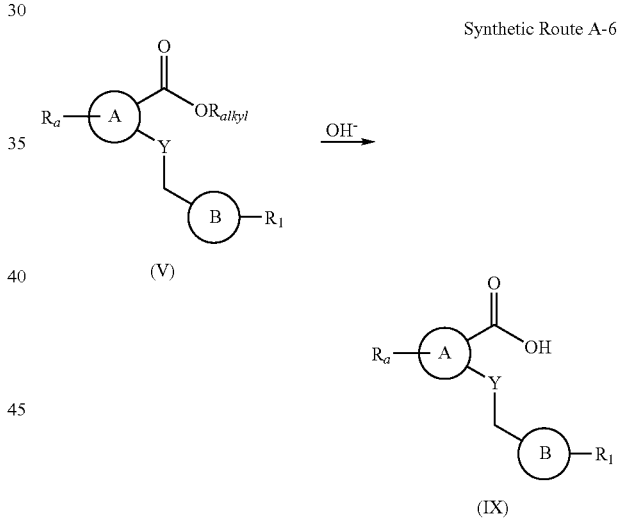

It is also possible to produce the compound (IX) used in the synthetic route A-5 in accordance with the synthetic route A-7. That is, it is possible to obtain the compound (IX) by reacting a compound (XI) with a compound (VIII) in an organic solvent such as N,N-dimethylformamide using a base such as triethylamine for one hour to 24 hours.

Synthetic Route A-7

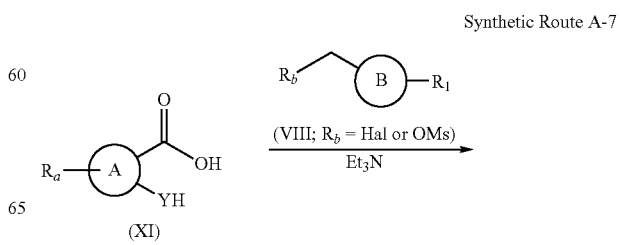

-continued

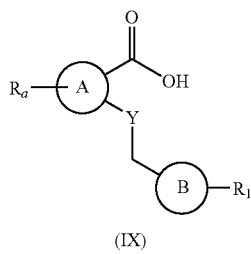

(IX)

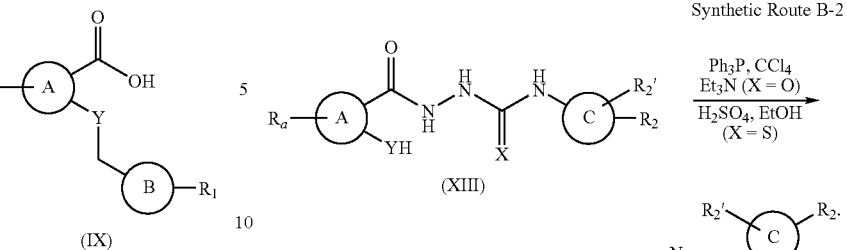

(XIII)

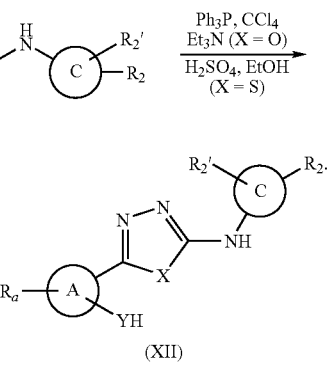

(XII)

General Synthetic Route B

It is possible to synthesize a part of the present compound (I) by the general synthetic route B depending on the types of $R_1$ group and $R_2$ group. Specific methods (B-1 to -4) of the general synthetic route B are described below.

It is possible to produce the present compound (I) in accordance with the synthetic route B-1. That is, it is possible to obtain the compound (I) by reacting a compound (XII) with a compound (VIII) in an organic solvent such as tetrahydrofuran in the presence of a base such as potassium carbonate at a temperature from room temperature to 100° C. for one hour to 24 hours.

It is possible to produce the compound (XIII) in accordance with the synthetic route B-3. That is, it is possible to obtain the compound (XIII) by reacting a compound (XIV) with isocyanate (IV; X=O) or isothiocyanate (IV; X=S) in an organic solvent such as methanol at a temperature from room temperature to 100° C. for one hour to 24 hours.

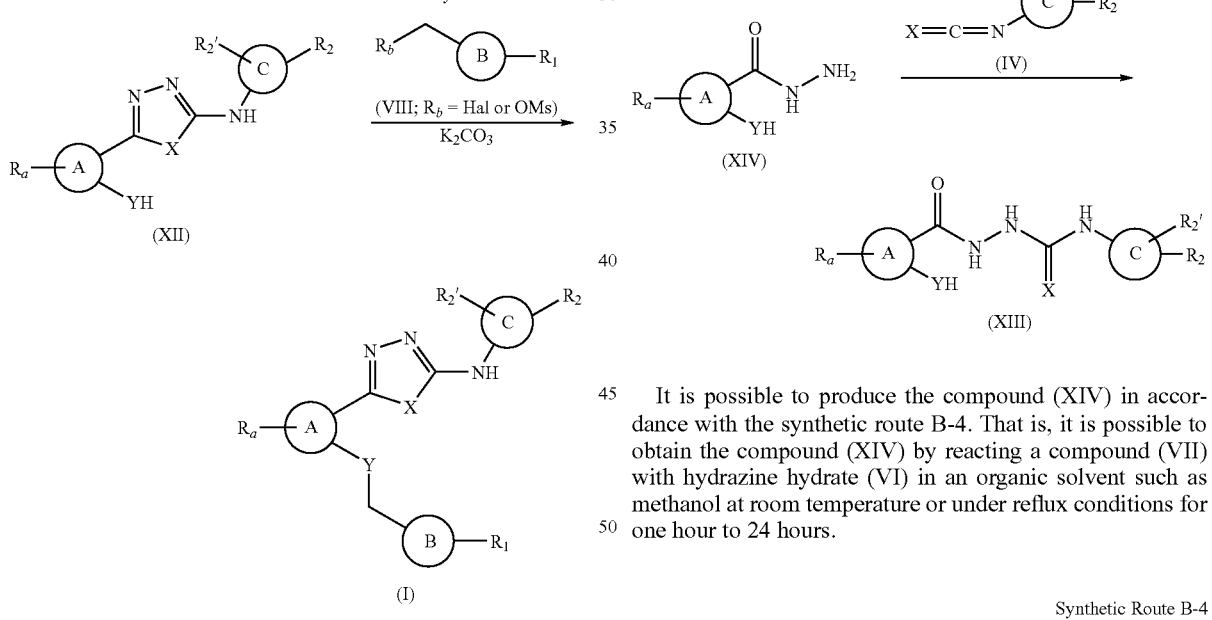

It is possible to produce the compound (XII) in accordance with the synthetic route B-2. That is, in the case where X is an oxygen atom, it is possible to obtain the compound (XII; X=O) by reacting a compound (XIII; X=O) in an organic solvent such as methylene chloride using triphenylphosphine, carbon tetrachloride and an organic base such as triethylamine at a temperature from room temperature to 100° C. for one hour to 24 hours. Also, in the case where X is a sulfur atom, it is possible to obtain the compound (XII; X=S) by reacting a compound (XIII; X=S) with concentrated sulfuric acid in an organic solvent such as ethanol at a temperature from room temperature to 100° C. for one hour to 24 hours.

It is possible to produce the compound (XIV) in accordance with the synthetic route B-4. That is, it is possible to obtain the compound (XIV) by reacting a compound (VII) with hydrazine hydrate (VI) in an organic solvent such as methanol at room temperature or under reflux conditions for one hour to 24 hours.

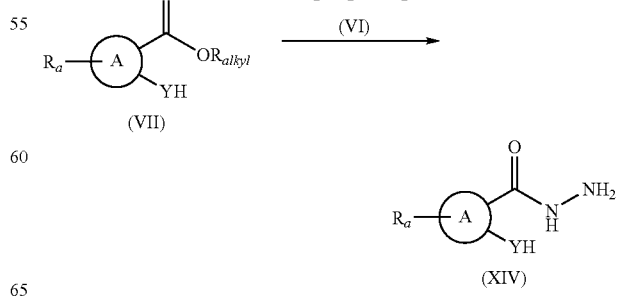

General Synthetic Route C

It is also possible to synthesize some of the present compounds (I; Y═S) also by the general synthetic route C depending on the types of $R_1$ group and $R_2$ group. Specific methods (C-1 to -6) of the general synthetic route C are described below.

It is possible to produce the present compound (I; Y═S) in accordance with the synthetic route C-1. That is, it is possible to obtain the compound (I; Y═S) by reacting a compound (XV) with the compound (VIII) in an organic solvent such as tetrahydrofuran in the presence of a base such as sodium t-butoxide at a temperature from an ice cooling temperature to room temperature for one hour to 24 hours.

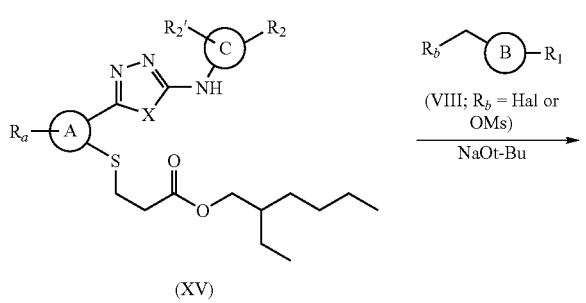

It is possible to produce the compound (XV) in accordance with the synthetic route C-2. That is, it is possible to obtain the compound (XV) by reacting a compound (XVI) with 2-ethylhexyl 3-mercaptopropionate (XVII) in an organic solvent such as dioxane using a ligand such as 4,5-bis(diphenylphosphino)-9,9-dimethylxanthene (Xantphos) and a transition metal catalyst such as bis(dibenzylideneacetone)palladium (Pd(dba)₂) in the presence of an organic base such as diisopropylethylamine (DIEA) at a temperature from room temperature to 150° C. for one hour to 24 hours.

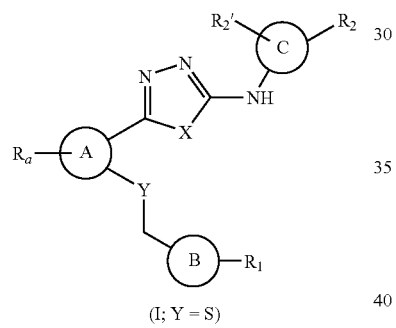

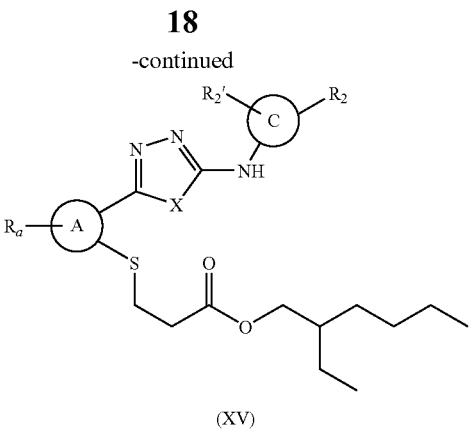

It is also possible to produce the compound (I; Y═S) in accordance with the synthetic route C-3. That is, it is possible to obtain the compound (I; Y═S) by reacting the compound (XVI) with a compound (XVIII) in an organic solvent such as dioxane using a ligand such as 4,5-bis(diphenylphosphino)-9,9-dimethylxanthene (Xantphos) and a transition metal catalyst such as bis(dibenzylideneacetone)palladium (Pd(dba)₂) in the presence of an organic base such as diisopropylethylamine (DIEA) at a temperature from room temperature to 150° C. for one hour to 24 hours.

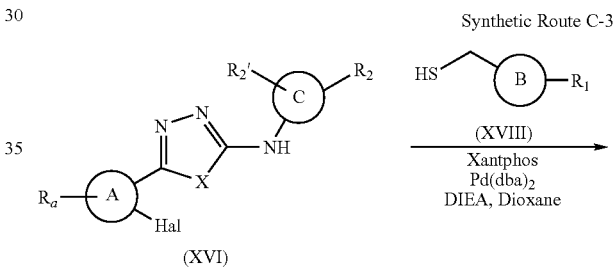

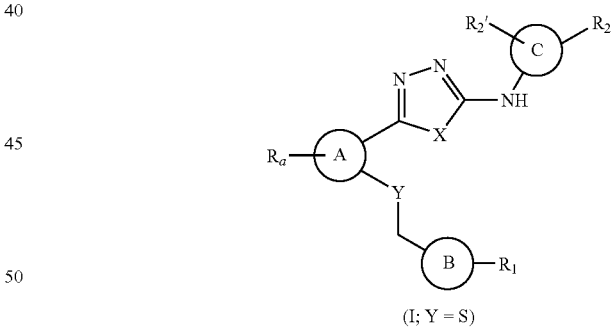

It is possible to produce the compound (XVI) in accordance with the synthetic route C-4. That is, in the case where X is an oxygen atom, it is possible to obtain the compound (XVI; X═O) by reacting a compound (XIX; X═O) in an organic solvent such as methylene chloride using triphenylphosphine, carbon tetrachloride and an organic base such as triethylamine at a temperature from room temperature to 100° C. for one hour to 24 hours. Also, in the case where X is a sulfur atom, it is possible to obtain the compound (XVI; X═S) by reacting a compound (XIX; X═S) with concentrated sulfuric acid in an organic solvent such as ethanol at a temperature from room temperature to 100° C. for one hour to 24 hours.

Synthetic Route C-4

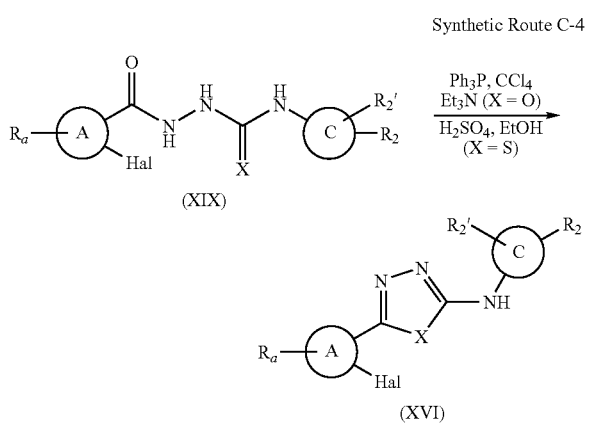

It is possible to produce the compound (XIX) in accordance with the synthetic route C-5. That is, it is possible to obtain the compound (XIX) by reacting a compound (XX) with isocyanate (IV; X=O) or isothiocyanate (IV; X=S) in an organic solvent such as methanol at a temperature from room temperature to 100° C. for one hour to 24 hours.

Synthetic Route C-5

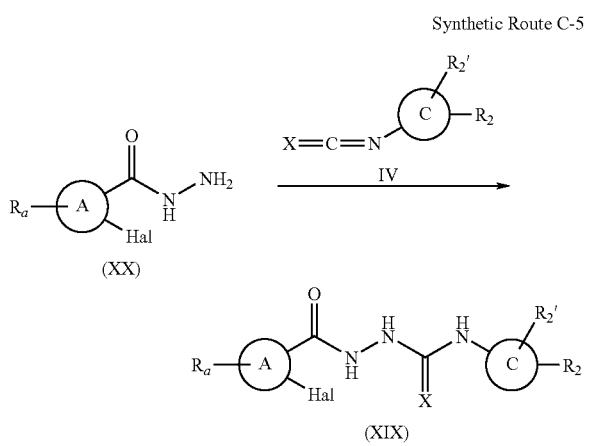

It is possible to produce the compound (XX) in accordance with the synthetic route C-6. That is, it is possible to obtain the compound (XX) by reacting a compound (XXI) with hydrazine hydrate (VI) in an organic solvent such as methanol at room temperature or under reflux conditions for one hour to 24 hours.

Synthetic Route C-6

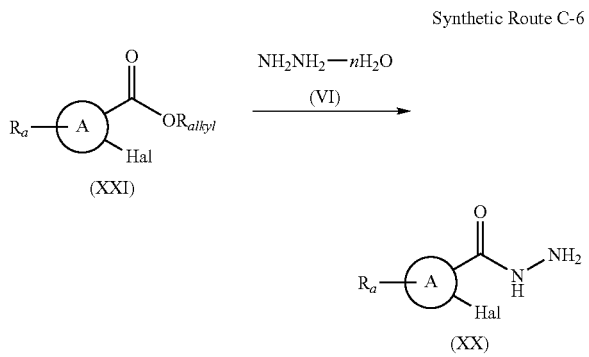

It is possible to convert each of the present compounds produced by the above mentioned synthetic routes into the above-described salt, hydrate, or solvate by a widely used technique.

In order to find usefulness of the present compounds, a test of inhibitory effect of tyrosine kinase (KDR) activity was conducted on the present compounds using an evaluation system for kinase (KDR) inhibitory activity by way of the ELISA method which is the method for evaluating neovascularization inhibition effect of drugs, and the neovascularization inhibition effects were evaluated. Details of the evaluation will be described in [Pharmacological Test] in Examples described later in this specification, and it was found that the present compounds exhibit an excellent tyrosine kinase (KDR) inhibitory action and have an excellent neovascularization inhibition effect.

As previously described, it has been reported that the neovascularization is deeply associated with the diseases such as cancer, rheumatoid arthritis, age-related macular degeneration, diabetic retinopathy, retinopathy of prematurity, retinal vein occlusion, polypoidal choroidal vasculopathy, diabetic macular edema, plaque psoriasis, atherosclerosis, and the like. Therefore, the present compounds are greatly expected as therapeutic agents for the diseases associated with the neovascularization.

The present compounds can be administered orally or parenterally. Examples of a dosage form include a tablet, a capsule, a granule, a powder, an injection, an ointment, an eye drop, an eye ointment, and the like, and these may be prepared by a widely used technique.

For example, an oral preparation such as a tablet, a capsule, a granule, or a powder can be prepared by optionally adding an excipient such as lactose, mannitol, starch, crystalline cellulose, light silicic anhydride, calcium carbonate, or calcium hydrogen phosphate; a lubricant such as stearic acid, magnesium stearate, or talc; a binder such as starch, hydroxypropyl cellulose, hydroxypropylmethyl cellulose, or polyvinylpyrrolidone; a disintegrant such as carboxymethyl cellulose, low-substituted hydroxypropylmethyl cellulose, or calcium citrate; a coating agent such as hydroxypropylmethyl cellulose, macrogol, or a silicone resin; a stabilizer such as ethyl parahydroxybenzoate or benzyl alcohol; a corrigent such as a sweetener, a sour agent, or a flavor, or the like.

Further, a parenteral preparation such as an injection or an eye drop can be prepared by optionally adding a tonicity agent such as sodium chloride, concentrated glycerin, propylene glycol, polyethylene glycol, potassium chloride, sorbitol, or mannitol; a buffer such as sodium phosphate, sodium hydrogen phosphate, sodium acetate, citric acid, glacial acetic acid, or trometamol; a surfactant such as polyoxyethylene sorbitan monooleate, polyoxy 40 stearate, or polyoxyethylene hydrogenated castor oil; a stabilizer such as sodium citrate or sodium edetate; a preservative such as benzalkonium chloride, paraben, benzothonium chloride, parahydroxybenzoic acid ester, sodium benzoate, or chlorobutanol; a pH adjusting agent such as hydrochloric acid, citric acid, phosphoric acid, glacial acetic acid, sodium hydroxide, sodium carbonate, or sodium hydrogen carbonate; a soothing agent such as benzyl alcohol, or the like.

The present invention also relates to a method for treating diseases associated with neovascularization, comprising administering a therapeutically effective amount of the present compound or the salt thereof to a patient (especially human).

The dose of the present compound can be appropriately selected depending on the symptoms, age, dosage form, or the like. For example, in the case of an oral preparation, it can be administered in an amount of generally from 0.01 to 1000 mg, preferably from 1 to 100 mg per day in a single dose or several divided doses. Further, in the case of an eye drop, a preparation containing the present compound at a concentration of generally from 0.0001 to 10% (w/v), preferably from 0.01 to 5% (w/v) can be administered in a single dose or several divided doses.

PRODUCTION EXAMPLE

Reference Example 1

Methyl 2-(pyridin-4-yl)methoxybenzoate (Reference Compound 1-(1))

To a solution of methyl salicylate (10 g, 66 mmol) and 4-chloromethylpyridine hydrochloride (11 g, 67 mmol) in N,N-dimethylformamide (150 mL) was added potassium carbonate (19 g, 140 mmol) under ice-cooling, and then the mixture was allowed to warm to room temperature and stirred overnight. The reaction mixture was poured into an ice water and the aqueous layer was extracted with ethyl acetate (150 mL, twice). The ethyl acetate layer was washed with a saturated brine solution (200 mL), dried over anhydrous sodium sulfate, and concentrated under a reduced pressure to dryness, and the resultant residue was purified with a silica gel column chromatography (hexane/ethyl acetate) and dried to give 12 g (75%) of the titled compound as a colorless solid.

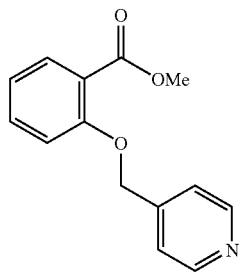

$^1$H-NMR (300 MHz, CDCl$_3$)
δ 3.93 (s, 3H), 5.19 (s, 2H), 6.97 (d, J=8.3 Hz, 1H), 7.04 (t, J=7.5 Hz, 1H), 7.43-7.50 (m, 3H), 7.87 (dd, J=7.9, 1.8 Hz, 1H), 8.63 (d, J=6.1 Hz, 2H)

The following Reference Compounds 1-(2) to (8) were obtained by a production method similar to that of Reference Compound 1-(1) using compounds selected from known compounds, 4-chloromethylquinoline (CAS#5632-17-7; WO 2006/093253) and 2-acetamido-4-methanesulfonyloxymethylpyridine (CAS#864461-12-1; WO 2005/085201) and commercially available compounds.

Methyl 2-(quinolin-4-yl)methoxybenzoate (Reference Compound 1-(2))

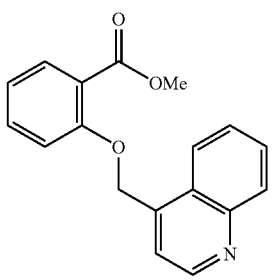

$^1$H-NMR (300 MHz, DMSO-d$_6$)
δ 3.84 (s, 3H), 5.78 (s, 2H), 7.10 (m, 1H), 7.49 (d, J=8.1 Hz, 1H), 7.58-7.71 (m, 2H), 7.77 (dd, J=7.7, 1.8 Hz, 1H), 7.81 (m, 1H), 7.84 (d, J=4.4 Hz, 1H), 8.08 (d, J=7.9 Hz, 1H), 8.22 (d, J=8.1 Hz, 1H), 8.96 (d, J=4.2 Hz, 1H)

Methyl 2-(2-acetamidopyridin-4-yl)methoxybenzoate (Reference Compound 1-(3))

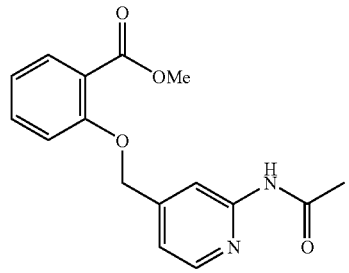

$^1$H-NMR (300 MHz, DMSO-d$_6$)
δ 2.10 (s, 3H), 3.85 (s, 3H), 5.26 (s, 2H), 7.06 (dd, J=7.2, 7.2 Hz, 1H), 7.21 (m, 2H), 7.54 (m, 1H), 7.71 (dd, J=7.5, 1.7 Hz, 1H), 8.18 (s, 1H), 8.31 (d, J=5.1 Hz, 1H), 10.50 (s, 1H)

Methyl 3-(pyridin-4-yl)methoxythiophene-2-carboxylate (Reference Compound 1-(4))

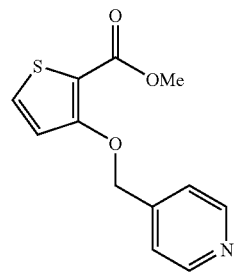

$^1$H-NMR (300 MHz, DMSO-d$_6$)
δ 3.77 (s, 3H), 5.36 (s, 2H), 7.15 (d, J=5.5 Hz, 1H), 7.46 (d, J=5.3 Hz, 2H) 7.84 (d, J=5.5 Hz, 1H), 8.59 (dd, J=5.3, 1.5 Hz, 2H)

Methyl 5-bromo-2-(pyridin-4-yl)methoxybenzoate (Reference Compound 1-(5))

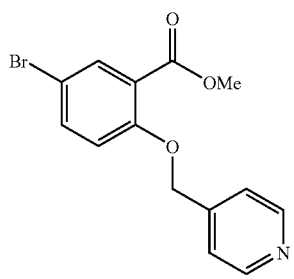

$^1$H-NMR (300 MHz, CDCl$_3$)
δ 3.93 (s, 3H), 5.17 (s, 2H), 6.86 (d, J=9.0 Hz, 1H), 7.44 (d, J=6.1 Hz, 2H), 7.55 (dd, J=9.0, 2.6 Hz, 1H), 7.99 (d, J=2.6 Hz, 1H), 8.64 (d, J=6.1 Hz, 2H)

Methyl 5-methoxy-2-(pyridin-4-yl)methoxybenzoate (Reference Compound 1-(6))

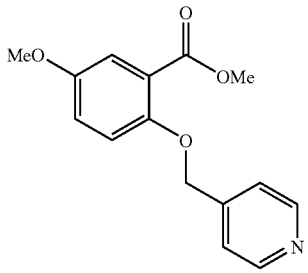

$^1$H-NMR (300 MHz, DMSO-d$_6$)
δ 3.74 (s, 3H), 3.84 (s, 3H), 5.20 (s, 2H), 7.10-7.24 (m, 3H), 7.48 (d, J=5.1 Hz, 2H), 8.59 (d, J=5.1 Hz, 2H)

Methyl 3-(pyridin-4-yl)methoxypicolate (Reference Compound 1-(7))

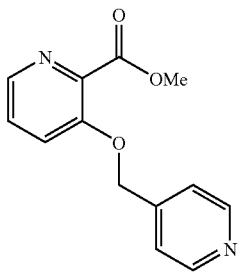

$^1$H-NMR (300 MHz, DMSO-d$_6$)
δ 3.88 (s, 3H), 5.34 (s, 2H), 7.43 (d, J=5.3 Hz, 2H), 7.54-7.63 (m, 1H), 7.70 (d, J=8.6 Hz, 1H), 8.22 (d, J=4.2 Hz, 1H), 8.60 (d, J=5.3 Hz, 2H)

Methyl 3-(2-acetamidopyridin-4-yl)methoxythiophene-2-carboxylate (Reference Compound 1-(8))

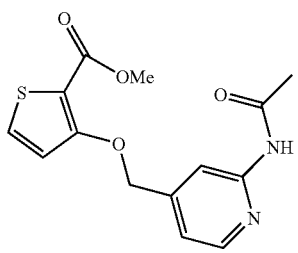

$^1$H-NMR (300 MHz, DMSO-d$_6$)
δ 2.09 (s, 3H), 3.79 (s, 3H), 5.34 (s, 2H), 7.13-7.18 (m, 2H), 7.83 (d, J=5.7 Hz, 1H), 8.18 (s, 1H), 8.30 (d, J=5.1 Hz, 1H), 10.52 (s, 1H)

Reference Example 2

2-(Pyridin-4-yl)methoxybenzoylhydrazide (Reference Compound 2-(1))

To a solution of methyl 2-(pyridine-4-yl) methoxybenzoate (5.8 g, 24 mmol; Reference Compound 1-(1)) in methanol (20 mL) was added hydrazine monohydrate (4.6 g, 92 mmol) at room temperature and the mixture was refluxed for 7 hours. The reaction solution was concentrated and the residue was suspended in methanol and the resultant solid was filtered off. The solid was dried under a reduced pressure to give 3.7 g (63%) of the titled compound as a colorless solid.

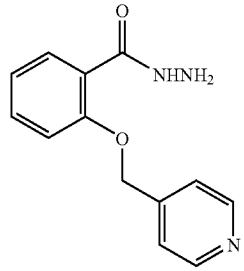

$^1$H-NMR (300 MHz, CDCl$_3$)
δ 4.17 (br s, 2H), 5.27 (s, 2H), 6.91 (d, J=8.4 Hz, 1H), 7.14 (t, J=7.7 Hz, 1H), 7.33 (d, J=5.9 Hz, 2H), 7.43 (m, 1H), 8.22 (dd, J=7.7, 1.7 Hz, 1H), 8.67 (d, J=5.9 Hz, 2H), 8.78 (brs, 1H)

The following Reference Compounds 2-(2) to (8) were obtained by a production method similar to that of Reference Compound 2-(1) using compounds selected from Reference Compounds 1-(2) and (4) to (7), known compounds and commercially available compounds.

2-(Quinolin-4-yl)methoxybenzoylhydrazide (Reference Compound 2-(2))

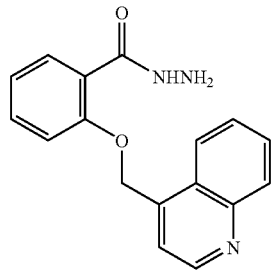

$^1$H-NMR (300 MHz, DMSO-d$_6$)
δ 4.52 (s, 2H), 5.78 (s, 2H), 7.06 (m, 1H), 7.31 (d, J=7.9 Hz, 1H), 7.44 (m, 1H), 7.56 (dd, J=7.5, 1.7 Hz, 1H), 7.66-7.71 (m, 2H), 7.82 (m, 1H), 8.08 (d, J=7.5 Hz, 1H), 8.22 (d, J=7.5 Hz, 1H), 8.91 (d, J=4.0 Hz, 1H), 9.32 (s, 1H)

3-(Pyridin-4-yl)methoxythiophene-2-carbohydrazide (Reference Compound 2-(3))

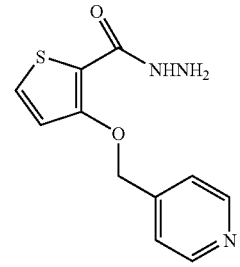

$^1$H-NMR (300 MHz, DMSO-d$_6$)
δ 4.50 (br s, 2H), 5.38 (s, 2H), 7.05 (d, J=5.5 Hz, 1H), 7.46 (d, J=5.3 Hz, 2H), 7.84 (d, J=5.5 Hz, 1H), 8.58-8.60 (m, 3H)

5-Bromo-2-(pyridin-4-yl)methoxybenzoylhydrazide (Reference Compound 2-(4))

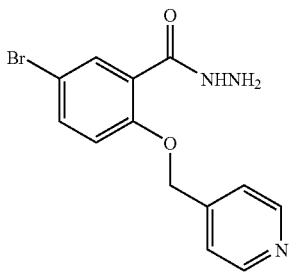

$^1$H-NMR (300 MHz, CDCl$_3$)

δ 4.16 (d, J=4.0 Hz, 2H), 5.25 (s, 2H), 6.80 (d, J=8.8 Hz, 1H), 7.30 (d, J=5.9 Hz, 2H), 7.50 (dd, J=8.8, 2.6 Hz, 1H), 8.33 (d, J=2.6 Hz, 1H), 8.68 (d, J=5.9 Hz, 2H), 8.72 (br s, 1H)

5-Methoxy-2-(pyridin-4-yl)methoxybenzoylhydrazide (Reference Compound 2-(5))

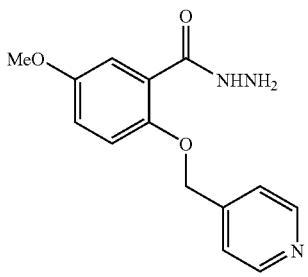

$^1$H-NMR (300 MHz, DMSO-d$_6$)

δ 3.72 (s, 3H), 4.54 (s, 2H), 5.23 (s, 2H), 6.45-7.05 (m, 2H), 7.13 (m, 1H), 7.44 (d, J=4.2 Hz, 2H), 8.56 (d, J=4.2 Hz, 2H), 9.33 (s, 1H)

3-(Pyridin-4-yl)methoxypicolinoylhydrazide (Reference Compound 2-(6))

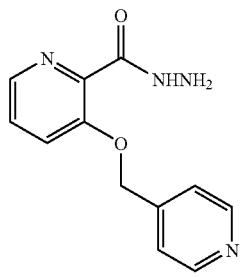

$^1$H-NMR (300 MHz, DMSO-d$_6$)

δ 4.51 (s, 2H), 5.29 (s, 2H), 7.42-7.48 (m, 3H), 7.56 (d, J=8.3 Hz, 1H), 8.16 (d, J=4.2 Hz, 1H), 8.58 (d, J=5.9 Hz, 2H) 9.53 (s, 1H)

3-Bromothiophene-2-carbohydrazide (Reference Compound 2-(7))

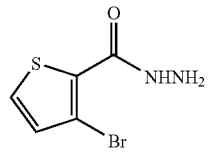

$^1$H-NMR (300 MHz, DMSO-d$_6$)

δ 9.44 (1H, s), 7.77 (1H, d, J=5.1 Hz), 7.16 (1H, d, J=5.1 Hz), 4.55 (2H, s)

2-Bromothiophene-3-carbohydrazide (Reference Compound 2-(8))

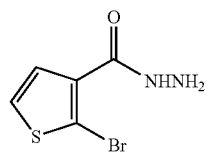

$^1$H-NMR (300 MHz, DMSO-d$_6$)

δ 9.54 (1H, s), 7.63 (1H, d, J=5.7 Hz), 7.20 (1H, d, J=5.7 Hz), 4.58 (2H, s)

Reference Example 3

2-(2-Acetamidopyridin-4-yl)methoxybenzoic acid (Reference Compound 3-(1))

To a solution of methyl 2-(2-acetamidopyridin-4-yl) methoxy benzoate (1.1 g, 3.7 mmol; Reference Compound 1-(3)) in tetrahydrofuran (10 mL) was added a 1 M aqueous sodium hydroxide solution (8.0 mL, 8.0 mmol) under ice-cooling and then the mixture was allowed to warm to room temperature and stirred overnight. To the reaction solution was added a 1M hydrochloric acid (8.0 mL, 8.0 mmol) under ice-cooling. The precipitated solid was filtered off and dried under a reduced pressure to give 510 mg (48%) of the titled compound as a colorless solid.

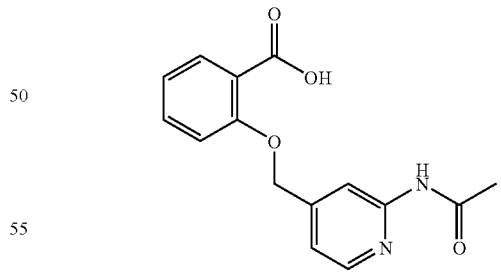

$^1$H-NMR (300 MHz, DMSO-d$_6$)

δ 2.09 (s, 3H), 5.25 (s, 2H), 7.04 (m, 1H), 7.15 (d, J=8.4 Hz, 1H), 7.25 (d, J=6.6 Hz, 1H), 7.47 (m, 1H), 7.68 (dd, J=7.5, 1.8 Hz, 1H), 8.15 (s, 1H), 8.29 (d, J=5.1 Hz, 1H), 10.49 (s, 1H), 12.69 (brs, 1H)

The following Reference Compound 3-(2) was obtained by a production method similar to that of Reference Compound 3-(1) using compounds selected from Reference Compound 1-(8) and commercially available compounds.

3-(2-Acetamidopyridin-4-yl)methoxythiophene-2-carboxylic acid (Reference Compound 3-(2))

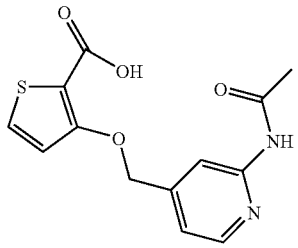

¹H-NMR (300 MHz, DMSO-d₆)
δ 2.09 (s, 3H), 5.31 (s, 2H), 7.08 (d, J=5.5 Hz, 1H), 7.18 (d, J=6.0 Hz, 1H), 7.74 (d, J=5.5 Hz, 1H), 8.12 (s, 1H), 8.29 (d, J=6.0 Hz, 1H), 10.51 (s, 1H), 12.60 (br s, 1H)

Reference Example 4

2-(2-Acetamidopyridin-4-yl)methylthionicotinic acid (Reference Compound 4-(1))

To a suspension of 2-acetamido-4-methanesulfonyloxymethylpyridine (CAS#864461-12-1; WO2005/085201) (2.2 g, 9.0 mmol) and 2-mercaptonicotinic acid (1.5 g, 9.9 mmol) in N,N-'dimethylformamide (25 mL) was added triethylamine (3.8 mL, 27 mmol) under ice-cooling, and then the mixture was stirred at 40° C. overnight. The reaction mixture was diluted with ethyl acetate (80 mL) and extracted with a 0.1 M aqueous sodium hydroxide solution (200 mL). The pH of the aqueous layer was adjusted to 7 by adding 1 M hydrochloric acid. The precipitated solid was filtered off and dried under a reduced pressure to give 1.8 g (yield: 66%) of the titled Reference as a brown solid.

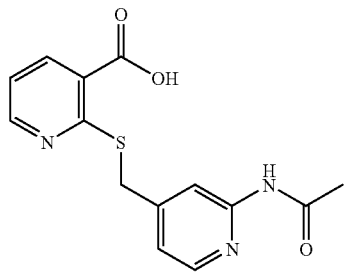

¹H-NMR (500 MHz, DMSO-d₆) δ 2.07 (s, 3H), 4.36 (s, 2H), 7.11 (dd, J=5.2, 1.5 Hz, 1H), 7.26 (dd, J=7.6, 4.9 Hz, 1H), 8.18 (d, J=5.2 Hz, 1H), 8.23 (dd, J=7.6, 1.8 Hz, 1H), 8.63 (dd, J=4.9, 1.8 Hz, 1H), 10.41 (s, 1H), 13.47 (br s, 1H)

The following Reference Compound 4-(2) was obtained by a production method similar to that of Reference Compound 4-(1) using compounds selected from known compounds, 4-bromomethyl-2-methylaminocarbonylpyridine (CAS#872706-94-0; WO2006/002383) and commercially available compounds.

2-(2-Methylaminocarbonylpyridin-4-yl)methylthionicotinic acid (Reference Compound 4-(2))

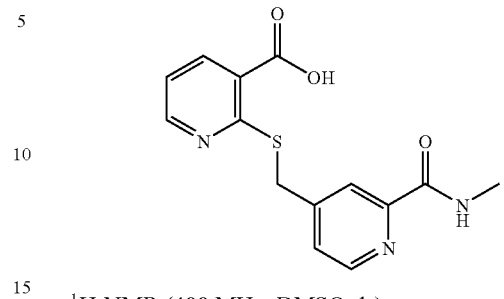

¹H-NMR (400 MHz, DMSO-d₆)
δ 2.80 (d, J=5.1 Hz, 3H), 4.47 (s, 2H), 7.26 (dd, J=7.7, 4.8 Hz, 1H), 7.61 (m, 1H), 8.06 (d, J=0.7 Hz, 1H), 8.23 (dd, J=7.7, 1.8 Hz, 1H), 8.50 (dd, J=5.1, 0.7 Hz, 1H), 8.60 (dd, J=4.8, 1.8 Hz, 1H), 8.72 (q, J=5.1 Hz, 1H), 13.40 (br s, 1H)

Reference Example 5

1-(2-Bromobenzoyl)-4-phenylsemicarbazide (Reference Compound 5-(1))

To a solution of 2-bromobenzohydrazide (500 mg, 2.3 mmol) in methanol (5 mL) was added phenyl isocyanate (280 mg, 2.4 mmol) at room temperature, and then the mixture was refluxed for one hour. The reaction mixture was cooled to room temperature. The precipitated solid was filtered off and dried under a reduced pressure to give 370 mg (48%) of the titled compound as a colorless solid.

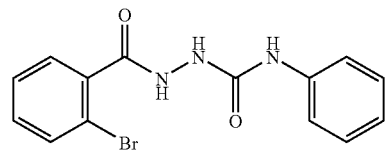

¹H-NMR (300 MHz, DMSO-d₆)
δ 6.70 (t, J=7.3 Hz, 1H), 7.27 (t, J=7.5 Hz, 2H), 7.40-7.55 (m, 5H), 7.70 (d, J=7.7 Hz, 1H), 8.32 (s, 1H), 8.75 (s, 1H), 10.19 (s, 1H)

The following Reference Compound 5-(2) to (22) and 6-(1) to (16) were obtained by a production method similar to that of Reference Compound 5-(1) using compounds selected from Reference Compounds 2-(1) to (8), known compounds and commercially available compounds.

1-(2-Bromobenzoyl)-4-(4-chlorophenyl)semicarbazide (Reference Compound 5-(2))

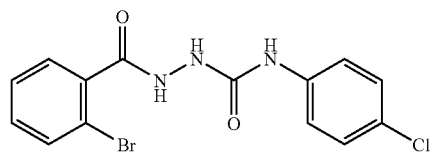

¹H-NMR (300 MHz, DMSO-d₆)
δ 7.32 (d, J=8.8 Hz, 2H), 7.38-7.56 (m, 5H), 7.70 (d, J=7.7 Hz, 1H), 8.41 (s, 1H), 8.92 (s, 1H), 10.19 (s, 1H)

1-(2-Bromobenzoyl)-4-(3-trifluoromethylphenyl)semicarbazide (Reference Compound 5-(3))

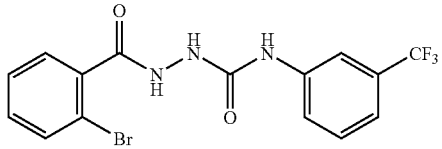

¹H-NMR (300 MHz, DMSO-d₆) δ 7.31 (t, J=7.9 Hz, 1H), 7.38-7.60 (m, 4H), 7.62-7.74 (m, 2H), 8.01 (s, 1H), 8.55 (s, 1H), 9.18 (s, 1H), 10.20 (s, 1H)

1-(2-Bromobenzoyl)-4-(4-t-buthylphenyl)semicarbazide (Reference Compound 5-(4))

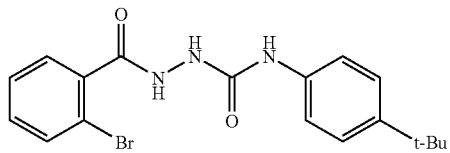

¹H-NMR (300 MHz, DMSO-d₆)
δ 1.26 (s, 9H), 7.29 (d, J=8.8 Hz, 2H), 7.37 (d, J=8.8 Hz, 2H), 7.40-7.55 (m, 3H), 7.70 (d, J=7.9 Hz, 1H), 8.26 (s, 1H), 8.64 (s, 1H), 10.17 (s, 1H)

1-(2-Bromobenzoyl)-4-(4-trifluoromethoxyphenyl)semicarbazide (Reference Compound 5-(5))

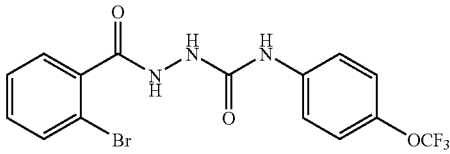

¹H-NMR (300 MHz, DMSO-d₆)
δ 7.28 (d, J=9.0 Hz, 2H), 7.38-7.56 (m, 3H), 7.58 (d, J=9.0 Hz, 2H), 7.70 (d, J=7.9 Hz, 1H), 8.44 (s, 1H), 8.99 (s, 1H), 10.19 (s, 1H)

1-(2-Bromobenzoyl)-4-phenylthiosemicarbazide (Reference Compound 5-(6))

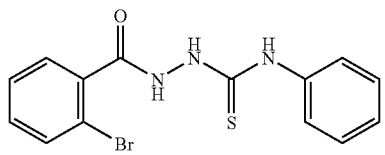

¹H-NMR (300 MHz, DMSO-d₆)
δ 7.18 (t, J=7.5 Hz, 1H), 7.35 (t, J=7.5 Hz, 2H), 7.39-7.50 (m, 4H), 7.71 (d, J=7.9 Hz, 1H), 7.78 (d, J=7.9 Hz, 1H), 9.70 (br s, 1H), 9.86 (br s, 1H), 10.46 (s, 1H)

1-(2-Bromobenzoyl)-4-(4-chlorophenyl)thiosemicarbazide (Reference Compound 5-(7))

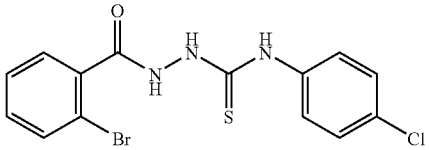

¹H-NMR (300 MHz, DMSO-d₆) δ 7.36-7.60 (m, 6H), 7.71 (d, J=7.7 Hz, 1H), 7.78 (m, 1H), 9.70 (br s, 1H), 9.97 (s, 1H), 10.48 (s, 1H)

1-(2-Bromobenzoyl)-4-(3-chlorophenyl)thiosemicarbazide (Reference Compound 5-(8))

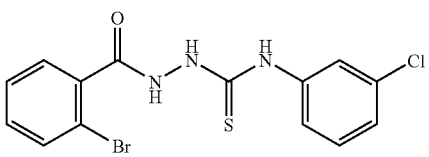

¹H-NMR (300 MHz, DMSO-d₆)
δ 7.22 (d, J=7.7 Hz, 1H), 7.38 (t, J=8.1 Hz, 1H), 7.42-7.54 (m, 3H), 7.68-7.80 (m, 3H), 9.80 (br s, 1H), 10.04 (s, 1H), 10.49 (s, 1H)

1-(2-Bromobenzoyl)-4-(4-t-butylphenyl)thiosemicarbazide (Reference Compound 5-(9))

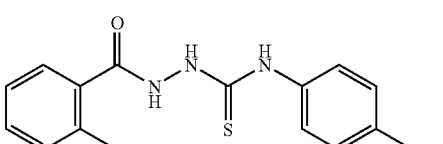

¹H-NMR (300 MHz, DMSO-d₆)
δ 1.29 (s, 9H), 7.35-7.55 (m, 6H), 7.70 (d, J=7.9 Hz, 1H), 7.76 (d, J=7.3 Hz, 1H), 9.58 (br s, 1H), 9.80 (br s, 1H), 10.45 (s, 1H)

1-(2-Bromobenzoyl)-4-(4-trifluoromethylphenyl)thiosemicarbazide (Reference Compound 5-(10))

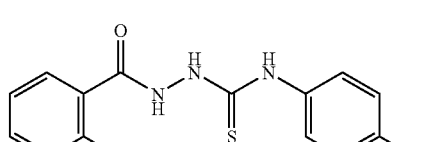

¹H-NMR (300 MHz, DMSO-d₆)
δ 7.40-7.55 (m, 2H), 7.68-7.86 (m, 6H), 9.80 (s, 1H), 10.13 (s, 1H), 10.53 (br s, 1H)

31

1-(2-Bromobenzoyl)-4-(4-trifluoromethoxyphenyl)thiosemicarbazide (Reference Compound 5-(11))

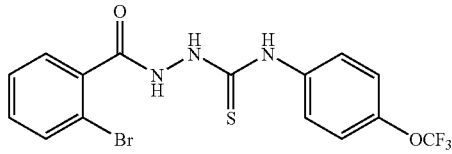

¹H-NMR (300 MHz, DMSO-d$_6$)
δ 7.36 (d, J=8.8 Hz, 2H), 7.38-7.46 (m, 2H), 7.61 (d, J=8.8 Hz, 2H), 7.71 (d, J=7.7 Hz, 1H), 7.78 (d, J=7.7 Hz, 1H), 9.80 (br s, 1H), 9.99 (s, 1H), 10.48 (s, 1H)

2-(3-Bromothiophene-2-carbonyl)-N-phenylhydrazinecarboxamide (Reference Compound 5-(12))

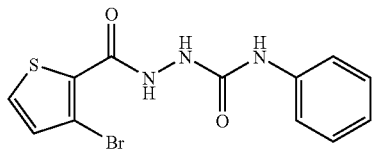

¹H-NMR (300 MHz, DMSO-d$_6$)
δ 10.00 (1H, s), 8.83 (1H, s), 8.29 (1H, s), 7.86 (1H, d, J=5.1 Hz), 7.46 (2H, d, J=7.8 Hz), 7.29-7.22 (3H, m), 6.90 (1H, t, J=7.2 Hz)

2-(3-Bromothiophene-2-carbonyl)-N-(4-chlorophenyl)hydrazinecarboxamide (Reference Compound 5-(13))

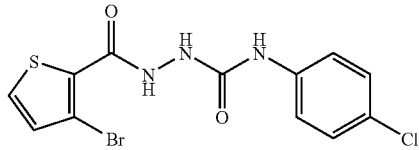

¹H-NMR (300 MHz, DMSO-d$_6$)
δ 10.00 (1H, s), 9.02 (1H, s), 8.39 (1H, s), 7.86 (1H, d, J=5.1 Hz), 7.50 (2H, d, J=8.8 Hz), 7.30 (2H, d, J=8.8 Hz), 7.23 (1H, d, J=5.1 Hz)

2-(3-Bromothiophene-2-carbonyl)-N-(4-trifluoromethoxyphenyl)hydrazinec arboxamide (Reference Compound 5-(14))

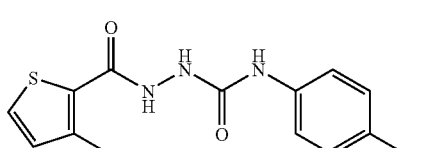

¹H-NMR (300 MHz, DMSO-d$_6$)
δ 10.02 (1H, s), 9.07 (1H, s), 8.42 (1H, s), 7.87 (1H, d, J=5.1 Hz), 7.58 (2H, d, J=9.0 Hz), 7.26 (2H, d, J=9.0 Hz), 7.24 (1H, d, J=5.1 Hz)

32

2-(3-Bromothiophene-2-carbonyl)-N-(3-trifluoromethylphenyl)hydrazinecarboxamide (Reference Compound 5-(15))

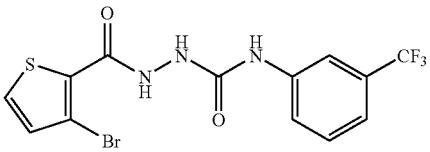

¹H-NMR (300 MHz, DMSO-d$_6$)
δ 10.00 (1H, s), 9.25 (1H, s), 8.53 (1H, s), 7.87 (1H, d, J=5.1 Hz), 7.68 (1H, d, J=8.3 Hz), 7.50 (1H, d, J=8.3 Hz), 7.30 (1H, d, J=7.5 Hz), 7.23 (1H, d, J=5.1 Hz)

2-(3-Bromothiophene-2-carbonyl)-N-phenylhydrazinecarbothioamide (Reference Compound 5-(16))

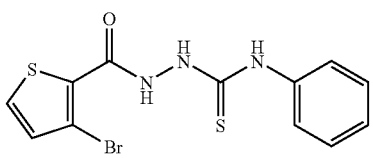

¹H-NMR (300 MHz, DMSO-d$_6$)
δ 10.52 (1H, s), 9.83 (2H, s), 7.88 (1H, d, J=5.1 Hz), 7.47 (2H, d, J=7.2 Hz), 7.33 (2H, d, J=7.2 Hz), 7.23 (1H, d, J=5.1 Hz), 7.15 (1H, t, J=7.2 Hz)

2-(3-Bromothiophene-2-carbonyl)-N-(4-chlorophenyl)hydrazinecarbothioam ide (Reference Compound 5-(17))

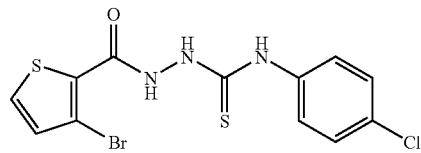

¹H-NMR (300 MHz, DMSO-d$_6$)
δ 10.25 (1H, s), 9.93 (2H, s), 7.88 (1H, d, J=5.1 Hz), 7.51 (2H, d, J=8.6 Hz) 7.39 (2H, d, J=8.6 Hz), 7.23 (1H, d, J=5.1 Hz)

2-(3-Bromothiophene-2-carbonyl)-N-(4-trifluoromethoxyphenyl)hydrazinec arbothioamide (Reference Compound 5-(18))

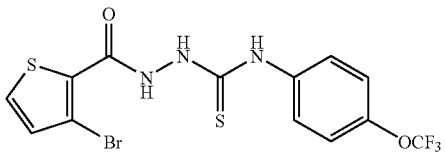

¹H-NMR (300 MHz, DMSO-d$_6$)
δ 10.27 (1H, s), 9.93 (2H, s), 7.83 (1H, d, J=5.2 Hz), 7.60 (2H, d, J=8.6 Hz), 7.34 (2H, d, J=8.6 Hz), 7.23 (1H, d, J=5.2 Hz)

2-(3-Bromothiophene-2-carbonyl)-N-(3-trifluoromethylphenyl)hydrazinecarbothioamide (Reference Compound 5-(19))

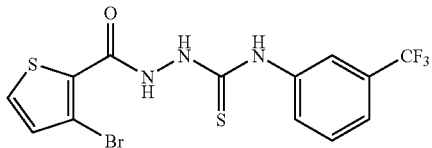

¹H-NMR (300 MHz, DMSO-d₆)
δ 10.27 (1H, s), 10.04 (2H, s), 7.90-7.82 (3H, m), 7.57-7.54 (2H, m), 7.24 (1H, d, J=5.1 Hz)

2-(2-Bromothiophene-3-carbonyl)-N-(4-chlorophenyl)hydrazinecarboxamide (Reference Compound 5-(20))

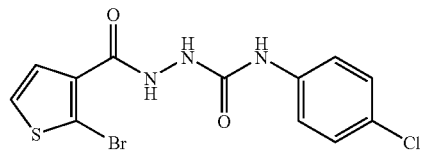

¹H-NMR (300 MHz, DMSO-d₆)
δ 10.09 (1H, s), 9.04 (1H, s), 8.36 (1H, s), 7.68 (1H, d, J=5.7 Hz), 7.51 (2H, d, J=8.9 Hz), 7.38 (1H, d, J=5.7 Hz), 7.31 (2H, d, J=8.9 Hz)

2-(2-Bromothiophene-3-carbonyl)-N-(3-trifluoromethylphenyl)hydrazinecarboxamide (Reference Compound 5-(21))

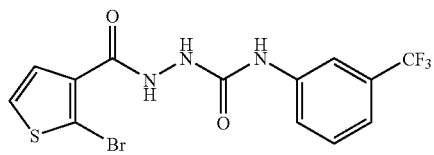

¹H-NMR (300 MHz, DMSO-d₆)
δ 10.11 (1H, s), 9.22 (1H, s), 8.47 (1H, s), 7.99 (1H, s), 7.71-7.64 (2H, m), 7.50 (1H, t, J=7.8 Hz), 7.40 (1H, d, J=5.7 Hz), 7.30 (1H, d, J=7.8 Hz)

1-(2-Bromobenzoyl)-4-(3-trifluoromethylphenyl)thiosemicarbazide (Reference Compound 5-(22))

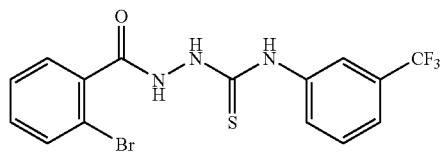

¹H-NMR (300 MHz, DMSO-d₆)
δ 10.50 (1H, s), 10.11 (1H, s), 9.90 (1H, br s), 8.00-7.40 (8H, m)

4-Phenyl-1-(2-(pyridin-4-yl)methoxybenzoyl)semicarbazide (Reference Compound 6-(1))

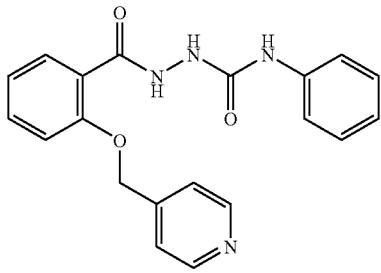

¹H-NMR (300 MHz, DMSO-d₆)
δ 5.33 (s, 2H), 6.97 (dd, J=7.5, 7.5 Hz, 1H), 7.08 (dd, J=7.5, 7.5 Hz, 1H), 7.16 (d, J=8.1 Hz, 1H), 7.24-7.29 (m, 2H), 7.44-7.50 (m, 3H), 7.55 (d, J=5.9 Hz, 2H), 7.68 (dd, J=7.5, 1.7 Hz, 1H), 8.32 (d, J=1.7 Hz, 1H), 8.55 (dd, J=4.6, 1.7 Hz, 2H), 8.76 (s, 1H), 9.94 (d, J=1.8 Hz, 1H)

4-(4-Chlorophenyl)-1-(2-(pyridin-4-yl)methoxybenzoyl)semicarbazide (Reference Compound 6-(2))

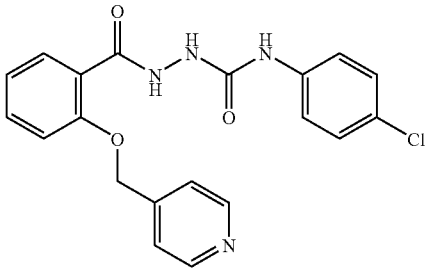

¹H-NMR (300 MHz, DMSO-d₆)
δ 5.33 (s, 2H), 7.07 (dd, J=7.5, 7.5 Hz, 1H), 7.15 (d, J=8.4 Hz, 1H), 7.31 (d, J=8.8 Hz, 2H), 7.45-7.55 (m, 5H), 7.68 (d, J=7.5 Hz, 1H), 8.42 (s, 1H), 8.55 (d, J=5.7 Hz, 2H), 8.94 (br s, 1H), 9.95 (s, 1H)

1-(2-(Pyridin-4-yl)methoxybenzoyl)-4-(3-trifluoromethylphenyl)semicarbazide (Reference Compound 6-(3))

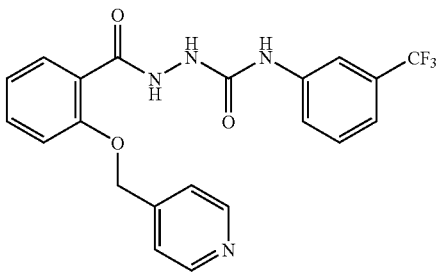

¹H-NMR (300 MHz, DMSO-d₆)
δ 5.34 (s, 2H), 7.08 (dd, J=7.5, 7.5 Hz, 1H), 7.16 (d, J=8.3 Hz, 1H), 7.31 (d, J=7.5 Hz, 1H), 7.45-7.56 (m, 4H), 7.65-7.70 (m, 2H), 8.01 (s, 1H), 8.50-8.60 (m, 3H), 9.18 (s, 1H), 9.96 (s, 1H)

4-Phenyl-1-(2-quinolin-4-yl)methoxybenzoyl)semi-carbazide (Reference Compound 6-(4))

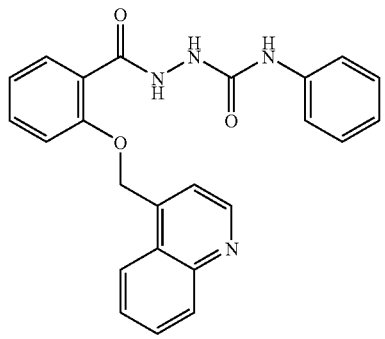

¹H-NMR (300 MHz, DMSO-d₆)
δ 5.82 (s, 2H), 6.97 (dd, J=7.5, 7.0 Hz, 1H), 7.11 (dd, J=7.5, 7.5 Hz, 1H), 7.27 (dd, J=8.1, 7.5 Hz, 2H), 7.38-7.54 (m, 4H), 7.68 (m, 2H), 7.81 (m, 1H), 7.87 (d, J=4.4 Hz, 1H), 8.07 (d, J=7.7 Hz, 1H), 8.27 (d, J=8.3 Hz, 1H), 8.30 (d, J=1.7 Hz, 1H), 8.77 (s, 1H), 8.87 (d, J=4.4 Hz, 1H), 9.97 (d, J=1.8 Hz, 1H)

4-Phenyl-1-(3-(pyridin-4-yl)methoxythiophene-2-carbonyl)semicarbazide (Reference Compound 6-(5))

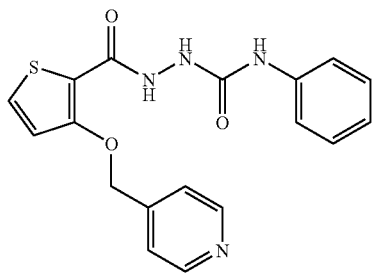

δ 5.45 (s, 2H), 6.96 (dd, J=7.0, 7.0 Hz, 1H), 7.10 (d, J=5.3 Hz, 1H), 7.26 (dd, J=7.3, 7.1 Hz, 2H), 7.45-7.53 (m, 4H), 7.76 (d, J=5.3 Hz, 1H), 8.26 (s, 1H), 8.58 (d, J=5.8 Hz, 2H), 8.86 (s, 1H), 9.20 (d, J=1.8 Hz, 1H)

4-(2-Chloro-5-trifluoromethylphenyl)-1-(2-(pyridin-4-yl)methoxybenzoyl)semicarbazide (Reference Compound 6-(6))

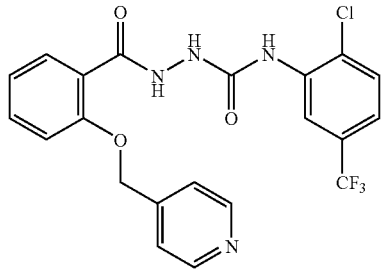

¹H-NMR (300 MHz, DMSO-d₆)
δ 5.33 (s, 2H), 7.08 (dd, J=7.5, 7.5 Hz, 1H), 7.18 (d, J=8.3 Hz, 1H), 7.39-7.41 (m, 1H), 7.50 (m, 1H), 7.54 (d, J=5.7 Hz, 2H), 7.63 (dd, J=7.5, 1.7 Hz, 1H), 7.71 (d, J=8.6 Hz, 1H), 8.54-8.59 (m, 4H), 9.25 (s, 1H), 10.16 (s, 1H)

4-(4-t-Butylphenyl)-1-(2-(pyridin-4-yl)methoxybenzoyl)semicarbazide (Reference Compound 6-(7))

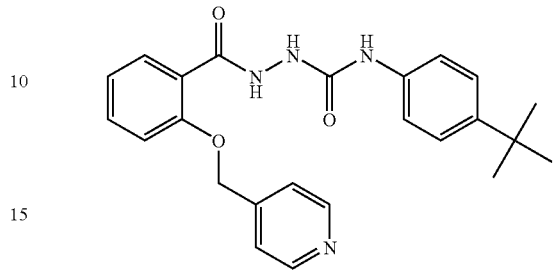

¹H-NMR (300 MHz, DMSO-d₆)
δ 1.26 (s, 9H), 5.33 (s, 2H), 7.08 (dd, J=7.5, 7.5 Hz, 1H), 7.16 (d, J=8.3 Hz, 1H), 7.27 (d, J=8.3 Hz, 2H), 7.36 (d, J=8.8 Hz, 2H), 7.45-7.50 (m, 1H), 7.54 (d, J=5.9 Hz, 2H), 7.67 (d, J=5.7 Hz, 1H), 8.26 (s, 1H), 8.55 (d, J=6.1 Hz, 2H), 8.67 (s, 1H), 9.93 (s, 1H)

1-(3-(Pyridin-4-yl)methoxythiophene-2-carbonyl)-4-(3-trifluoromethylphenyl)semicarbazide (Reference Compound 6-(8))

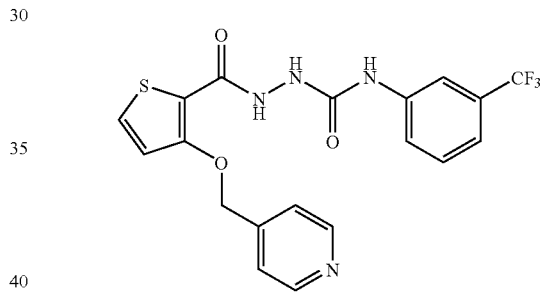

¹H-NMR (300 MHz, DMSO-d₆)
δ 5.45 (s, 2H), 7.10 (d, J=5.5 Hz, 1H), 7.30 (d, J=7.7 Hz, 1H), 7.47-7.52 (m, 3H), 7.77 (d, J=5.5 Hz, 2H), 7.99 (s, 1H), 8.49 (s, 1H), 8.57 (dd, J=4.4, 1.7 Hz, 2H), 9.25 (s, 2H)

2-(5-Bromo-2-(pyridin-4-yl)methoxybenzoyl)-N-phenylhydrazinecarboxamide (Reference Compound 6-(9))

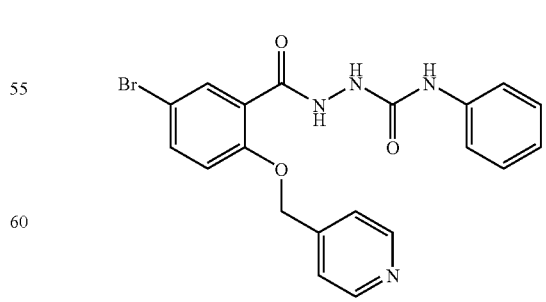

¹H-NMR (300 MHz, DMSO-d₆)
δ 5.33 (s, 2H), 6.97 (t, J=7.7 Hz, 1H), 7.14 (d, J=9.0 Hz, 1H), 7.27 (t, J=7.7 Hz, 2H), 7.46 (d, J=7.7 Hz, 2H), 7.52 (d,

J=4.6 Hz, 2H), 7.65 (m, 1H), 7.74 (br s, 1H), 8.35 (br s, 1H), 8.55 (d, J=4.6 Hz, 2H), 8.80 (br s, 1H), 10.05 (br s, 1H)

2-(5-Methoxy-2-(pyridin-4-yl)methoxybenzoyl)-N-phenylhydrazinecarboxamide (Reference Compound 6-(10))

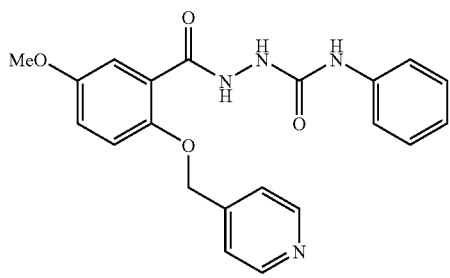

¹H-NMR (300 MHz, DMSO-d₆)
δ 3.75 (s, 3H), 5.28 (s, 2H), 6.96 (t, J=7.3 Hz, 1H), 7.05 (dd, J=9.0, 3.1 Hz, 1H), 7.10 (t, J=9.2 Hz, 1H), 7.23 (d, J=3.1 Hz, 1H), 7.27 (t, J=7.3 Hz, 2H), 7.46 (d, J=7.7 Hz, 2H), 7.53 (d, J=5.5 Hz, 2H), 8.33 (s, 1H), 8.55 (d, J=5.5 Hz, 2H), 8.79 (s, 1H), 9.96 (s, 1H)

N-Phenyl-2-(3-(pyridin-4-yl)methoxypicolinoyl)hydrazinecarboxamide (Reference Compound 6-(11))

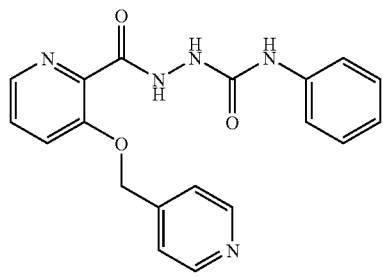

¹H-NMR (300 MHz, DMSO-d₆)
δ 5.32 (s, 2H), 6.81 (t, J=7.3 Hz, 1H), 7.27 (t, J=7.8 Hz, 2H), 7.46 (d, J=7.7 Hz, 2H), 7.53-7.57 (m, 3H), 7.67 (d, J=8.3 Hz, 1H), 8.23-8.32 (m, 2H), 8.55 (d, J=5.7 Hz, 2H), 8.73 (s, 1H), 10.19 (s, 1H)

2-((3-(pyridin-4-yl)methoxy)picolinoyl)-N-(3-trifluoromethylphenyl)hydrazinecarboxamide (Reference Compound 6-(12))

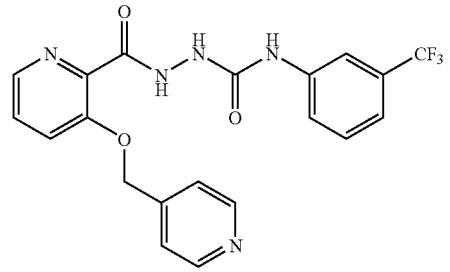

¹H-NMR (300 MHz, DMSO-d₆)
δ 5.32 (s, 2H), 7.30 (br d, J=8.1 Hz, 1H), 7.47-7.60 (m, 4H), 7.65-7.70 (m, 2H), 8.02 (br s, 1H), 8.24 (d, J=4.6 Hz, 1H), 8.50-8.60 (m, 3H), 9.16 (br s, 1H), 10.20 (s, 1H)

Reference Example 6

1-(2-(2-Acetamidopyridin-4-yl)methoxybenzoyl)-4-phenylsemicarbazide (Reference Compound 6-(13))

To a solution of 2-(2-acetamidopyridin-4-yl)methoxybenzoic acid (500 mg, 1.8 mmol; Reference Compound 3-(1)), 4-phenylsemicarbazide (265 mg, 1.8 mmol) and diisopropylethylamine (450 µL, 2.6 mmol) in N,N-dimethylformamide (5.0 mL) was added HCTU (940 mg, 2.3 mmol) under ice-cooling, and then the mixture was stirred for 8 hours at room temperature. The reaction solution was diluted with ethyl acetate (20 mL). To the solution was added a 0.1 M aqueous sodium hydroxide solution (20 mL). The ethyl acetate layer was washed with a saturated brine solution, dried over anhydrous sodium sulfate, and concentrated under a reduced pressure to dryness, and ethanol was added to the residue. The precipitated solid was filtered off and dried under a reduced pressure to give 250 mg (46%) of the titled compound as colorless solid.

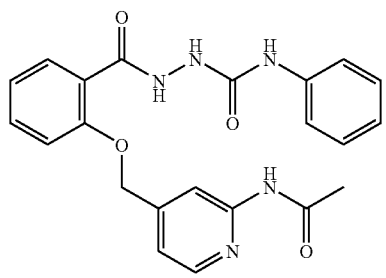

¹H-NMR (300 MHz, DMSO-d₆)
δ 2.09 (s, 3H), 5.33 (s, 2H), 6.96 (dd, J=7.3, 7.3 Hz, 1H), 7.07 (m, 1H), 7.16 (d, J=8.4 Hz, 1H), 7.22-7.29 (m, 3H), 7.42-7.49 (m, 3H), 7.69 (dd, J=7.3, 1.7 Hz, 1H), 8.17 (s, 1H), 8.26 (d, J=5.0 Hz, 1H), 8.28 (d, J=2.0 Hz, 1H), 8.74 (br s, 1H), 9.90 (d, J=2.0 Hz, 1H), 10.52 (s, 1H)

The following Reference Compound 6-(14) to (31) were obtained by a production method similar to that of Reference Compound 6-(13) using compounds selected from Reference Compounds 3-(2), 4-(1), 4-(2), 2-(2-t-butoxycarbonylaminopyridin-4-yl) methylthionicotinic acid (CAS#864460-87-7; WO2005/085201), 2-(pyridin-4-yl) methylthionicotinic acid (CAS#312921-84-9; WO2004/078723), 2-(2-quinolin-4-yl) methylthionicotinic acid (CAS#909007-26-7; WO2006/093253) and commercially available compounds.

1-(2-(2-t-Butoxycarbonylaminopyridin-4-yl)methylthiopyridine-3-carbonyl)-4-phenylsemicarbazide (Reference Compound 6-(14))

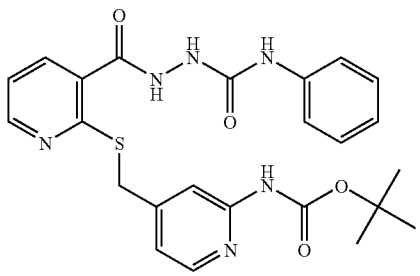

¹H-NMR (300 MHz, DMSO-d₆)
δ 1.43 (s, 9H), 4.28 (s, 2H), 6.83 (t, J=7.3 Hz, 1H), 7.08-7.23 (m, 7H), 7.95 (s, 1H), 8.15-8.25 (m, 3H), 8.35 (m, 1H), 8.65 (s, 1H), 9.76 (s, 1H)

1-(2-(2-t-Butoxycarbonylaminopyridin-4-yl)methylthiopyridine-3-carbonyl)-4-(4-chlorophenyl)semicarbazide (Reference Compound 6-(15))

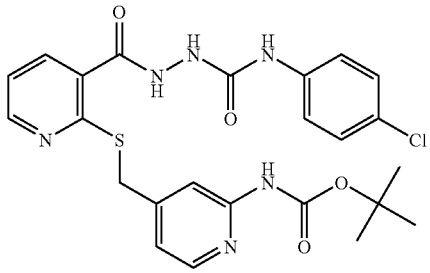

¹H-NMR (300 MHz, DMSO-d₆)

δ 1.44 (s, 9H), 4.32 (s, 2H), 7.10 (m, 1H), 7.14-7.24 (m, 1H), 7.29 (d, J=8.8 Hz, 2H), 7.54 (d, J=8.8 Hz, 2H), 7.94 (m, 1H), 8.04-8.28 (m, 2H), 8.45 (br s, 1H), 8.65 (m, 1H), 9.25 (br s, 1H), 9.81 (br s, 1H)

1-(2-(2-t-Butoxycarbonylaminopyridin-4-yl)methylthiopyridine-3-carbonyl)-4-(3-trifluoromethylphenyl)semicarbazide (Reference Compound 6-(16))

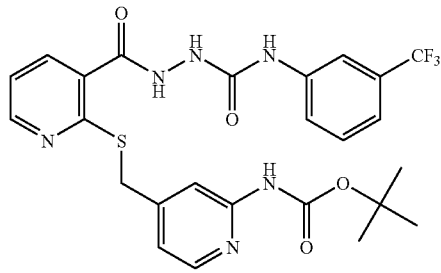

¹H-NMR (300 MHz, DMSO-d₆)

δ 1.46 (s, 9H), 4.35 (s, 2H), 7.03 (br d, J=5.0 Hz, 1H), 7.26-7.33 (m, 2H), 7.49 (t, J=8.3 Hz, 1H), 7.68 (m, 1H), 7.87 (s, 1H), 7.98 (br s, 1H), 8.05 (m, 1H), 8.10 (d, J=5.1 Hz, 1H), 8.51 (s, 1H), 8.60 (br d, J=5.0 Hz, 1H), 9.20 (s, 1H), 9.69 (s, 1H), 10.65 (s, 1H)

4-Phenyl-1-(2-(pyridin-4-yl)methylthiopyridine-3-carbonyl)semicarbazide (Reference Compound 6-(17))

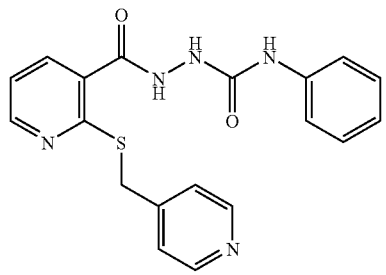

¹H-NMR (300 MHz, DMSO-d₆)

δ 4.36 (s, 2H), 6.96 (t, J=7.3 Hz, 1H), 7.26 (t, J=7.3 Hz, 2H), 7.29 (d, J=7.5 Hz, 1H), 7.40 (d, J=5.9 Hz, 2H), 7.45 (d, J=7.3 Hz, 2H), 8.02 (d, J=7.2 Hz, 1H), 8.27 (br s, 1H), 8.46 (d, J=5.9 Hz, 2H), 8.59 (dd, J=4.8, 1.7 Hz, 1H), 8.81 (br s, 1H), 10.32 (s, 1H)

4-(4-Chlorophenyl)-1-(2-(pyridin-4-yl)methylthiopyridine-3-carbonyl)semicarbazide (Reference Compound 6-(18))

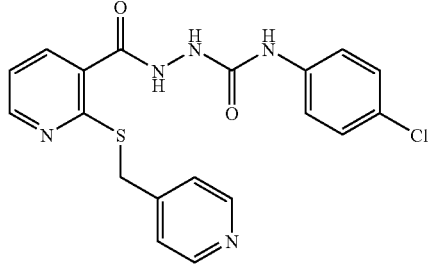

¹H-NMR (300 MHz, DMSO-d₆)

δ 4.39 (s, 2H), 7.28 (dd, J=7.7, 4.8 Hz, 1H), 7.30 (d, J=8.8 Hz, 2H), 7.39 (d, J=5.9 Hz, 2H), 7.50 (d, J=8.8 Hz, 2H), 8.02 (m, 1H), 8.36 (br s, 1H), 8.45 (d, J=5.9 Hz, 2H), 8.59 (dd, J=4.8, 1.5 Hz, 1H), 8.97 (br s, 1H), 10.32 (br s, 1H)

1-(2-(Pyridin-4-yl)methylthiopyridine-3-carbonyl)-4-(3-trifluoromethylphenyl)semicarbazide (Reference Compound 6-(19))

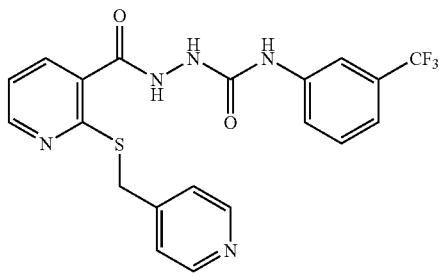

¹H-NMR (300 MHz, DMSO-d₆)

δ 4.39 (s, 2H), 7.26-7.32 (m, 2H), 7.40 (d, J=5.9 Hz, 2H), 7.49 (t, J=7.5 Hz, 1H), 7.69 (t, J=7.9 Hz, 1H), 7.97 (s, 1H), 8.05 (m, 1H), 8.45 (d, J=5.9 Hz, 2H), 8.52 (s, 1H), 8.60 (m, 1H), 9.26 (s, 1H), 10.35 (s, 1H)

4-Phenyl-1-(2-(quinolin-4-yl)methylthiopyridine-3-carbonyl)semicarbazide (Reference Compound 6-(20))

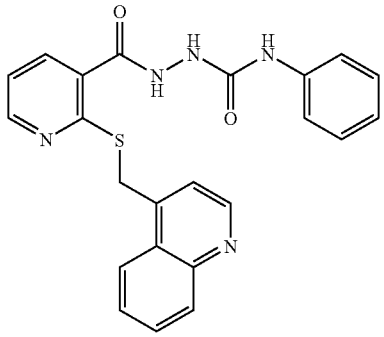

¹H-NMR (300 MHz, DMSO-d₆)

δ 4.91 (s, 2H), 6.94 (t, J=7.3 Hz, 1H), 7.23 (t, J=7.3 Hz, 2H), 7.30 (dd, J=7.7, 5.0 Hz, 1H), 7.42 (d, J=7.3 Hz, 2H), 7.62

(d, J=4.2 Hz, 1H), 7.66 (d, J=8.3 Hz, 1H), 7.78 (d, J=8.3 Hz, 1H), 8.22-8.28 (m, 2H), 8.65 (d, J=4.8 Hz, 1H), 8.77 (br s, 1H), 8.79 (d, J=4.2 Hz, 1H), 10.32 (s, 1H)

4-(4-Chlorophenyl)-1-(2-(quinolin-4-yl)methylthiopyridine-3-carbonyl)semicarbazide (Reference. Compound 6-(21))

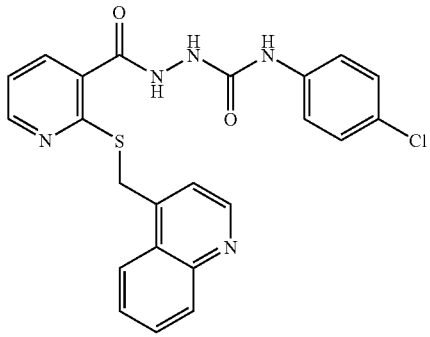

$^1$H-NMR (300 MHz, DMSO-d$_6$)
δ 4.91 (s, 2H), 7.25-7.34 (m, 3H), 7.46 (t, J=8.8 Hz, 2H), 7.60-7.70 (m, 2H), 7.78 (m, 1H), 8.01-8.07 (m, 2H), 8.25 (d, J=7.9 Hz, 1H), 8.33 (s, 1H), 8.64 (m, 1H), 8.79 (d, J=4.4 Hz, 1H), 8.94 (br s, 1H), 10.32 (br s, 1H)

1-(2-(Quinolin-4-yl)methylthiopyridine-3-carbonyl)-4-(3-trifluoromethylphenyl)semicarbazide (Reference Compound 6-(22))

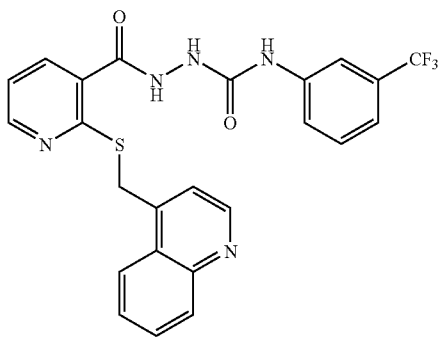

$^1$H-NMR (300 MHz, DMSO-d$_6$)
δ 4.91 (s, 2H), 7.26-7.34 (m, 2H), 7.47 (t, J=7.9 Hz, 1H), 7.54 (dd, J=7.9, 4.6 Hz, 1H), 7.60-7.70 (m, 2H), 7.77 (m, 1H), 7.95 (s, 1H), 8.00-8.14 (m, 3H), 8.25 (d, J=7.9 Hz, 1H), 8.47 (s, 1H), 8.80 (d, J=5.1 Hz, 1H), 9.22 (br s, 1H), 10.35 (br s, 1H)

1-(2-(2-Acetamidopyridin-4-yl)methylthiopyridine-3-carbonyl)-4-phenylsemicarbazide (Reference Compound 6-(23))

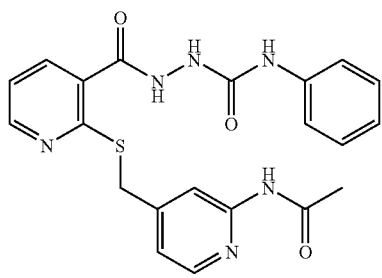

$^1$H-NMR (300 MHz, DMSO-d$_6$)
δ 2.06 (s, 3H), 4.36 (s, 2H), 6.96 (t, J=7.3 Hz, 1H), 7.10 (d, J=5.1 Hz, 1H), 7.21-7.31 (m, 3H), 7.45 (d, J=8.3 Hz, 2H), 8.03 (d, J=7.0 Hz, 1H), 8.14-8.20 (m, 2H), 8.29 (s, 1H), 8.58 (d, J=4.8 Hz, 1H), 8.85 (s, 1H), 10.32 (s, 1H), 10.41 (s, 1H)

4-(4-Chlorophenyl)-1-(2-(2-acetamidopyridin-4-yl)methylthiopyridine-3-carbonyl)semicarbazide (Reference Compound 6-(24))

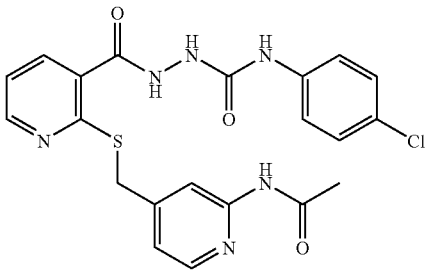

$^1$H-NMR (300 MHz, DMSO-d$_6$)
δ 2.07 (s, 3H), 4.36 (s, 2H), 7.09 (br d, J=6.4 Hz, 1H), 7.25-7.32 (m, 3H), 7.50 (d, J=8.8 Hz, 2H), 8.02 (br d, J=6.8 Hz, 1H), 8.14-8.18 (m, 2H), 8.37 (br s, 1H), 8.58 (dd, J=5.0, 1.8 Hz, 1H), 8.96 (br s, 1H), 10.32 (s, 1H), 10.40 (s, 1H)

1-(2-(2-Acetamidopyridin-4-yl)methylthiopyridine-3-carbonyl)-4-(3-trifluoromethylphenyl)semicarbazide (Reference Compound 6-(25))

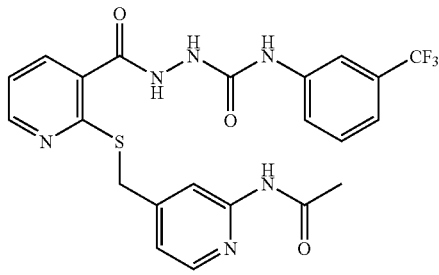

$^1$H-NMR (300 MHz, DMSO-d$_6$)
δ 2.06 (s, 3H), 4.37 (s, 2H), 7.09 (br d, J=5.1 Hz, 1H), 7.26-7.32 (m, 2H), 7.49 (t, J=7.9 Hz, 1H), 7.69 (br d, J=8.6 Hz, 1H), 7.97 (br s, 1H), 8.05 (m, 1H), 8.14-8.20 (m, 2H), 8.51 (s, 1H), 8.59 (m, 1H), 9.21 (br s, 1H), 10.34 (s, 1H), 10.40 (s, 1H)

1-(2-(2-Methylaminocarbonylpyridin-4-yl)methylthiopyridine-3-carbonyl)-4-phenylsemicarbazide (Reference Compound 6-(26))

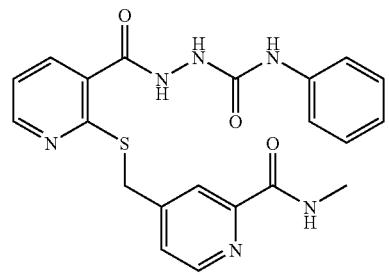

$^1$H-NMR (300 MHz, DMSO-d$_6$)
δ 2.79 (d, J=4.8 Hz, 3H), 4.48 (s, 2H), 6.96 (t, J=7.3 Hz, 1H), 7.22-7.32 (m, 3H), 7.46 (d, J=7.5 Hz, 2H), 7.60 (dd, J=5.1, 1.7 Hz, 1H), 8.00-8.08 (m, 2H), 8.28 (br s, 1H), 8.51 (d,

J=5.1 Hz, 1H), 8.57 (dd, J=4.8, 1.5 Hz, 1H), 8.72 (q, J=4.8 Hz, 1H), 8.82 (br s, 1H), 10.33 (s, 1H)

4-(4-Chlorophenyl)-1-(2-(2-methylaminocarbonylpyridin-4-yl)methylthiopyridine-3-carbonyl)semicarbazide (Reference Compound 6-(27))

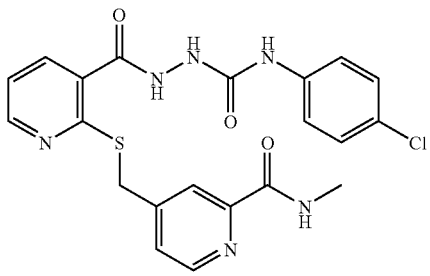

$^1$H-NMR (300 MHz, DMSO-d$_6$)

δ 2.80 (d, J=4.8 Hz, 3H), 4.48 (s, 2H), 7.25-7.34 (m, 3H), 7.50 (d, J=8.8 Hz, 2H), 7.60 (dd, J=5.0, 1.7 Hz, 1H), 8.00-8.08 (m, 2H), 8.38 (s, 1H), 8.51 (d, J=4.8 Hz, 1H), 8.58 (dd, J=4.8, 1.7 Hz, 1H), 8.73 (q, J=4.8 Hz, 1H), 8.99 (br s, 1H), 10.34 (s, 1H)

1-(2-(2-Methylaminocarbonylpyridin-4-yl)methylthiopyridine-3-carbonyl)-4-(3-trifluoromethylphenyl)semicarbazide (Reference Compound 6-(28))

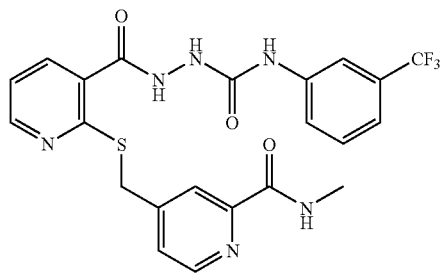

$^1$H-NMR (300 MHz, DMSO-d$_6$)

δ 2.79 (d, J=4.8 Hz, 3H), 4.48 (s, 2H), 7.26-7.34 (m, 2H), 7.50 (d, J=7.9 Hz, 1H), 7.60 (m, 1H), 7.70 (m, 1H), 7.98 (br s, 1H), 8.04-8.10 (m, 2H), 8.50 (d, J=5.0 Hz, 1H), 8.53 (br s, 1H), 8.58 (m, 1H), 8.73 (q, J=4.8 Hz, 1H), 9.23 (br s, 1H), 10.37 (s, 1H)

1-(2-(2-Acetamidopyridin-4-yl)methylthiopyridine-3-carbonyl)-4-(4-trifluoromethoxyphenyl)semicarbazide (Reference Compound 6-(29))

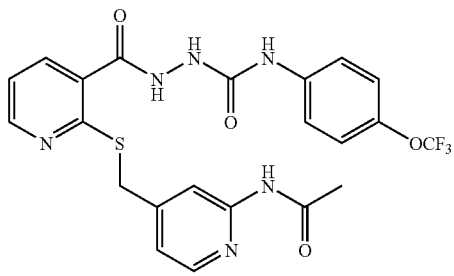

$^1$H-NMR (300 MHz, DMSO-d$_6$)

δ 2.06 (s, 3H), 4.36 (s, 2H), 7.10 (d, J=5.1 Hz, 1H), 7.23-7.32 (m, 3H), 7.57 (d, J=9.0 Hz, 2H), 8.03 (d, J=7.3 Hz, 1H), 8.14-8.20 (m, 2H), 8.40 (br s, 1H), 8.57-8.61 (m, 1H), 9.03 (s, 1H), 10.33 (s, 1H), 10.41 (s, 1H)

2-(3-(2-Acetamidopyridin-4-yl)methoxythiophene-2-carbonyl)-N-phenylhydrazinecarboxamide (Reference Compound 6-(30))

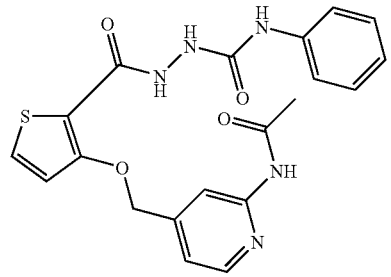

$^1$H-NMR (300 MHz, DMSO-d$_6$)

δ 2.08 (s, 3H), 5.44 (s, 2H), 6.96 (t, J=7.3 Hz, 1H), 7.08 (d, J=5.5 Hz, 1H), 7.20-7.30 (m, 3H), 7.46 (d, J=7.7 Hz, 2H), 7.76 (d, J=5.5 Hz, 1H), 8.17 (br s, 1H), 8.24 (br s, 1H), 8.29 (d, J=5.1 Hz, 1H), 8.85 (br s, 1H), 9.16 (br s, 1H), 10.54 (s, 1H)

2-(3-(2-Acetamidopyridin-4-yl)methoxythiophene-2-carbonyl)-N-(3-trifluoromethylphenyl)hydrazinecarboxamide (Reference Compound 6-(31)

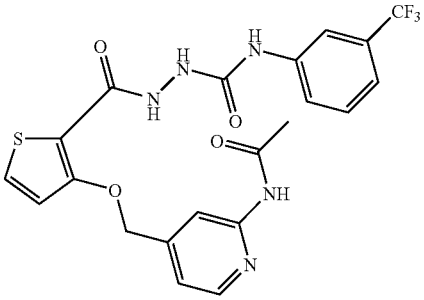

$^1$H-NMR (300 MHz, DMSO-d$_6$)

δ 2.07 (s, 3H), 5.44 (s, 2H), 7.08 (d, J=5.5 Hz, 1H), 7.22 (d, J=5.0 Hz, 1H), 7.30 (d, J=8.3 Hz, 1H), 7.49 (t, J=8.3 Hz, 1H), 7.70 (m, 1H), 7.77 (d, J=5.5 Hz, 1H), 7.98 (br s, 1H), 8.17 (br s, 1H), 8.29 (d, J=5.0 Hz, 1H), 8.46 (br s, 1H), 9.20 (br s, 1H), 9.24 (br s, 1H), 10.55 (s, 1H)

Reference Example 7

5-(2-Bromophenyl)-N-phenyl-1,3,4-oxadiazol-2-amine (Reference Compound 7-(1))

To a solution of 1-(2-bromobenzoyl)-4-phenylsemicarbazide (330 mg, 0.98 mmol; Reference Compound 5-(1)), triphenylphosphine (390 mg, 1.5 mmol) and triethylamine (0.20 mL, 9.7 mmol) in methylene chloride (30 mL) were added carbon tetrachloride (2.5 mL, 1.4 mmol) and tetrahydrofuran (5 mL) under ice-cooling. The mixture was refluxed for 2 hours and then cooled to room temperature. Ethyl acetate (20 mL) was added thereto and the ethyl acetate solution was washed with a saturated brine solution (20 mL) twice, dried over anhydrous sodium sulfate, and concentrated under a reduced pressure to dryness. The residue was purified with a silica gel column chromatography (hexane/ethyl acetate) to give 260 mg (82%) of the titled compound as a colorless solid.

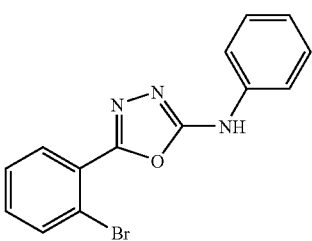

¹H-NMR (300 MHz, DMSO-d₆) δ 7.03 (t, J=7.3 Hz, 1H), 7.38 (dd, J=7.9, 7.3 Hz, 1H), 7.49-7.64 (m, 4H), 7.86 (d, J=7.9 Hz, 2H), 11.00 (br s, 1H)

The following Reference Compound 7-(2) to (11) were obtained by a production method similar to that of Reference Compound 7-(1) using compounds selected from Reference Compounds 5-(2) to (5), 5-(12) to (15), 5-(20) and 5-(21) and commercially available compounds.

5-(2-Bromophenyl)-N-(4-chlorophenyl)-1,3,4-oxa-diazol-2-amine (Reference Compound 7-(2))

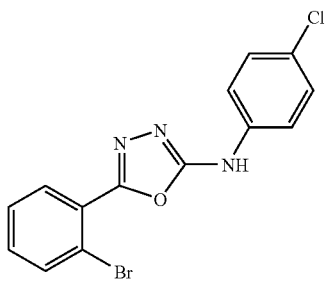

¹H-NMR (300 MHz, DMSO-d₆)

δ 7.44 (d, J=9.0 Hz, 2H), 7.48-7.64 (m, 3H), 7.65 (d, J=9.0 Hz, 2H), 7.87 (m, 1H), 10.90 (s, 1H)

5-(2-Bromophenyl)-N-(3-trifluoromethylphenyl)-1,3,4-oxadiazol-2-amine (Reference Compound 7-(3))

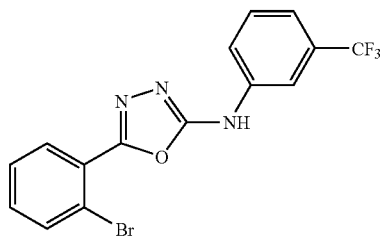

¹H-NMR (300 MHz, DMSO-d₆)

δ 7.39 (d, J=8.1 Hz, 1H), 7.53 (td, J=7.7, 1.8 Hz, 1H), 7.58-7.66 (m, 2H), 7.80-7.90 (m, 3H), 8.10 (s, 1H), 11.16 (s, 1H)

5-(2-Bromophenyl)-N-(4-t-butylphenyl)-1,3,4-oxa-diazol-2-amine (Reference Compound 7-(4))

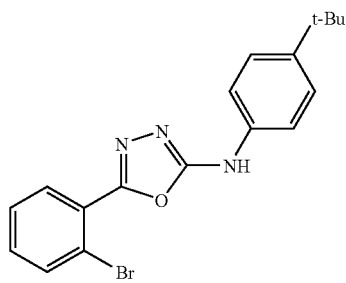

¹H-NMR (300 MHz, DMSO-d₆)

δ 1.28 (s, 9H), 7.27-7.45 (m, 6H), 7.69 (d, J=8.1 Hz, 1H), 8.07 (dd, J=7.7, 1.7 Hz, 1H), 10.90 (br s, 1H)

5-(2-Bromophenyl)-N-(4-trifluoromethoxyphenyl)-1,3,4-oxadiazol-2-amine (Reference Compound 7-(5))

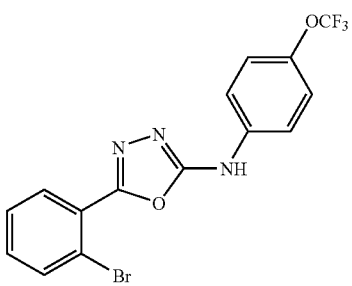

¹H-NMR (300 MHz, DMSO-d₆)

δ 7.40 (d, J=8.8 Hz, 2H), 7.49-7.63 (m, 2H), 7.72 (d, J=8.8 Hz, 2H), 7.84-7.90 (m, 2H), 10.97 (s, 1H)

5-(3-Bromothiophen-2-yl)-N-phenyl-1,3,4-oxadia-zol-2-amine (Reference Compound 7-(6))

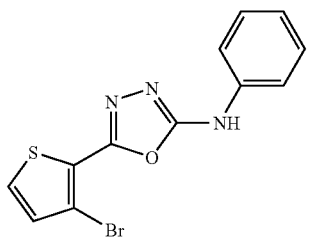

¹H-NMR (300 MHz, DMSO-d₆)

δ 10.78 (1H, s), 7.92 (1H, d, J=5.4 Hz), 7.61 (2H, d, J=8.0 Hz), 7.37-7.33 (3H, m), 7.03 (1H, t, J=7.2 Hz)

5-(3-Bromothiophen-2-yl)-N-(4-chlorophenyl)-1,3,4-oxadiazol-2-amine (Reference Compound 7-(7))

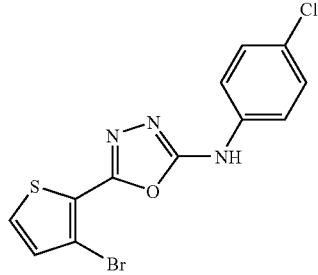

¹H-NMR (300 MHz, DMSO-d₆)

δ 10.95 (1H, s), 7.90 (1H, d, J=5.2 Hz), 7.63 (2H, d, J=8.8 Hz), 7.43 (2H, d, J=8.8 Hz), 7.33 (1H, d, J=5.2 Hz)

5-(3-Bromothiophen-2-yl)-N-(4-trifluoromethoxyphenyl)-1,3,4-oxadiazol-2-amine (Reference Compound 7-(8))

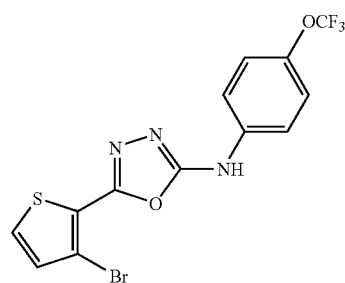

¹H-NMR (300 MHz, DMSO-d₆) δ 11.02 (1H, s), 7.93 (1H, d, J=5.2 Hz), 7.71 (2H, d, J=8.8 Hz), 7.40 (2H, d, J=8.8 Hz), 7.34 (1H, d, J=5.2 Hz)

5-(3-Bromothiophen-2-yl)-N-(3-trifluoromethylphenyl)-1,3,4-oxadiazol-2-amine (Reference Compound 7-(9))

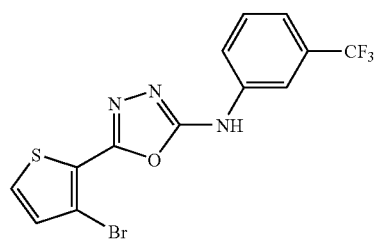

¹H-NMR (300 MHz, DMSO-d₆)

δ 11.20 (1H, s), 8.08 (1H, s), 7.94 (1H, d, J=5.2 Hz), 7.79 (1H, d, J=7.9 Hz), 7.62 (1H, t, J=7.9 Hz), 7.38 (1H, d, J=7.9 Hz), 7.34 (1H, d, J=5.2 Hz)

5-(2-Bromothiophen-3-yl)-N-(4-chlorophenyl)-1,3,4-thiadiazol-2-amine (Reference Compound 7-(10))

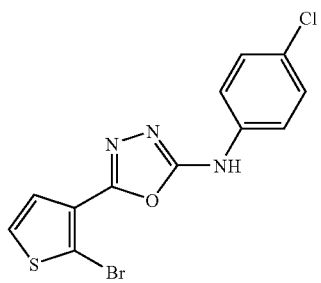

¹H-NMR (300 MHz, DMSO-d₆)

δ 7.81 (1H, d, J=5.7 Hz), 7.64 (2H, d, J=9.0 Hz), 7.46-7.40 (3H, m)

5-(2-Bromothiophen-3-yl)-N-(3-trifluoromethylphenyl)-1,3,4-thiadiazol-2-amine (Reference Compound 7-(11))

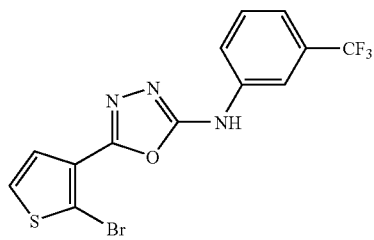

¹H-NMR (300 MHz, DMSO-d₆)

δ 11.10 (1H, s), 8.08 (1H, s), 7.82 (1H, d, J=6.0 Hz), 7.65-7.58 (2H, m), 7.40 (1H, d, J=5.7 Hz), 7.36 (1H, d, J=7.6 Hz)

Reference Example 8

5-(2-Bromophenyl)-N-phenyl-1,3,4-thiadiazol-2-amine (Reference Compound 7-(12))

To a solution of 1-(2-bromobenzoyl)-4-phenylthiosemicarbazide (250 mg, 0.71 mmol; Reference Compound 5-(6)) in ethanol (2.5 mL) was added concentrated sulfuric acid (0.5 mL) at room temperature, and then the mixture was refluxed for 30 minutes. The reaction solution was poured into ice water and the precipitated solid was filtered off. The solid was dried under a reduced pressure at 60° C. to give 210 mg (87%) of the titled compound as a colorless solid.

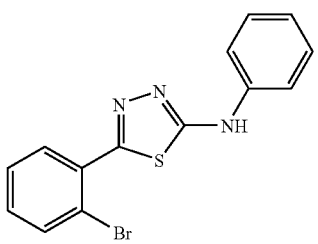

¹H-NMR (300 MHz, DMSO-d₆)

δ 7.04 (t, J=7.3 Hz, 1H), 7.32-7.62 (m, 4H), 7.66 (d, J=8.1 Hz, 2H), 7.83 (d, J=8.1 Hz, 1H), 7.95 (dd, J=7.9, 1.8 Hz, 1H), 10.57 (s, 1H)

The following Reference Compound 7-(13) to (22) were obtained by a production method similar to that of Reference Compound 7-(12) using compounds selected from Reference Compounds 5-(7) to (11), 5-(16) to (19) and 5-(22) and commercially available compounds.

5-(2-Bromophenyl)-N-(4-chloropheny)-1,3,4-thiadiazol-2-amine (Reference Compound 7-(13))

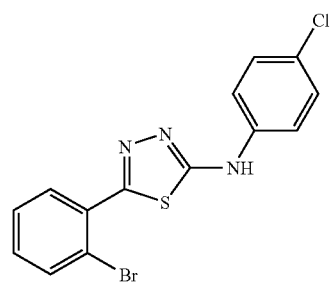

¹H-NMR (300 MHz, DMSO-d₆)

δ 7.32-7.68 (m, 4H), 7.72 (d, J=8.8 Hz, 2H), 7.83 (dd, J=8.1, 1.1 Hz, 1H), 7.95 (dd, J=7.7, 1.7 Hz, 1H), 10.71 (s, 1H)

5-(2-Bromophenyl)-N-(3-chlorophenyl)-1,3,4-thiadiazol-2-amine (Reference Compound 7-(14))

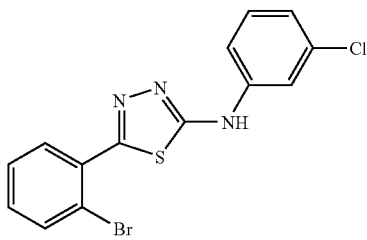

¹H-NMR (300 MHz, DMSO-d₆)

δ 7.09 (d, J=7.7 Hz, 1H), 7.40 (t, J=7.9 Hz, 1H), 7.44-7.52 (m, 2H), 7.57 (t, J=7.5 Hz, 1H), 7.84 (d, J=7.9 Hz, 1H), 7.94-7.99 (m, 2H), 10.79 (s, 1H)

5-(2-Bromophenyl)-N-(4-trifluoromethylphenyl)-1,3,4-thiadiazol-2-amine(Reference Compound 7-(15))

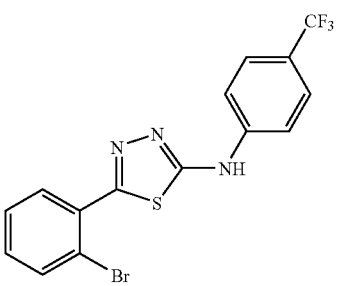

¹H-NMR (300 MHz, DMSO-d₆)

δ 7.48 (td, J=7.5, 1.8 Hz, 1H), 7.57 (td, J=7.5, 1.3 Hz, 1H), 7.74 (d, J=8.6 Hz, 2H), 7.85 (dd, J=7.5, 1.3 Hz, 1H), 7.89 (d, J=8.6 Hz, 2H), 7.97 (dd, J=7.5, 1.8 Hz, 1H), 10.99 (s, 1H)

5-(2-Bromophenyl)-N-(4-t-butylphenyl)-1,3,4-thiadiazol-2-amine (Reference Compound 7-(16))

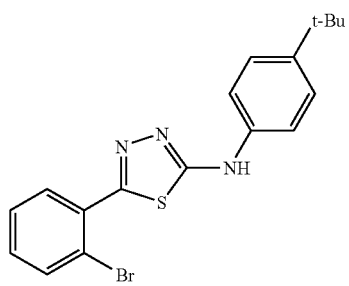

¹H-NMR (300 MHz, DMSO-d₆)

δ 1.33 (s, 9H), 7.27-7.45 (m, 6H), 7.69 (d, J=8.1 Hz, 1H), 8.07 (dd, J=7.7, 1.7 Hz, 1H), 10.61 (s, 1H)

5-(2-Bromophenyl)-N-(3-trifluoromethylphenyl)-1,3,4-thiadiazol-2-amine (Reference Compound 7-(17))

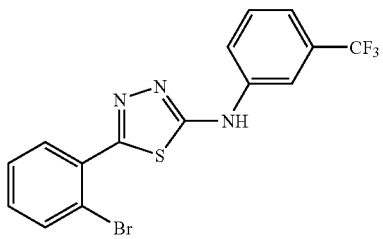

¹H-NMR (300 MHz, DMSO-d₆)

δ 7.38 (m, 1H), 7.48 (m, 1H), 7.53-7.65 (m, 2H), 7.78-7.88 (m, 2H), 7.98 (m, 1H), 8.27 (br s, 1H), 10.94 (s, 1H)

5-(2-Bromophenyl)-N-(4-trifluoromethoxyphenyl)-1,3,4-thiadiazol-2-amine (Reference Compound 7-(18))

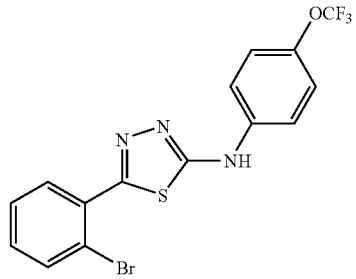

¹H-NMR (300 MHz, DMSO-d₆)

δ 7.39 (d, J=9.0 Hz, 2H), 7.47 (m, 1H), 7.56 (t, J=7.7 Hz, 1H), 7.79 (d, J=9.0 Hz, 2H), 7.84 (d, J=7.7 Hz, 1H), 7.96 (d, J=7.7 Hz, 1H), 10.77 (s, 1H)

5-(3-Bromothiophen-2-yl)-N-phenyl-1,3,4-thiadiazol-2-amine (Reference Compound 7-(19))

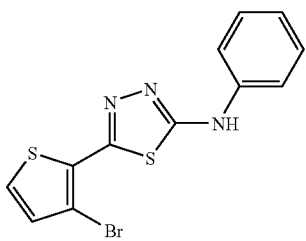

¹H-NMR (300 MHz, DMSO-d₆)

δ 10.62 (1H, s), 7.82 (1H, d, J=5.4 Hz), 7.64 (2H, d, J=7.8 Hz), 7.38 (2H, d, J=7.8 Hz), 7.29 (1H, d, J=5.4 Hz), 7.04 (1H, t, J=7.2 Hz)

5-(3-Bromothiophen-2-yl)-N-(4-chlorophenyl)-1,3,4-thiadiazol-2-amine (Reference Compound 7-(20))

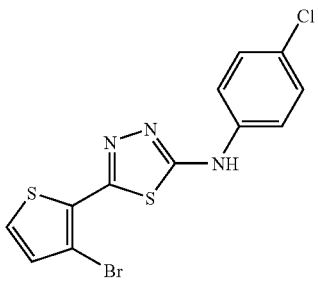

¹H-NMR (300 MHz, DMSO-d₆)

δ 10.95 (1H, s), 7.83 (1H, d, J=5.4 Hz), 7.71 (2H, d, J=8.8 Hz), 7.42 (2H, d, J=8.8 Hz), 7.30 (1H, d, J=5.4 Hz)

5-(3-Bromothiophen-2-yl)-N-(4-trifluoromethoxyphenyl)-1,3,4-thiadiazol-2-amine (Reference Compound 7-(21))

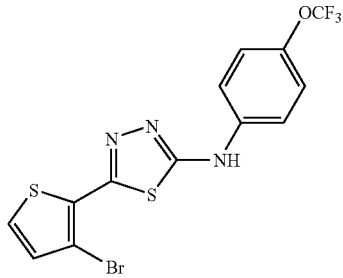

¹H-NMR (300 MHz, DMSO-d₆)

δ 10.79 (1H, s), 7.83 (1H, d, J=5.3 Hz), 7.76 (2H, d, J=8.9 Hz), 7.39 (2H, d, J=8.9 Hz), 7.30 (1H, d, J=5.3 Hz)

5-(3-Bromothiophen-2-yl)-N-(3-trifluoromethylphenyl)-1,3,4-thiadiazol-2-amine (Reference Compound 7-(22))

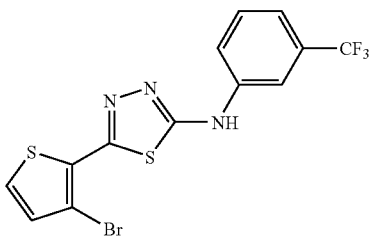

¹H-NMR (300 MHz, DMSO-d₆)

δ 8.24 (1H, s), 7.84 (1H, d, J=5.3 Hz), 7.77 (1H, d, J=8.0 Hz), 7.59 (1H, t, J=8.0 Hz), 7.36 (1H, d, J=8.0 Hz), 7.31 (1H, d, J=5.3 Hz)

Reference Example 9

3-(2-(5-Phenylamino-1,3,4-oxadiazol-2-yl)phenylthio)propanoic acid 2-ethylhexyl (Reference Compound 8-(1))

A vessel containing 5-(2-bromophenyl)-N-phenyl-1,3,4-oxadiazol-2-amine (2.9 g, 9.3 mmol; Reference Compound 7-(1)), bis(dibenzylideneacetone) palladium (130 mg, 0.23 mmol) and Xantphos (260 mg, 0.46 mmol) was replaced with nitrogen gas. To the vessel were added dioxane (60 mL), diisopropylethylamine (5.0 mL, 29 mmol) and 2-ethylhexyl 3-mercaptopropionate (4.2 mL, 19 mmol) successively at room temperature, and then the mixture was refluxed for 3 hours. The reaction solution was cooled to room temperature and concentrated under a reduced pressure. The residue was diluted with ethyl acetate (100 mL) and the ethyl acetate solution was washed with a saturated brine solution (30 mL), dried over anhydrous sodium sulfate and concentrated under a reduced pressure to dryness. The residue was purified with a silica gel column chromatography (hexane/ethyl acetate) to give 2.8 g (97%) of the titled compound as a colorless solid.

53

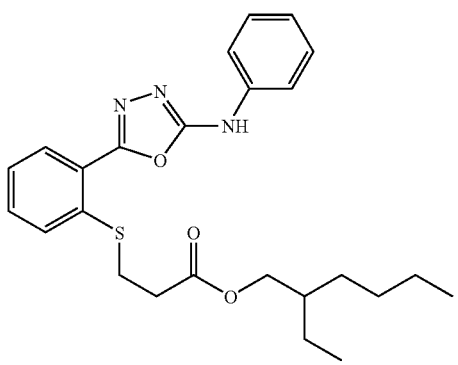

¹H-NMR (300 MHz, DMSO-d₆)

δ 0.75-0.83 (m, 6H), 1.19-1.28 (m, 8H), 1.49 (m, 1H), 2.67 (t, J=6.8 Hz, 2H), 3.26 (t, J=6.8 Hz, 2H), 3.94 (d, J=5.7 Hz, 2H), 7.02 (t, J=7.5 Hz, 1H), 7.32-7.42 (m, 3H), 7.50-7.60 (m, 2H), 7.62 (d, J=7.7 Hz, 2H), 7.78 (d, J=7.3 Hz, 1H), 10.68 (s, 1H)

The following Reference Compound 8-(2) to (20) were obtained by a production method similar to that of Reference Compound 8-(1) using compounds selected from Reference Compounds 7-(2) to (22) (except for 7-(4) and 7-(16)) and commercially available compounds.

3-(2-(5-(4-Chlorophenylamino)-1,3,4-oxadiazol-2-yl)phenylthio)propanoic acid 2-ethylhexyl (Reference Compound 8-(2))

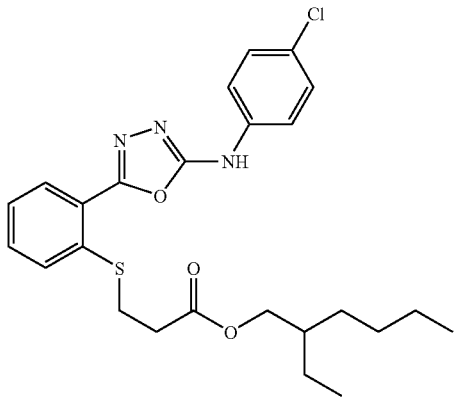

¹H-NMR (300 MHz, DMSO-d₆)

δ 0.75-0.83 (m, 6H), 1.15-1.30 (m, 8H), 1.50 (m, 1H), 2.68 (t, J=6.8 Hz, 2H), 3.26 (t, J=6.8 Hz, 2H), 3.93 (d, J=5.7 Hz, 2H), 7.38 (m, 1H), 7.43 (d, J=8.8 Hz, 2H), 7.54-7.60 (m, 2H), 7.64 (d, J=8.8 Hz, 2H), 7.78 (d, J=7.5 Hz, 1H), 10.87 (s, 1H)

54

3-(2-(5-(3-Trifluoromethylphenylamino)-1,3,4-oxadiazol-2-yl)phenylthio)propanoic acid 2-ethylhexyl (Reference Compound 8-(3))

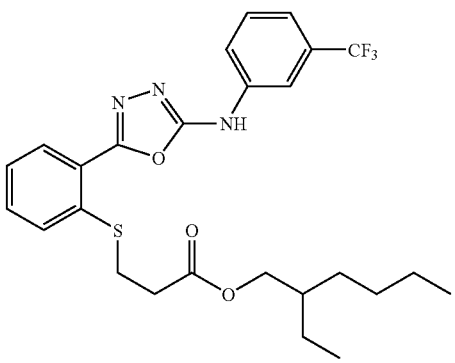

¹H-NMR (300 MHz, DMSO-d₆)

δ 0.75-0.83 (m, 6H), 1.17-1.30 (m, 8H), 1.47 (m, 1H), 2.68 (t, J=6.8 Hz, 2H), 3.26 (t, J=6.8 Hz, 2H), 3.93 (d, J=5.9 Hz, 2H), 7.35-7.42 (m, 2H), 7.52-7.65 (m, 3H), 7.77-7.84 (m, 2H), 8.11 (s, 1H), 11.11 (s, 1H)

3-(2-(5-Phenylamino-1,3,4-thiadiazol-2-yl)phenylthio)propanoic acid 2-ethylhexyl (Reference Compound 8-(4))

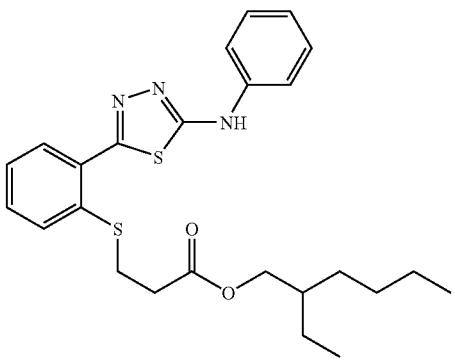

¹H-NMR (300 MHz, DMSO-d₆)

δ 0.75-0.85 (m, 6H), 1.15-1.25 (m, 8H), 1.43 (m, 1H), 2.60 (t, J=6.6 Hz, 2H), 3.17 (t, J=6.6 Hz, 2H), 3.90 (d, J=5.9 Hz, 2H), 7.03 (t, J=7.3 Hz, 1H), 7.30-7.45 (m, 3H), 7.49 (t, J=7.7 Hz, 1H), 7.62 (t, J=8.1 Hz, 1H), 7.66 (d, J=7.7 Hz, 1H), 7.93 (d, J=7.7 Hz, 1H), 10.51 (s, 1H)

3-(2-(5-(4-Chlorophenylamino)-1,3,4-thiadiazol-2-yl)phenylthio)propanoic acid 2-ethylhexyl (Reference Compound 8-(5))

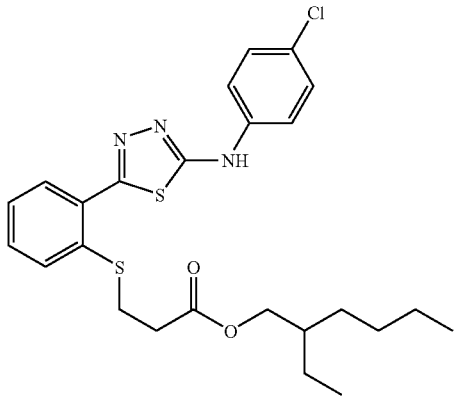

¹H-NMR (300 MHz, DMSO-d₆)

δ 0.70-0.90 (m, 6H), 1.10-1.15 (m, 8H), 1.23 (m, 1H), 2.60 (t, J=6.6 Hz, 2H), 3.17 (t, J=6.6 Hz, 2H), 3.90 (d, J=5.7 Hz, 2H), 7.38-7.46 (m, 3H), 7.50 (t, J=7.5 Hz, 1H), 7.63 (d, J=8.1 Hz, 1H), 7.71 (d, J=9.0 Hz, 2H), 7.94 (d, J=7.5 Hz, 1H), 10.64 (s, 1H)

3-(2-(5-(3-Chlorophenylamino)-1,3,4-thiadiazol-2-yl)phenylthio)propanoic acid 2-ethylhexyl (Reference Compound 8-(6))

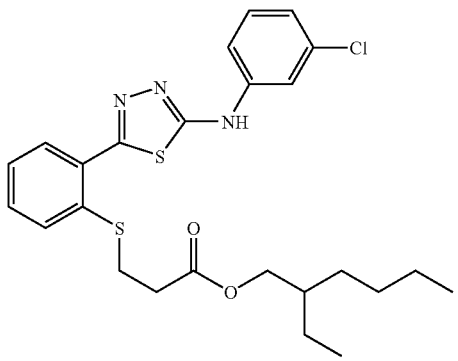

¹H-NMR (300 MHz, DMSO-d₆)

δ 0.75-0.83 (m, 6H), 1.16-1.25 (m, 8H), 1.45 (m, 1H), 2.60 (t, J=6.6 Hz, 2H), 3.17 (t, J=6.6 Hz, 2H), 3.90 (d, J=5.5 Hz, 2H), 7.07 (d, J=7.7 Hz, 1H), 7.34-7.55 (m, 4H), 7.64 (d, J=7.7 Hz, 1H), 7.93-8.00 (m, 2H), 10.73 (s, 1H)

3-(2-(5-(4-Trifluoromethylphenylamino)-1,3,4-thiadiazol-2-yl)phenylthio)propanoic acid 2-ethylhexyl (Reference Compound 8-(7))

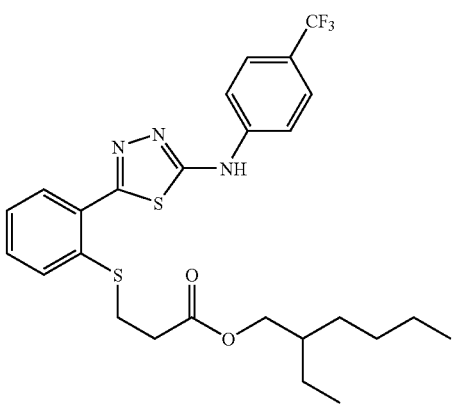

¹H-NMR (300 MHz, DMSO-d₆)

δ 0.74-0.80 (m, 6H), 1.15-1.25 (m, 8H), 1.46 (m, 1H), 2.60 (t, J=6.6 Hz, 2H), 3.18 (t, J=6.6 Hz, 2H), 3.90 (d, J=5.9 Hz, 2H), 7.43 (d, J=7.7 Hz, 1H), 7.51 (t, J=7.7 Hz, 1H), 7.65 (d, J=7.7 Hz, 1H), 7.73 (d, J=8.8 Hz, 2H), 7.89 (d, J=8.8 Hz, 2H), 7.97 (d, J=7.7 Hz, 1H), 10.94 (s, 1H)

3-(2-(5-(4-Trifluoromethoxyphenylamino)-1,3,4-oxadiazol-2-yl)phenylthio)propanoic acid 2-ethylhexyl (Reference Compound 8-(8))

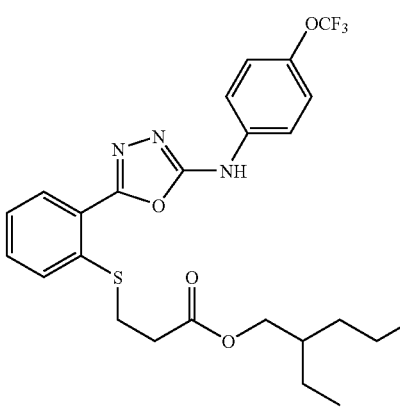

¹H-NMR (300 MHz, DMSO-d₆)

δ 0.87 (m, 6H), 1.20-1.40 (m, 9H), 2.72 (t, J=7.3 Hz, 2H), 3.28 (t, J=7.3 Hz, 2H), 3.98-4.10 (m, 2H), 7.24 (d, J=9.0 Hz, 2H), 7.34 (t, J=7.7 Hz, 1H), 7.46 (t, J=7.7 Hz, 1H), 7.53 (d, J=7.7 Hz, 1H), 7.62 (d, J=9.0 Hz, 2H), 7.85 (br s, 1H), 7.88 (d, J=7.7 Hz, 1H)

3-(2-(5-(3-Trifluoromethylphenylamino)-1,3,4-thiadiazol-2-yl)phenylthio)propanoic acid 2-ethylhexyl (Reference Compound 8-(9))

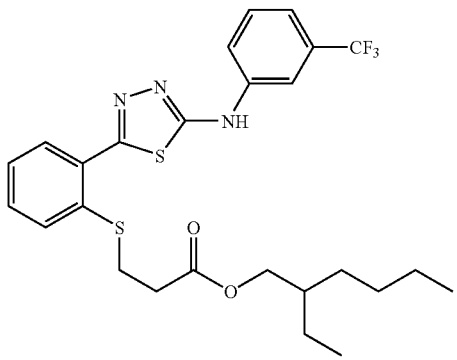

$^1$H-NMR (300 MHz, DMSO-$d_6$)

δ 0.74-0.82 (m, 6H), 1.10-1.30 (m, 8H), 1.43 (m, 1H), 2.60 (t, J=6.6 Hz, 2H), 3.18 (t, J=6.6 Hz, 2H), 3.90 (d, J=5.7 Hz, 2H), 7.36 (br d, J=8.1 Hz, 1H), 7.42 (t, J=5.5 Hz, 1H), 7.51 (t, J=7.5 Hz, 1H), 7.60 (t, J=8.1 Hz, 1H), 7.65 (d, J=7.5 Hz, 1H), 7.79 (d, J=8.1 Hz, 1H), 7.97 (br d, J=7.5 Hz, 1H), 8.28 (br s, 1H), 10.88 (s, 1H)

3-(2-(5-(4-Trifluoromethoxyphenylamino)-1,3,4-thiadiazol-2-yl)phenylthio)propanoic acid 2-ethylhexyl (Reference Compound 8-(10))

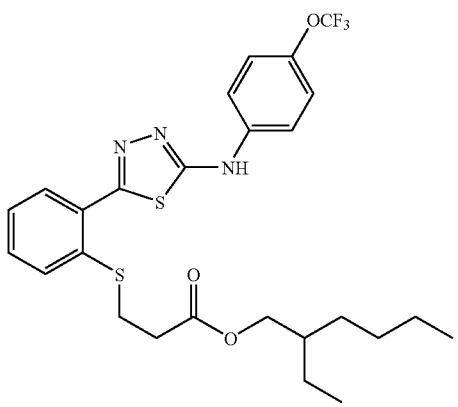

$^1$H-NMR (300 MHz, DMSO-$d_6$)

δ 0.70-0.82 (m, 6H), 1.16-1.25 (m, 8H), 1.43 (m, 1H), 2.60 (t, J=6.6 Hz, 2H), 3.17 (t, J=6.6 Hz, 2H), 3.90 (t, J=5.7 Hz, 2H), 7.35-7.46 (m, 3H), 7.50 (t, J=7.9 Hz, 1H), 7.63 (d, J=7.7 Hz, 1H), 7.79 (d, J=9.0 Hz, 2H), 7.95 (d, J=7.9 Hz, 1H), 10.70 (s, 1H)

3-(2-(5-Phenylamino-1,3,4-oxadiazol-2-yl)thiophen-3-ylthio)propanoic acid 2-ethylhexyl (Reference Compound 8-(11))

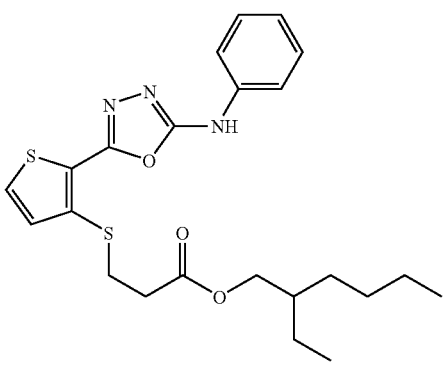

$^1$H-NMR (300 MHz, DMSO-$d_6$)

δ 10.68 (1H, s), 7.92 (1H, d, J=5.4 Hz), 7.60 (2H, d, J=7.8 Hz), 7.38-7.31 (3H, m), 7.01 (1H, t, J=7.2 Hz), 3.93 (2H, d, J=5.7 Hz), 3.41-3.33 (2H, m), 2.69 (2H, t, J=6.6 Hz), 1.48 (1H, m), 1.30-1.19 (8H, m), 0.82-0.77 (6H, m)

3-(2-(5-(4-Chlorophenylamino)-1,3,4-oxadiazol-2-yl)thiophen-3-ylthio)propanoic acid 2-ethylhexyl (Reference Compound 8-(12))

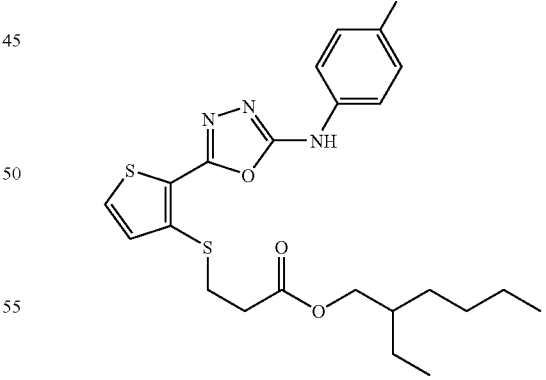

$^1$H-NMR (300 MHz, DMSO-$d_6$)

δ 10.87 (1H, s), 7.91 (1H, d, J=5.3 Hz), 7.62 (2H, d, J=8.6 Hz), 7.42 (2H, d, J=8.6 Hz), 7.32 (1H, d, J=5.3 Hz), 3.93 (2H, d, J=5.5 Hz), 3.33-3.29 (2H, m), 2.67 (2H, t, J=6.8 Hz), 1.448 (1H, m), 1.29-1.19 (8H, m), 0.79 (6H, m)

3-(2-(5-(4-Trifluoromethoxyphenylamino)-1,3,4-oxadiazol-2-yl)thiophen-3-ylthio)propanoic acid 2-ethylhexyl (Reference Compound 8-(13))

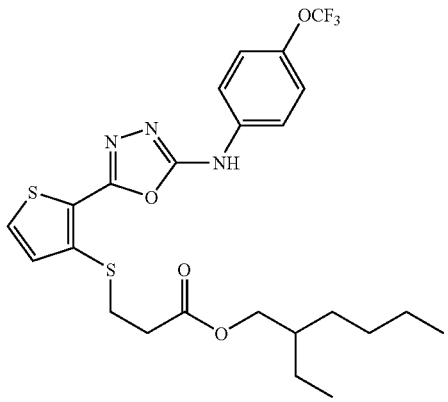

¹H-NMR (300 MHz, DMSO-d₆)

δ 10.94 (1H, s), 7.91 (1H, d, J=5.3 Hz), 7.70 (2H, d, J=8.8 Hz), 7.38 (2H, d, J=8.8 Hz), 7.32 (1H, d, J=5.3 Hz), 3.93 (2H, d, J=5.3 Hz), 3.32-3.28 (2H, m), 2.69 (2H, t, J=6.7 Hz), 1.48 (1H, m), 1.30-1.19 (8H, m), 0.81-0.78 (6H, m)

3-(2-(5-(4-Trifluoromethoxyphenylamino)-1,3,4-oxadiazol-2-yl)thiophen-3-ylthio)propanoic acid 2-ethylhexyl (Reference Compound 8-(14))

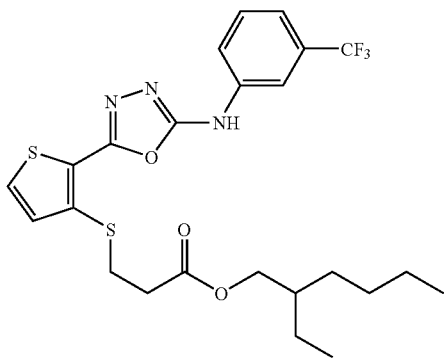

¹H-NMR (300 MHz, DMSO-d₆)

δ 11.13 (1H, s), 8.07 (1H, s), 7.92 (1H, d, J=5.1 Hz), 7.78 (1H, d, J=8.1 Hz), 7.59 (1H, t, J=8.1 Hz), 7.35-7.33 (2H, m), 3.92 (2H, d, J=5.7 Hz), 3.32-3.29 (2H, m), 2.67 (2H, t, J=6.7 Hz), 1.48 (1H, m), 1.29-1.18 (8H, m), 0.81-0.78 (6H, m)

3-(2-(5-Phenylamino-1,3,4-thiadiazol-2-yl)thiophen-3-ylthio)propanoic acid 2-ethylhexyl (Reference Compound 8-(15))

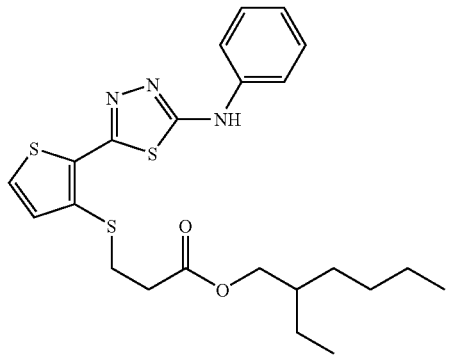

¹H-NMR (300 MHz, DMSO-d₆)

δ 10.51 (1H, s), 7.78 (1H, d, J=5.1 Hz), 7.63 (2H, d, J=7.8 Hz), 7.39-7.30 (3H, m), 7.02 (1H, t, J=7.2 Hz), 3.88 (2H, d, J=5.7 Hz), 3.19 (2H, t, J=6.6 Hz), 2.56 (2H, t, J=6.6 Hz), 1.42 (1H, m), 1.25-1.15 (8H, m), 0.78-0.73 (6H, m)

3-(2-(5-(4-Chlorophenylamino)-1,3,4-thiadiazol-2-yl)thiophen-3-ylthio)propanoic acid 2-ethylhexyl (Reference Compound 8-(16))

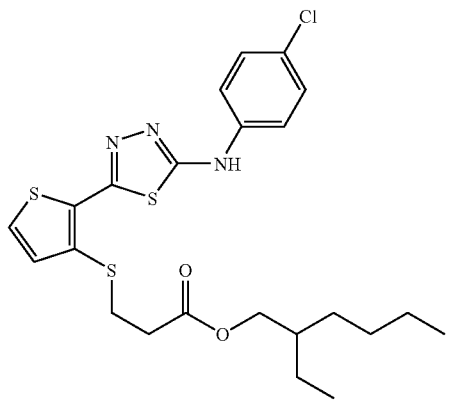

¹H-NMR (300 MHz, DMSO-d₆)

δ 10.64 (1H, s), 7.79 (1H, d, J=5.1 Hz), 7.68 (2H, d, J=9.0 Hz), 7.41 (2H, d, J=9.0 Hz), 7.31 (1H, d, J=5.1 Hz), 3.88 (2H, d, J=5.9 Hz), 3.19 (2H, t, J=6.6 Hz), 2.56 (2H, t, J=6.6 Hz), 1.41 (1H, m), 1.25-1.14 (8H, m), 0.79-0.74 (6H, m)

3-(2-(5-(4-Trifluoromethoxyphenylamino)-1,3,4-thiadiazol-2-yl)thiophen-3-ylthio)propanoic acid 2-ethylhexyl (Reference Compound 8-(17))

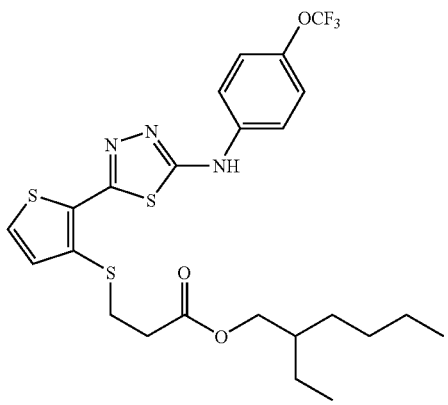

¹H-NMR (300 MHz, DMSO-d₆)

δ 10.70 (1H, s), 7.78-7.76 (3H, m), 7.37 (2H, d, J=9.0 Hz), 7.31 (1H, d, J=5.3 Hz), 3.87 (2H, d, J=5.7 Hz), 3.19 (2H, t, J=6.5 Hz), 2.56 (2H, t, J=6.5 Hz), 1.42 (1H, m), 1.27-1.18 (8H, m), 0.84-0.75 (6H, m)

3-(2-(5-(3-Trifluoromethylphenylamino)-1,3,4-thiadiazol-2-yl)thiophen-3-ylthio)propanoic acid 2-ethylhexyl (Reference Compound 8-(18))

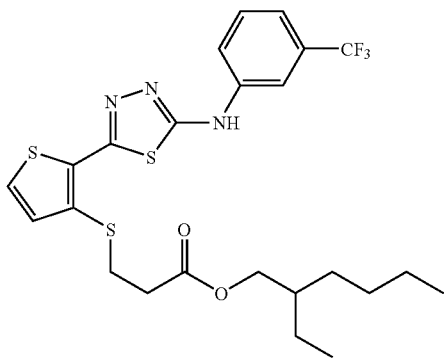

¹H-NMR (300 MHz, DMSO-d₆)

δ 10.88 (1H, s), 8.25 (1H, s), 7.81 (1H, d, J=5.2 Hz), 7.75 (1H, d, J=8.6 Hz), 7.59 (1H, m), 7.36-7.33 (2H, m), 3.87 (2H, d, J=5.8 Hz), 3.20 (2H, t, J=6.4 Hz), 2.57 (2H, t, J=6.4 Hz), 1.40 (1H, m), 1.24-1.12 (8H, m), 0.75-0.73 (6H, m)

3-(3-(5-(4-Chlorophenylamino)-1,3,4-oxadiazol-2-yl)thiophen-2-ylthio)propanoic acid 2-ethylhexyl (Reference Compound 8-(19))

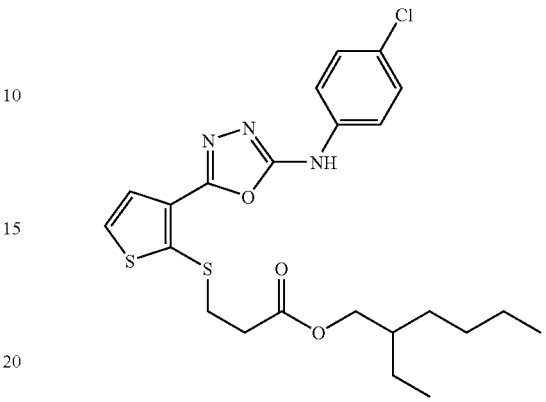

¹H-NMR (300 MHz, DMSO-d₆)

δ 10.84 (1H, s), 7.76 (1H, d, J=4.7 Hz), 7.64 (2H, d, J=8.8 Hz), 7.46-7.42 (3H, m), 3.92 (2H, d, J=5.7 Hz), 3.28-3.26 (2H, m), 2.70 (2H, t, J=6.6 Hz), 1.48 (1H, m), 1.28-1.20 (9H, m), 0.82-0.79 (6H, m)

3-(3-(5-(3-Trifluoromethylphenylamino)-1,3,4-thiadiazol-2-yl)thiophen-2-ylthio)propanoic acid 2-ethylhexyl (Reference Compound 8-(20))

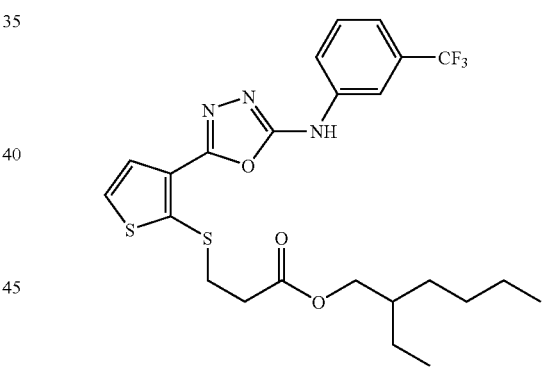

¹H-NMR (300 MHz, DMSO-d₆)

δ 8.10 (1H, s), 7.80-7.77 (2H, m), 7.60 (1H, t, J=7.6 Hz), 7.46 (1H, d, J=5.7 Hz), 7.35 (1H, d, J=7.6 Hz), 3.92 (2H, d, J=5.7 Hz), 3.29-3.24 (2H, m), 2.70 (2H, t, J=6.7 Hz), 1.49 (1H, m), 1.25-1.22 (8H, m), 0.81-0.79 (6H, m)

Reference Example 10

2-(5-(3-Trifluoromethylphenylamino)-1,3,4-oxadiazol-2-yl)phenol (Reference Compound 9-(1))

To a solution of 1-(2-bromobenzoyl)-4-phenylsemicarbazide (CAS#904425-30-5) (2.9 g, 8.5 mmol), triphenylphosphine (3.3 g, 1.5 mmol) and triethylamine (1.3 g, 13 mmol) in methylene chloride (60 mL) was added carbon tetrachloride (5.2 g, 34 mmol) under ice-cooling, and then the mixture was refluxed overnight. The reaction solution was cooled to room temperature and ethyl acetate (20 mL) was added thereto. The ethyl acetate solution was washed with a saturated brine solution (10 mL) twice, dried over anhydrous sodium sulfate, and concentrated under a reduced pressure to dryness. The residue was purified with a silica gel column chromatography (hexane/ethyl acetate) to give 1.5 g (53%) of the titled compound as a colorless solid.

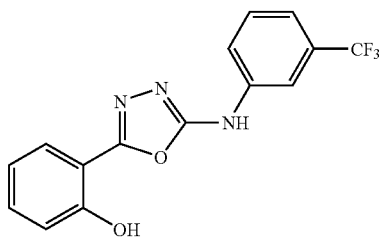

$^1$H-NMR (300 MHz, DMSO-d$_6$)
δ 7.01 (dd, J=7.5, 7.5 Hz, 1H), 7.08 (d, J=8.3 Hz, 1H), 7.38 (d, J=7.5, 1H), 7.44 (m, 1H), 7.63 (dd, J=7.9, 7.9 Hz, 1H), 7.69 (m, 1H), 7.82 (m, 1H), 8.10 (m, 1H), 10.23 (m, 1H), 11.18 (m, 1H)

Example 1

N-Phenyl-5-(2-(pyridin-4-yl)methoxyphenyl)-1,3,4-oxadiazol-2-amine (Compound 1-(1))

To a solution of 4-phenyl-1-(2-(pyridin-4-yl) methoxybenzoyl) semicarbazide (110 mg, 0.47 mmol; Reference Compound 6-(1) and triphenylphosphine (190 mg, 0.71 mmol) in a mixed solvent of methylene chloride (3.0 mL) and tetrahydrofuran (3.0 mL) were added carbon tetrachloride (290 mg, 1.9 mmol) and triethylamine (70 mg, 0.71 mmol), and then the mixture was refluxed overnight. The reaction solution was cooled to room temperature and ethyl acetate was added thereto. The ethyl acetate solution was washed with a saturated brine solution. To the solution was added a 1M hydrochloric acid and then the aqueous layer was taken out. To the aqueous layer was added a 1 M aqueous sodium hydroxide solution. The solid which precipitated at pH 8 was filtered off and dried under a reduced pressure to give 65 mg (40%) of the titled compound as a colorless solid.

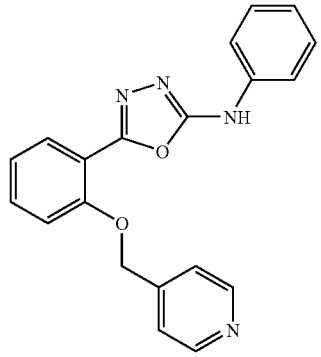

$^1$H-NMR (300 MHz, DMSO-d$_6$)
δ 5.38 (s, 2H), 7.02 (dd, J=7.3, 7.3 Hz, 1H), 7.16 (dd, J=7.5, 7.5 Hz, 1H), 7.33 (m, 3H), 7.58 (m, 5H), 7.80 (dd, J=7.7, 1.7 Hz, 1H), 8.57 (dd, J=4.1, 1.5 Hz, 2H), 10.61 (s, 1H)

The following Compounds 1-(2) to (31) were obtained by a production method similar to that of Compound 1-(1) using compound selected from Reference Compounds 6-(2) to (31), known compounds and commercially available compounds.

N-(4-Chlorophenyl)-5-(2-(pyridin-4-yl)methoxyphenyl)-1,3,4-oxadiazol-2-amino (Compound 1-(2))

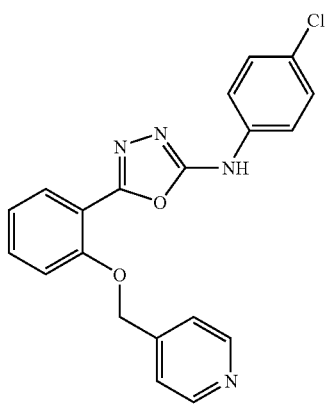

$^1$H-NMR (300 MHz, DMSO-d$_6$)
δ 5.38 (s, 2H), 7.17 (m, 1H), 7.29 (d, J=8.4 Hz, 1H), 7.42 (d, J=8.8 Hz, 2H), 7.53-7.58 (m, 3H), 7.65 (d, J=8.8 Hz, 2H), 7.80 (dd, J=7.7, 1.7 Hz, 1H), 8.58 (d, J=5.9 Hz, 2H), 10.80 (s, 1H)

5-(2-(Pyridin-4-yl)methoxyphenyl)-N-(3-trifluoromethylphenyl)-1,3,4-oxadiazol-2-amine (Compound 1-(3))

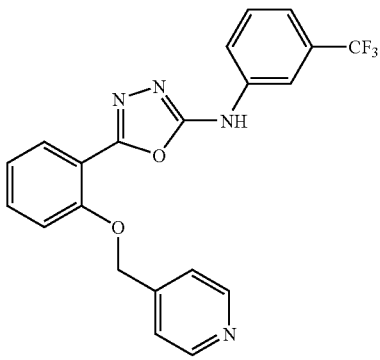

$^1$H-NMR (300 MHz, DMSO-d$_6$)
δ 5.39 (s, 2H), 7.17 (dd, J=7.3, 7.3 Hz, 1H), 7.30 (d, J=7.9 Hz, 1H), 7.37 (d, J=7.3 Hz, 1H), 7.55-7.63 (m, 4H), 7.81 (dd, J=7.9, 1.7 Hz, 1H), 7.87 (m, 1H), 8.08 (s, 1H), 8.58 (dd, J=4.4, 1.7 Hz, 2H), 11.05 (s, 1H)

N-Phenyl-5-(2-(quinolin-4-yl)methoxyphenyl)-1,3,4-oxadiazol-2-amine (Compound 1-(4))

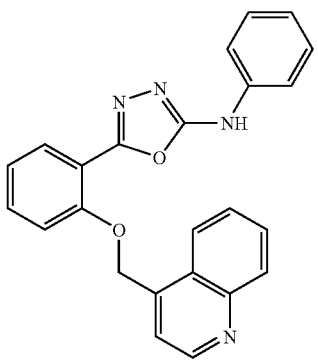

¹H-NMR (300 MHz, DMSO-d₆)

δ 5.88 (s, 2H), 7.01 (m, 1H), 7.19 (m, 1H), 7.36 (dd, J=8.4, 7.3 Hz, 2H), 7.58-7.68 (m, 5H), 7.77-7.84 (m, 2H), 8.00 (d, J=4.8 Hz, 1H), 8.07 (d, J=7.7 Hz, 1H), 8.24 (d, J=9.0 Hz, 1H), 8.91 (d, J=4.4 Hz, 1H), 10.62 (s, 1H)

5-(2-(2-Acetamidopyridin-4-yl)methoxyphenyl)-N-phenyl-1,3,4-oxadiazol-2-amine (Compound 1-(6))

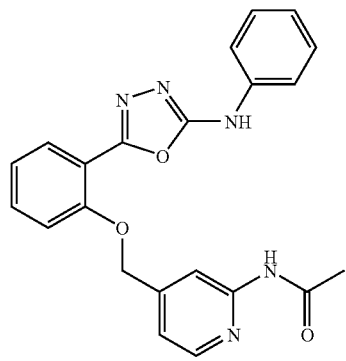

¹H-NMR (300 MHz, DMSO-d₆)

δ 2.37 (s, 3H), 5.37 (s, 2H), 7.01 (dd, J=7.3, 7.3 Hz, 1H), 7.16 (m, 1H), 7.28-7.38 (m, 4H), 7.52-7.64 (m, 3H), 7.82 (dd, J=7.9, 1.7 Hz, 1H), 8.21 (s, 1H), 8.29 (d, J=5.1 Hz, 1H), 10.50 (s, 1H), 10.55 (s, 1H)

N-Phenyl-5-(3-(pyridin-4-yl)methoxythiophen-2-yl)-1,3,4-oxadiazol-2-amine (Compound 1-(5))

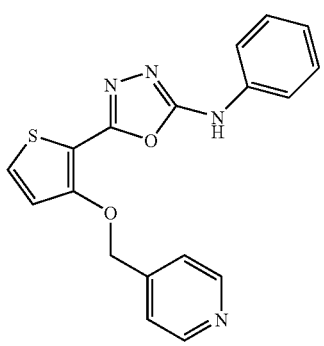

¹H-NMR (300 MHz, DMSO-d₆)

δ 5.42 (s, 2H), 7.00 (dd, J=7.5, 7.5 Hz, 1H), 7.21 (d, J=5.7 Hz, 1H), 7.32 (dd, J=8.3, 7.5 Hz, 2H), 7.50 (d, J=5.5 Hz, 2H), 7.59 (d, J=7.9 Hz, 2H), 7.76 (d, J=5.5 Hz, 2H), 8.58 (d, J=5.9 Hz, 2H), 10.60 (s, 1H)

5-(2-(2-t-Butoxycarbonylaminopyridin-4-yl)methylthiopyridin-3-yl)-N-phenyl-1,3,4-oxadiazol-2-amine (Compound 1-(7))

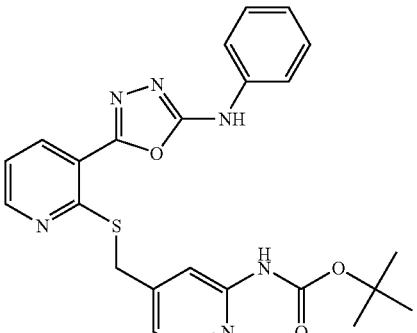

¹H-NMR (300 MHz, DMSO-d₆)

δ 1.45 (s, 9H), 4.48 (s, 2H), 7.03 (t, J=7.3 Hz, 1H), 7.08 (d, J=5.0 Hz, 1H), 7.33-7.42 (m, 3H), 7.62 (d, J=7.7 Hz, 2H), 7.91 (s, 1H), 8.08-8.16 (m, 2H), 8.63 (m, 1H), 9.71 (s, 1H), 10.78 (s, 1H)

67

5-(2-(2-t-Butoxycarbonylaminopyridin-4-yl)methylthiopyridin-3-yl)-N-(4-chlorophenyl)-1,3,4-oxadiazol-2-amine (Compound 1-(8))

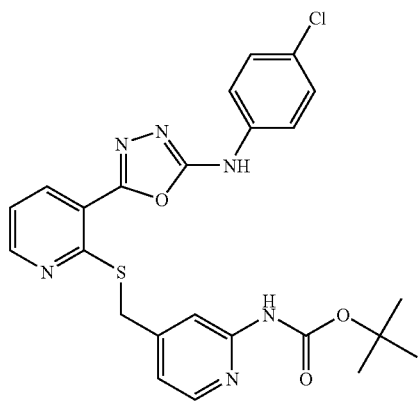

¹H-NMR (300 MHz, DMSO-d₆)

δ 1.45 (s, 9H), 4.48 (s, 2H), 7.08 (m, 1H), 7.38 (dd, J=7.7, 4.8 Hz, 1H), 7.43 (d, J=8.8 Hz, 2H), 7.64 (d, J=8.8 Hz, 2H), 7.91 (s, 1H), 8.09-8.14 (m, 2H), 8.63 (dd, J=4.6, 1.7 Hz, 1H), 9.72 (s, 1H), 10.96 (s, 1H)

5-(2-(2-t-Butoxycarbonylaminopyridin-4-yl)methylthiopyridin-3-yl)-N-(3-trifluoromethylphenyl)-1,3,4-oxadiazol-2-amine (Compound 1-(9))

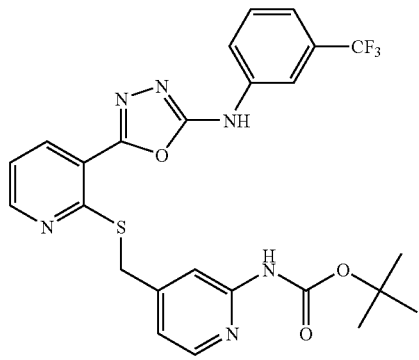

¹H-NMR (300 MHz, DMSO-d₆)

δ 1.45 (s, 9H), 4.48 (s, 2H), 7.08 (m, 1H), 7.36-7.42 (m, 2H), 7.62 (t, J=7.9 Hz, 1H), 7.82 (m, 1H), 7.91 (s, 1H), 8.08-8.16 (m, 3H), 8.64 (dd, J=4.6, 1.5 Hz, 1H), 9.72 (s, 1H), 11.21 (s, 1H)

68

N-Phenyl-5-(2-(pyridin-4-yl)methylthiopyridin-3-yl)-1,3,4-oxadiazol-2-amine (Compound 1-(10))

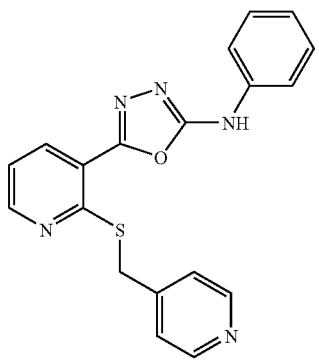

¹H-NMR (300 MHz, DMSO-d₆)

δ 4.51 (s, 2H), 7.03 (t, J=7.3 Hz, 1H), 7.34-7.40 (m, 3H), 7.45 (d, J=5.9 Hz, 2H), 7.62 (d, J=7.3 Hz, 2H), 8.11 (dd, J=7.7, 1.7 Hz, 1H), 8.48 (d, J=5.9 Hz, 2H), 8.63 (dd, J=4.8, 1.7 Hz, 1H), 10.76 (s, 1H)

N-(4-Chlorophenyl)-5-(2-(pyridin-4-yl)methylthiopyridin-3-yl)-1,3,4-oxadiazol-2-amine (Compound 1-(11))

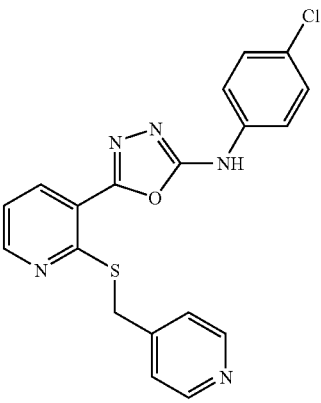

¹H-NMR (300 MHz, DMSO-d₆)

δ 4.51 (s, 2H), 7.38 (dd, J=7.9, 4.8 Hz, 1H), 7.41-7.46 (m, 4H), 7.64 (d, J=9.0 Hz, 2H), 8.11 (dd, J=7.9, 1.8 Hz, 1H), 8.47 (d, J=5.9 Hz, 2H), 8.63 (dd, J=4.8, 1.8 Hz, 1H), 10.95 (s, 1H)

5-(2-(Pyridin-4-yl)methylthiopyridin-3-yl)-N-(3-trifluoromethylphenyl)-1,3,4-oxadiazol-2-amine (Compound 1-(12))

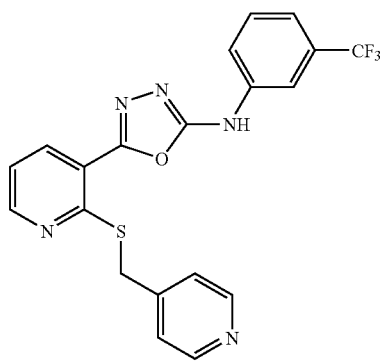

¹H-NMR (300 MHz, DMSO-d₆)

δ 4.51 (s, 2H), 7.36-7.42 (m, 2H), 7.45 (d, J=6.0 Hz, 2H), 7.61 (t, J=8.2 Hz, 1H), 7.82 (br d, J=8.2 Hz, 1H), 8.09 (br s, 1H), 8.12 (dd, J=7.9, 1.8 Hz, 1H), 8.48 (d, J=6.0 Hz, 2H), 8.64 (dd, J=4.8, 1.8 Hz, 1H), 11.20 (s, 1H)

N-Phenyl-5-(2-(quinolin-4-yl)methylthiopyridin-3-yl)-1,3,4-oxadiazol-2-amine (Compound 1-(13))

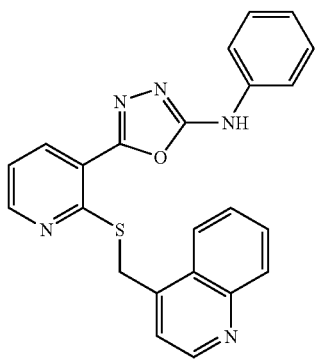

¹H-NMR (300 MHz, DMSO-d₆)

δ 5.03 (s, 2H), 7.01 (t, J=7.3 Hz, 1H), 7.35 (t, J=7.3 Hz, 2H), 7.40 (dd, J=7.9, 5.0 Hz, 1H), 7.59 (d, J=7.3 Hz, 2H), 7.64-7.72 (m, 2H), 7.79 (m, 1H), 8.05 (d, J=8.3 Hz, 1H), 8.13 (d, J=7.7 Hz, 1H), 8.29 (d, J=8.3 Hz, 1H), 8.69 (d, J=5.0 Hz, 1H), 8.81 (d, J=4.6 Hz, 1H), 10.74 (s, 1H)

N-(4-Chlorophenyl)-5-(2-(quinolin-4-yl)methylthiopyridin-3-yl)-1,3,4-oxadiazol-2-amine (Compound 1-(14))

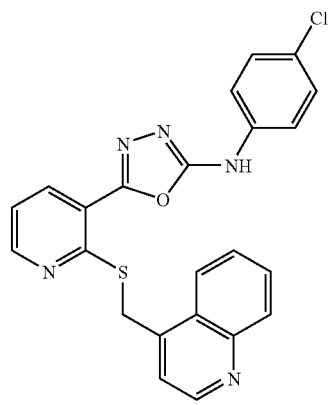

¹H-NMR (300 MHz, DMSO-d₆)

δ 5.03 (s, 2H), 7.38-7.44 (m, 3H), 7.58-7.70 (m, 5H), 7.79 (m, 1H), 8.05 (br d, J=7.5 Hz, 1H), 8.13 (dd, J=7.7, 1.7 Hz, 1H), 8.29 (br d, J=8.3 Hz, 1H), 8.69 (dd, J=4.8, 1.8 Hz, 1H), 8.82 (d, J=4.4 Hz, 1H), 10.93 (s, 1H)

5-(2-(Quinolin-4-yl)methylthiopyridin-3-yl)-N-(3-trifluoromethylphenyl)-1,3,4-oxadiazol-2-amine (Compound 1-(15))

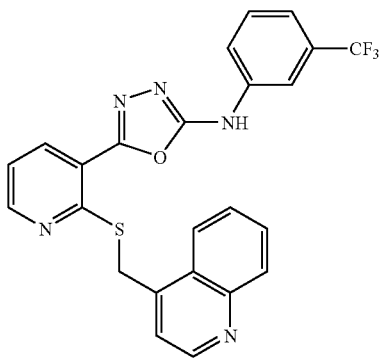

¹H-NMR (300 MHz, DMSO-d₆)

δ 5.03 (s, 2H), 7.36 (m, 1H), 7.42 (dd, J=7.7, 4.8 Hz, 1H), 7.59 (m, 1H), 7.64-7.70 (m, 2H), 7.75-7.82 (m, 2H), 8.02-8.10 (m, 2H), 8.14 (dd, J=7.9, 1.7 Hz, 1H), 8.29 (m, 1H), 8.70 (dd, J=4.8, 1.7 Hz, 1H), 8.81 (d, J=4.4 Hz, 1H), 11.18 (s, 1H)

71

5-(2-(2-Acetamidopyridin-4-yl)methylthiopyridin-3-yl)-N-phenyl-1,3,4-oxadiazol-2-amine (Compound 1-(16))

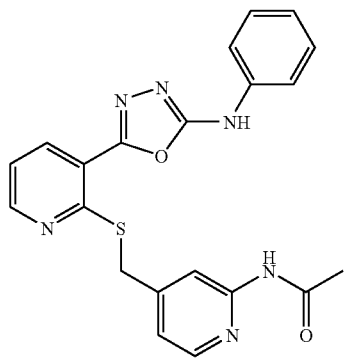

¹H-NMR (300 MHz, DMSO-d₆)

δ 2.06 (s, 3H), 4.49 (s, 2H), 7.03 (t, J=7.3 Hz, 1H), 7.14 (d, J=5.1 Hz, 1H), 7.34-7.42 (m, 3H), 7.62 (d, J=7.3 Hz, 2H), 8.12 (d, J=7.9 Hz, 1H), 8.18-8.22 (m, 2H), 8.62 (d, J=4.6 Hz, 1H), 10.43 (s, 1H), 10.77 (s, 1H)

5-(2-(2-Acetamidopyridin-4-yl)methylthiopyridin-3-yl)-N-(4-chlorophenyl)-1,3,4-oxadiazol-2-amine (Compound 1-(17))

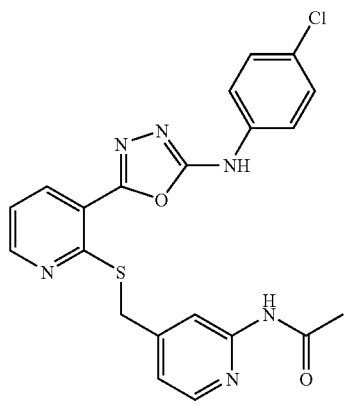

¹H-NMR (300 MHz, DMSO-d₆)

δ 2.06 (s, 3H), 4.49 (s, 2H), 7.14 (br d, J=6.6 Hz, 1H), 7.38 (dd, J=7.7, 4.8 Hz, 1H), 7.43 (d, J=8.9 Hz, 2H), 7.64 (d, J=8.9 Hz, 2H), 8.11 (dd, J=7.9, 1.7 Hz, 1H), 8.17-8.22 (m, 2H), 8.62 (dd, J=4.8, 1.7 Hz, 1H), 10.42 (s, 1H), 10.94 (s, 1H)

72

5-(2-(2-Acetamidopyridin-4-yl)methylthiopyridin-3-yl)-N-(3-trifluoromethylphenyl)-1,3,4-oxadiazol-2-amine (Compound 1-(18))

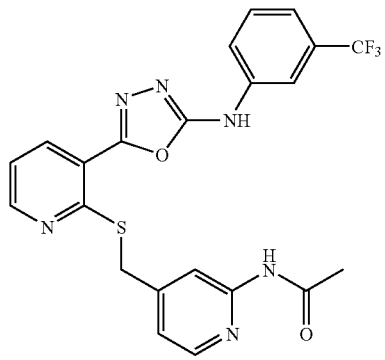

¹H-NMR (300 MHz, DMSO-d₆)

δ 2.06 (s, 3H), 4.49 (s, 2H), 7.14 (m, 1H), 7.36-7.42 (m, 2H), 7.62 (d, J=8.1 Hz, 1H), 7.82 (m, 1H), 8.08-8.14 (m, 2H), 8.18-8.22 (m, 2H), 8.64 (dd, J=4.6, 1.7 Hz, 1H), 10.44 (s, 1H), 11.22 (s, 1H)

5-(2-(2-Methylaminocarbonylpyridin-4-yl)methylthiopyridin-3-yl)-N-phenyl-1,3,4-oxadiazol-2-amine (Compound 1-(19))

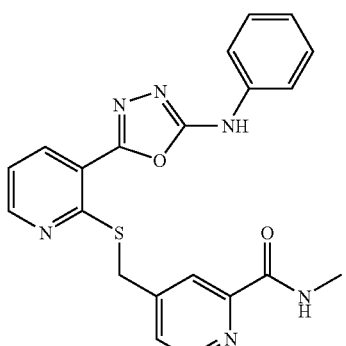

¹H-NMR (300 MHz, DMSO-d₆)

δ 2.80 (d, J=4.8 Hz, 3H), 4.60 (s, 2H), 7.03 (t, J=7.5 Hz, 1H), 7.34-7.42 (m, 3H), 7.60-7.80 (m, 3H), 8.10-8.12 (m, 2H), 8.53 (d, J=5.0 Hz, 1H), 8.61 (m, 1H), 8.74 (q, J=4.8 Hz, 1H), 10.79 (s, 1H)

73

N-(4-Chlorophenyl)-5-(2-(2-methylaminocarbonylpyridin-4-yl) methylthiopyridin-3-yl)-1,3,4-oxadiazol-2-amine (Compound 1-(20))

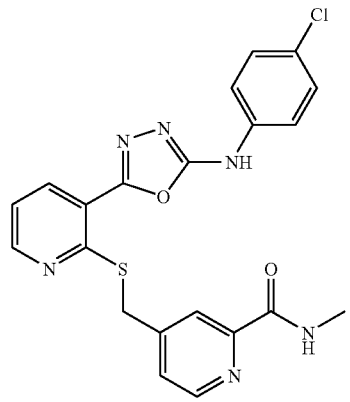

¹H-NMR (300 MHz, DMSO-d₆)

δ 2.80 (d, J=5.0 Hz, 3H), 4.60 (s, 2H), 7.38 (dd, J=7.9, 4.8 Hz, 1H), 7.44 (d, J=8.8 Hz, 2H), 7.60-7.68 (m, 3H), 8.08-8.14 (m, 2H), 8.53 (d, J=5.0 Hz, 1H), 8.61 (dd, J=4.8, 1.7 Hz, 1H), 8.74 (q, J=5.0 Hz, 1H), 10.97 (s, 1H)

5-(2-(2-Methylaminocarbonylpyridin-4-yl)methylthiopyridin-3-yl)-N-(3-trifluoromethylphenyl)-1,3,4-oxadiazol-2-amine (Compound 1-(21))

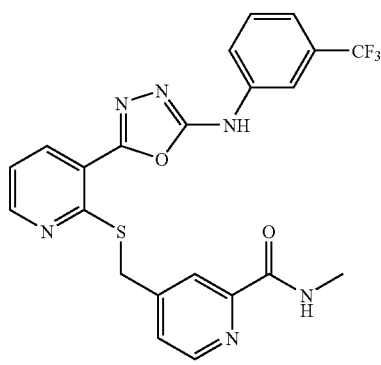

¹H-NMR (300 MHz, DMSO-d₆)

δ 2.80 (d, J=4.8 Hz, 3H), 4.61 (s, 2H), 7.36-7.42 (m, 2H), 7.58-7.66 (m, 2H), 7.82 (m, 1H), 8.08-8.15 (m, 3H), 8.53 (d, J=5.0 Hz, 1H), 8.62 (dd, J=4.8, 1.7 Hz, 1H), 8.75 (q, J=4.8 Hz, 1H), 11.23 (s, 1H)

74

N-(2-Chloro-5-trifluoromethylphenyl)-5-(2-(pyridin-4-yl) methoxyphenyl)-1,3,4-oxadiazol-2-amine (Compound 1-(22))

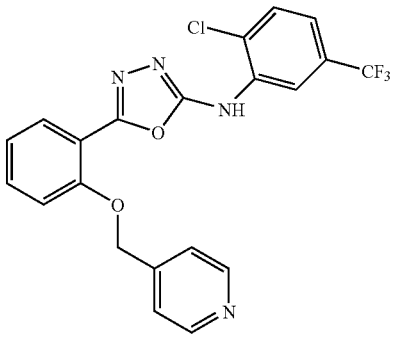

¹H-NMR (300 MHz, DMSO-d₆)

δ 5.37 (s, 2H), 7.18 (dd, J=7.7, 7.7 Hz, 1H), 7.30 (d, J=8.4 Hz, 1H), 7.47-7.55 (m, 2H), 7.56 (d, J=5.5 Hz, 2H), 7.80 (dd, J=8.6, 8.6 Hz, 2H), 8.56 (m, 3H), 10.41 (s, 1H)

N-(4-t-Butylphenyl)-5-(2-(pyridin-4-yl)methoxyphenyl)-1,3,4-oxadiazol-2-amine (Compound 1-(23))

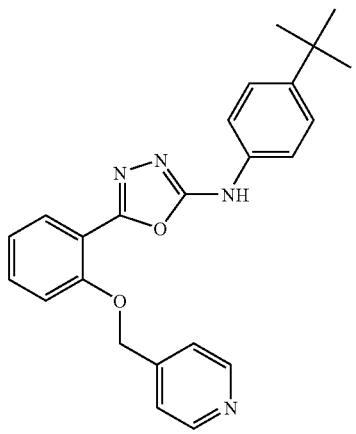

¹H-NMR (300 MHz, DMSO-d₆)

δ 1.27 (s, 9H), 5.38 (s, 2H), 7.15 (dd, J=7.5, 7.5 Hz, 1H), 7.29 (d, J=8.1 Hz, 1H), 7.35 (d, J=8.8 Hz, 2H), 7.50-7.57 (m, 5H), 7.79 (dd, J=7.7, 1.7 Hz, 1H), 8.55 (dd, J=5.9, 1.5 Hz, 2H), 10.49 (s, 1H)

5-(3-(Pyridin-4-yl)methoxythiophen-2-yl)-N-(3-trifluoromethylphenyl)-1,3,4-oxadiazol-2-amine (Compound 1-(24))

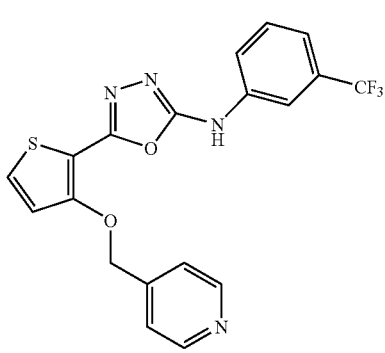

¹H-NMR (300 MHz, DMSO-d₆)

δ 5.43 (s, 2H), 7.21 (d, J=6.5 Hz, 1H), 7.36 (d, J=7.9 Hz, 1H), 7.49 (d, J=6.1 Hz, 2H), 7.59 (dd, J=7.9, 7.9 Hz, 1H), 7.77-7.83 (m, 2H), 8.07 (s, 1H), 8.59 (dd, J=4.6, 1.7 Hz, 2H), 10.49 (s, 1H)

5-(5-Bromo-2-(pyridin-4-yl)methoxyphenyl)-N-phenyl-1,3,4-oxadiazol-2-amine (Compound 1-(25))

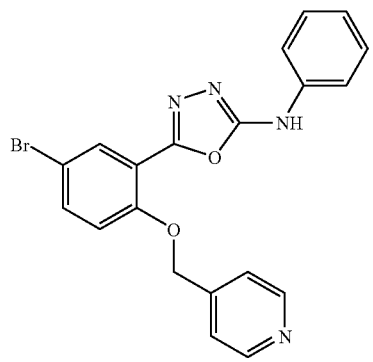

¹H-NMR (300 MHz, DMSO-d₆)

δ 5.39 (s, 2H), 7.02 (t, J=7.5 Hz, 1H), 7.28 (d, J=9.0 Hz, 1H), 7.36 (t, J=7.5 Hz, 2H), 7.56 (d, J=6.1 Hz, 2H), 7.62 (d, J=4.7 Hz, 2H), 7.74 (dd, J=9.0, 2.6 Hz, 1H), 7.91 (d, J=2.6 Hz, 1H), 8.58 (d, J=6.1 Hz, 2H), 10.67 (s, 1H)

5-(5-Methoxy-2-(pyridin-4-yl)methoxyphenyl)-N-phenyl-1,3,4-oxadiazol-2-amine (Compound 1-(26))

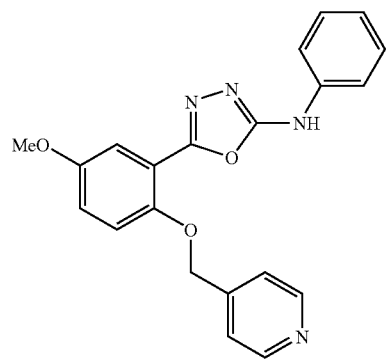

¹H-NMR (300 MHz, DMSO-d₆)

δ 3.78 (s, 3H), 5.30 (s, 2H), 7.00 (t, J=7.3 Hz, 1H), 7.12 (dd, J=9.0, 3.1 Hz, 1H), 7.23 (d, J=9.0 Hz, 1H), 7.31 (d, J=3.1 Hz, 1H), 7.34 (t, J=7.3 Hz, 2H), 7.55 (d, J=5.3 Hz, 2H), 7.62 (d, J=7.3 Hz, 2H), 8.56 (d, J=5.3 Hz, 2H), 10.04 (s, 1H)

N-phenyl-5-(3-(Pyridin-4-yl)methoxypyridin-2-yl)-1,3,4-oxadiazol-2-amine (Compound 1-(27))

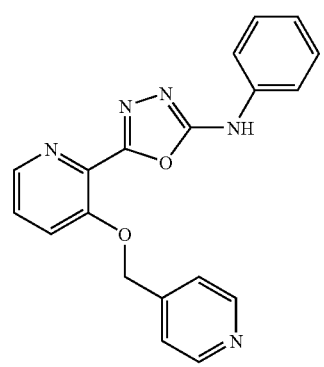

¹H-NMR (300 MHz, DMSO-d₆)

δ 5.45 (s, 2H), 7.03 (t, J=7.3 Hz, 1H), 7.38 (t, J=7.8 Hz, 2H), 7.54-7.66 (m, 5H), 7.80 (d, J=8.4 Hz, 1H), 8.35 (d, J=4.2 Hz, 1H), 8.62 (d, J=5.9 Hz, 2H), 10.82 (s, 1H)

5-(3-(Pyridin-4-yl)methoxypyridin-2-yl)-N-(3-trifluoromethylphenyl)-1,3,4-oxadiazol-2-amine (Compound 1-(28))

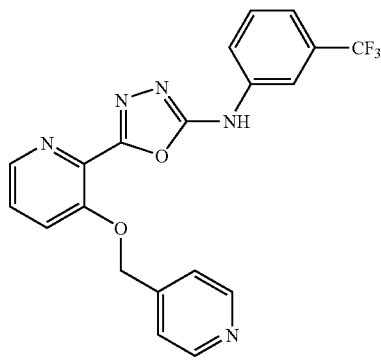

¹H-NMR (300 MHz, DMSO-d₆)

δ 5.46 (s, 2H), 7.39 (br d, J=8.1 Hz, 1H), 7.58-7.68 (m, 4H), 7.81 (d, J=8.6 Hz, 1H), 7.87 (d, J=9.0 Hz, 1H), 8.07 (s, 1H), 8.36 (d, J=4.6 Hz, 1H), 8.62 (d, J=5.1 Hz, 2H), 11.26 (s, 1H)

5-(2-(2-Acetamidopyridin-4-yl)methylthiopyridin-3-yl)-N-(4-trifluoromethoxyphenyl)-1,3,4-oxadiazol-2-amine (Compound 1-(29))

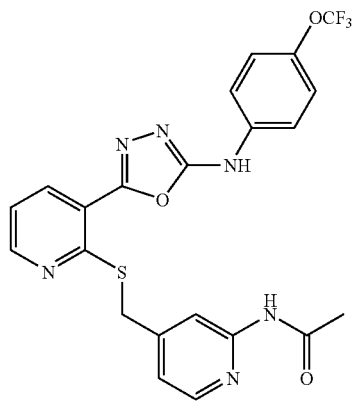

¹H-NMR (300 MHz, DMSO-d₆)

δ 2.06 (s, 3H), 4.49 (s, 2H), 7.14 (d, J=5.3 Hz, 1H), 7.35-7.43 (m, 3H), 7.71 (d, J=9.0 Hz, 2H), 8.12 (d, J=7.9 Hz, 1H), 8.18-8.22 (m, 2H), 8.63 (d, J=5.3 Hz, 1H), 10.43 (s, 1H), 11.02 (s, 1H)

N-(4-(2-(5-Phenylamino-1,3,4-oxadiazol-2-yl)thiophen-3-yloxy)methylpyridin-2-yl)acetamide (Compound 1-(30))

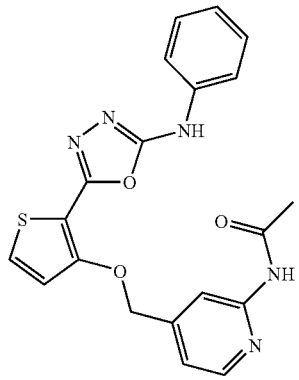

¹H-NMR (300 MHz, DMSO-d₆)

δ 2.13 (s, 3H), 5.40 (s, 2H), 7.00 (t, J=7.2 Hz, 1H), 7.17-7.24 (m, 2H), 7.34 (t, J=8.1 Hz, 2H), 7.62 (d, J=8.1 Hz, 2H), 7.76 (d, J=5.5 Hz, 1H), 8.28-8.30 (m, 2H), 10.50 (s, 1H), 10.63 (s, 1H)

N-(4-(2-(5-(3-Trifluoromethylphenyl)amino-1,3,4-oxadiazol-2-yl)thiophen-3-yl)oxymethylpyridin-2-yl)acetamide (Compound 1-(31))

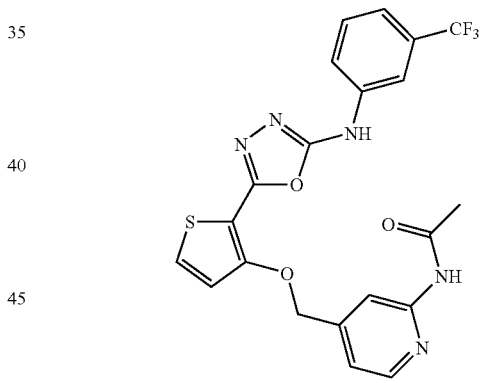

¹H-NMR (300 MHz, DMSO-d₆)

δ 2.12 (s, 3H), 5.41 (s, 2H), 7.18 (m, 1H), 7.22 (d, J=5.5 Hz, 1H), 7.36 (d, J=8.0 Hz, 1H), 7.60 (t, J=8.0 Hz, 1H), 7.78 (d, J=5.5 Hz, 1H), 7.86 (d, J=8.0 Hz, 1H), 8.07 (s, 1H), 8.28 (s, 1H), 8.31 (d, J=5.3 Hz, 1H), 10.63 (s, 1H), 10.92 (s, 1H)

Example 2

N-Phenyl-5-(2-(pyridin-4-yl)methylthiophenyl)-1,3,4-oxadiazol-2-amine (Compound 1-(32))

A vessel containing 5-(2-bromophenyl)-N-phenyl-1,3,4-oxadiazol-2-amine (220 mg, 0.70 mmol; Reference Compound 7-(1)), tris(dibenzylideneacetone)dipalladium (33 mg, 0.035 mmol) and Xantphos (81 mg, 0.14 mmol) was replaced with nitrogen gas. To the vessel were added dioxane (5.0 mL), diisopropylethylamine (0.43 mL, 2.5 mmol) and 4-pyridinemethanethiol hydrochloride (210 mg, 1.3 mmol) suc- N-(4-t-Butylphenyl)-5-(2-(pyridin-4-yl)methylthiophenyl)-1,3,4-oxadiazol-2-amine (Compound 1-(34))

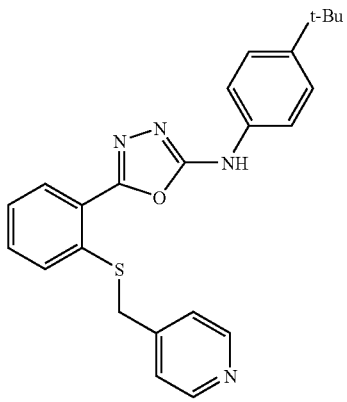

¹H-NMR (300 MHz, DMSO-d₆)

δ 1.28 (s, 9H), 4.37 (s, 2H), 7.32-7.57 (m, 9H), 7.77 (d, J=7.6 Hz, 1H), 8.49 (d, J=5.9 Hz, 2H), 10.58 (s, 1H)

N-Phenyl-5-(2-(pyridin-4-yl)methylthiophenyl)-1,3,4-thiadiazol-2-amine (Compound 1-(35))

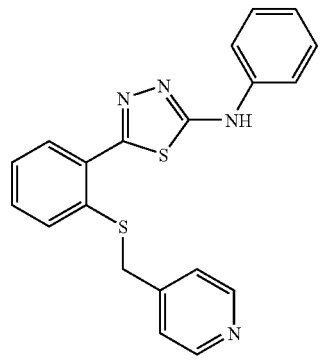

¹H-NMR (300 MHz, DMSO-d₆)

δ 4.27 (s, 2H), 7.02 (t, J=7.3 Hz, 1H), 7.31 (d, J=5.9 Hz, 2H), 7.34-7.46 (m, 4H), 7.56 (d, J=7.2 Hz, 1H), 7.66 (d, J=7.7 Hz, 2H), 7.86 (d, J=7.7 Hz, 1H), 8.46 (d, J=5.9 Hz, 2H), 10.51 (s, 1H)

cessively at room temperature, and then the mixture was refluxed overnight. The reaction solution was cooled to room temperature and diluted with ethyl acetate (15 mL). The ethyl acetate solution was washed with a saturated brine solution (20 mL), dried over anhydrous sodium sulfate and concentrated under a reduced pressure. To the residue was added ethanol and a precipitated solid was filtered off and dried to give 180 mg (70%) of the titled compound as a pale brown solid.

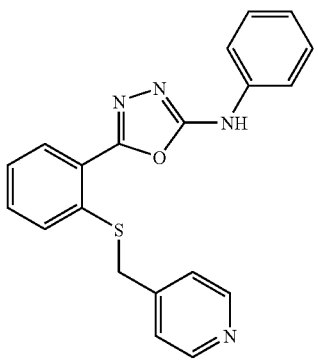

¹H-NMR (300 MHz, DMSO-d₆)

δ 4.37 (s, 2H), 7.02 (t, J=7.3 Hz, 1H), 7.34-7.40 (m, 3H), 7.43 (d, J=5.9 Hz, 2H), 7.44-7.57 (m, 2H), 7.61 (d, J=8.4 Hz, 2H), 7.78 (d, J=6.8 Hz, 1H), 8.50 (d, J=5.9 Hz, 2H), 10.70 (s, 1H)

The following Compounds 1-(33) to (39) were obtained by a production method similar to that of Compound 1-(32) using compounds selected from Reference Compounds 7-(3), 7-(4), 7-(12) to (16) and commercially available compounds.

5-(2-(Pyridin-4-yl)methylthiophenyl)-N-(3-trifluoromethylphenyl)-1,3,4-oxadiazol-2-amine (Compound 1-(33))

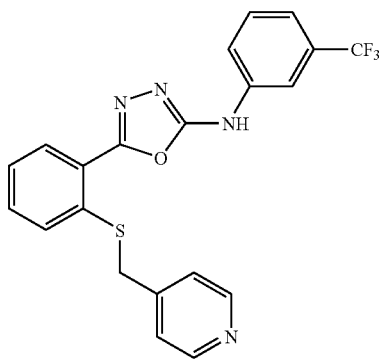

¹H-NMR (300 MHz, DMSO-d₆)

δ 4.61 (s, 2H), 7.36-7.44 (m, 2H), 7.51 (t, J=7.7 Hz, 1H), 7.56-7.66 (m, 2H), 7.77-7.86 (m, 2H), 7.88-7.95 (m, 2H), 8.12 (s, 1H), 8.75 (d, J=5.7 Hz, 2H), 10.20 (s, 1H)

N-(4-Chlorophenyl)-5-(2-(pyridin-4-yl)methylthiophenyl)-1,3,4-thiadiazol-2-amine (Compound 1-(36))

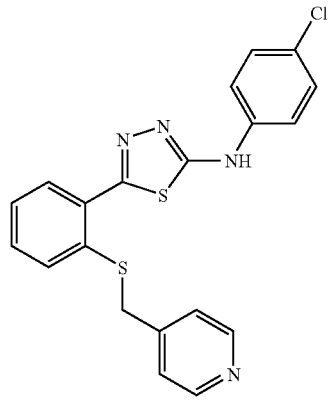

¹H-NMR (300 MHz, DMSO-d$_6$)

δ 4.26 (s, 2H), 7.29 (d, J=5.9 Hz, 2H), 7.35-7.46 (m, 4H), 7.57 (d, J=7.9 Hz, 1H), 7.71 (d, J=9.0 Hz, 2H), 7.87 (d, J=7.7 Hz, 1H), 8.46 (d, J=5.9 Hz, 2H), 10.65 (s, 1H)

N-(3-Chlorophenyl)-5-(2-(pyridin-4-yl)methylthiophenyl)-1,3,4-thiadiazol-2-amine (Compound 1-(37))

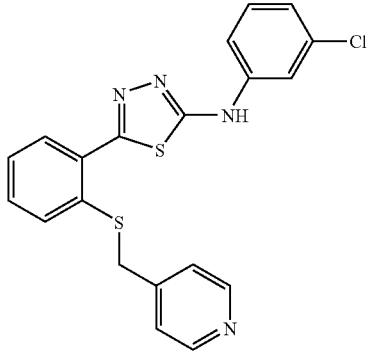

¹H-NMR (300 MHz, DMSO-d$_6$)

δ 4.26 (s, 2H), 7.07 (d, J=8.8 Hz, 1H), 7.29 (d, J=6.1 Hz, 2H), 7.34-7.52 (m, 4H), 7.58 (d, J=7.7 Hz, 1H), 7.88 (dd, J=7.7, 1.7 Hz, 1H), 7.96 (t, J=2.0 Hz, 1H), 8.45 (d, J=6.1 Hz, 2H), 10.73 (s, 1H)

5-(2-(Pyridin-4-yl)methylthiophenyl)-N-(4-trifluoromethylphenyl)-1,3,4-thiadiazole-2-amine (Compound 1-(38))

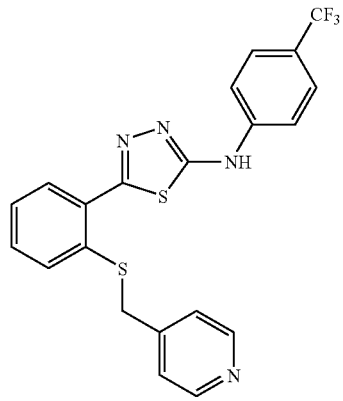

¹H-NMR (300 MHz, DMSO-d$_6$)

δ 4.27 (s, 2H), 7.29 (d, J=5.9 Hz, 2H), 7.39 (t, J=7.3 Hz, 1H), 7.46 (t, J=7.3 Hz, 1H), 7.58 (d, J=7.3 Hz, 1H), 7.73 (d, J=8.8 Hz, 2H), 7.84-7.93 (m, 3H), 8.46 (d, J=5.9 Hz, 2H), 10.93 (s, 1H)

N-(4-t-Butylphenyl)-5-(2-(pyridin-4-yl)methylthiophenyl)-1,3,4-thiadiazol-2-amine (Compound 1-(39))

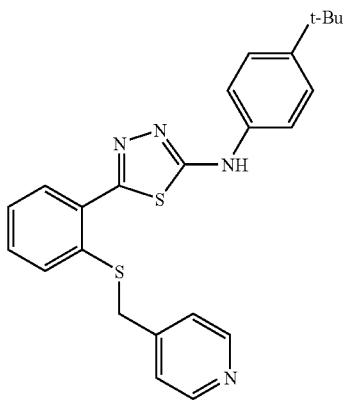

¹H-NMR (300 MHz, DMSO-d$_6$)

δ 1.28 (s, 9H), 4.26 (s, 2H), 7.30 (d, J=6.1 Hz, 2H), 7.35-7.43 (m, 4H), 7.52-7.60 (m, 3H), 7.86 (d, J=7.5 Hz, 1H), 8.45 (d, J=6.1 Hz, 2H), 10.43 (s, 1H)

Example 3

N-Phenyl-5-(2-(quinolin-4-yl)methylthiophenyl)-1,3,4-oxadiazol-2-amine (Compound 1-(40))

To a solution of 3-(2-(5-phenylamino-1,3,4-oxadiazol-2-yl) phenylthio)propanoic acid 2-ethylhexyl (110 mg, 0.22 mmol; Reference Compound 8-(1)) in tetrahydrofuran (1.0 mL) was added sodium t-butoxide (32 mg, 0.33 mmol) under ice-cooling and then the mixture was stirred for 50 minutes at room temperature. The reaction solution was placed under ice-cooling again and 4-chloromethylquinoline (48 mg, 0.27 mmol) was added thereto, followed by stirring the mixture for 2 hours at room temperature. To the reaction solution was added a saturated aqueous solution of ammonium chloride (5.0 mL) and water (5.0 mL) under ice-cooling. The mixture was extracted with ethyl acetate (15 mL). The ethyl acetate layer was washed with a saturated brine solution, dried over anhydrous sodium sulfate and then concentrated under a reduced pressure. The residue was filtered off with chloroform and dried to give 35 mg (38%) of the titled compound as a pale brown solid.

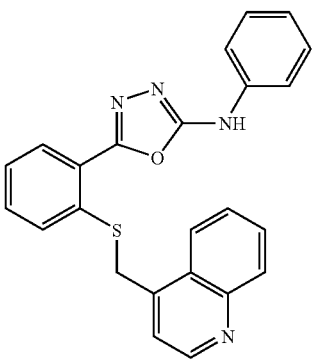

$^1$H-NMR (300 MHz, DMSO-$d_6$)

δ 4.86 (s, 2H), 7.00 (t, J=7.5 Hz, 1H), 7.30-7.42 (m, 3H), 7.49-7.60 (m, 4H), 7.62-7.69 (m, 2H), 7.76-7.82 (m, 2H), 8.05 (d, J=8.8 Hz, 1H), 8.31 (d, J=7.3 Hz, 1H), 8.81 (d, J=4.4 Hz, 1H), 10.65 (s, 1H)

The following Compounds 1-(41) to (86) were obtained by a production method similar to that of Compound 1-(40) using compounds selected from Reference Compounds 8-(1) to 8-(20), 4-chloromethylquinoline (CAS#5632-17-7; WO2006/093253), 2-acetamido-4-methanesulfonyloxymethylpyridine (CAS#864461-12-1; WO2005/085201), 2-amino-4-methanesulfonyloxymethylpyrimidine (CAS#912470-43-0; WO2006/106914), 4-chloromethyl-2-fuluoropyridine (CAS#864461-12-1; WO2005/085201) and commercially available compounds.

N-(4-Chlorophenyl)-5-(2-(pyridin-4-yl)methylthiophenyl)-1,3,4-oxadiazol-2-amine (Compound 1-(41))

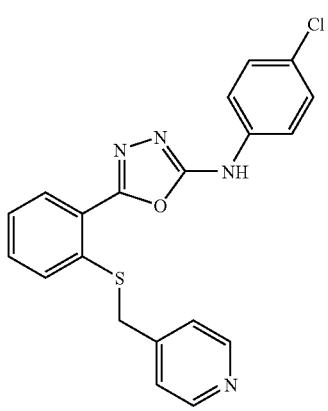

$^1$H-NMR (300 MHz, DMSO-$d_6$)

δ 4.37 (s, 2H), 7.32-7.60 (m, 7H), 7.64 (d, J=8.8 Hz, 2H), 7.77 (d, J=7.5 Hz, 1H), 8.49 (d, J=5.7 Hz, 2H), 10.88 (s, 1H)

N-(4-Chlorophenyl)-5-(2-(quinolin-4-yl)methylthiophenyl)-1,3,4-oxadiazol-2-amine (Compound 1-(42))

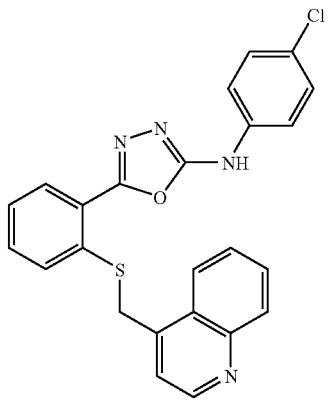

δ 4.85 (s, 2H), 7.35-7.43 (m, 3H), 7.50-7.70 (m, 6H), 7.74-7.82 (m, 2H), 8.05 (d, J=7.7 Hz, 1H), 8.30 (d, J=7.7 Hz, 1H), 8.81 (d, J=4.4 Hz, 1H), 10.84 (s, 1H)

5-(2-(Quinolin-4-yl)methylthiophenyl)-N-(3-trifluoromethylphenyl)-1,3,4-oxadiazol-2-amine (Compound 1-(43))

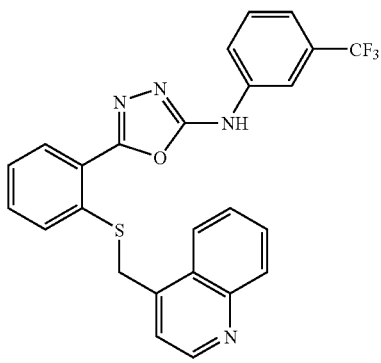

δ 4.85 (s, 2H), 7.33-7.44 (m, 2H), 7.50-7.70 (m, 5H), 7.73-7.83 (m, 3H), 8.02-8.10 (m, 2H), 8.30 (d, J=8.5 Hz, 1H), 8.80 (d, J=4.4 Hz, 1H), 9.10 (s, 1H)

5-(2-(2-Acetamidopyridin-4-yl)methylthiophenyl)-N-phenyl-1,3,4-oxadiazol-2-amine (Compound 1-(44))

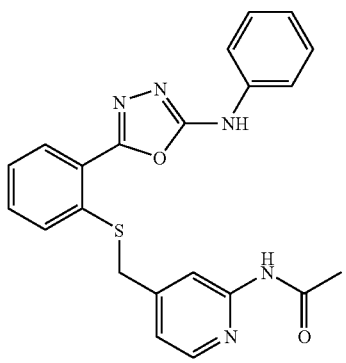

$^1$H-NMR (300 MHz, DMSO-$d_6$)

δ 2.07 (s, 3H), 4.36 (s, 2H), 7.02 (t, J=7.3 Hz, 1H), 7.13 (d, J=5.1 Hz, 1H), 7.16-7.42 (m, 3H), 7.46-7.58 (m, 2H), 7.63 (d, J=8.8 Hz, 2H), 7.78 (d, J=7.7 Hz, 1H), 8.17 (s, 1H), 8.22 (d, J=5.1 Hz, 1H), 10.48 (s, 1H), 10.72 (s, 1H)

5-(2-(2-Acetamidopyridin-4-yl)methylthiophenyl)-N-(4-chlorophenyl-1,3,4-oxadiazol-2-amine (Compound 1-(45))

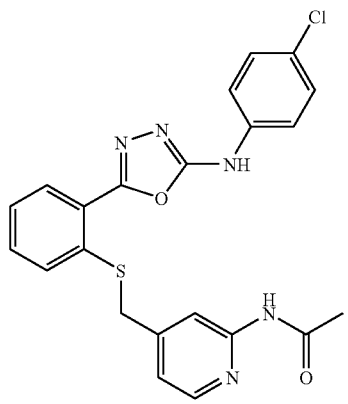

$^1$H-NMR (300 MHz, DMSO-d$_6$)
δ 2.06 (s, 3H), 4.36 (s, 2H), 7.13 (d, J=5.1 Hz, 1H), 7.35 (t, J=7.7 Hz, 1H), 7.43 (d, J=8.8 Hz, 2H), 7.46-7.58 (m, 2H), 7.64 (d, J=8.8 Hz, 2H), 7.78 (d, J=7.7 Hz, 1H), 8.17 (s, 1H), 8.21 (d, J=5.1 Hz, 1H), 10.49 (s, 1H), 10.88 (s, 1H)

5-(2-(2-Acetamidopyridin-4-yl)methylthiophenyl)-N-(3-trifluoromethylphenyl)-1,3,4-oxadiazol-2-amine (Compound 1-(46))

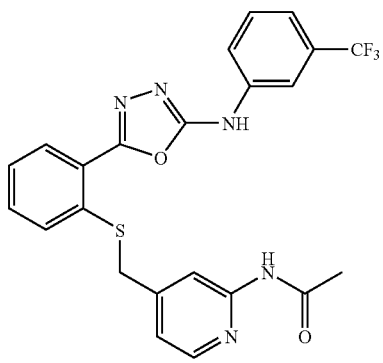

$^1$H-NMR (300 MHz, DMSO-d$_6$)
δ 2.06 (s, 3H), 4.36 (s, 2H), 7.12 (d, J=5.0 Hz, 1H), 7.32-7.40 (m, 2H), 7.46-7.65 (m, 3H), 7.76-7.84 (m, 2H), 8.10 (br s, 1H), 8.17 (s, 1H), 8.21 (d, J=5.0 Hz, 1H), 10.47 (s, 1H), 11.11 (s, 1H)

5-(2-(2-Aminopyrimidin-4-yl)methylthiophenyl)-N-phenyl-1,3,4-oxadiazol-2-amine (Compound 1-(47))

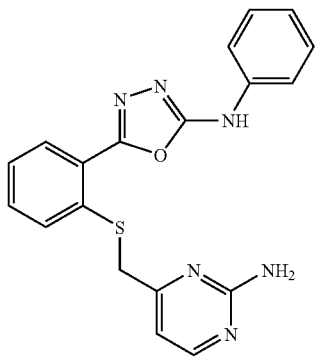

$^1$H-NMR (300 MHz, DMSO-d$_6$)
δ 4.17 (s, 2H), 6.64-6.70 (m, 3H), 7.02 (t, J=7.5 Hz, 1H), 7.31-7.42 (m, 3H), 7.50 (d, J=7.5 Hz, 1H), 7.56-7.66 (m, 3H), 7.78 (d, J=7.5 Hz, 1H), 8.16 (d, J=5.0 Hz, 1H), 10.69 (s, 1H)

5-(2-(2-Fluoropyridin-4-yl)methylthiophenyl)-N-phenyl-1,3,4-oxadiazol-2-amine (Compound 1-(48))

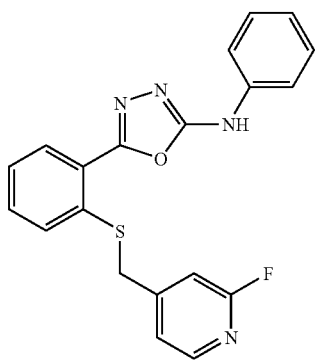

$^1$H-NMR (300 MHz, DMSO-d$_6$)
δ 4.43 (s, 2H), 7.02 (t, J=7.3 Hz, 1H), 7.21 (s, 1H), 7.33-7.44 (m, 4H), 7.46-7.68 (m, 4H), 7.80 (d, J=7.5 Hz, 1H), 8.17 (d, J=5.1 Hz, 1H), 10.70 (s, 1H)

N-Phenyl-5-(2-(quinolin-4-yl)methylthiophenyl)-1,3,4-thiadiazol-2-amine (Compound 1-(49))

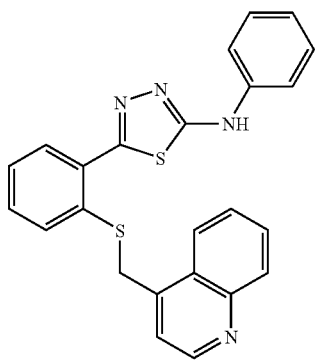

$^1$H-NMR (300 MHz, DMSO-d$_6$)
δ 4.73 (s, 2H), 7.01 (t, J=7.3 Hz, 1H), 7.30-7.46 (m, 5H), 7.56-7.66 (m, 4H), 7.75 (t, J=7.7 Hz, 1H), 7.88 (d, J=7.3, 1.8 Hz, 1H), 8.02 (d, J=8.6 Hz, 1H), 8.26 (d, J=8.6 Hz, 1H), 8.74 (d, J=4.6 Hz, 1H), 10.48 (s, 1H)

N-(4-Chlorophenyl)-5-(2-(quinolin-4-yl)methylthiophenyl)-1,3,4-thiadiazol-2-amine (Compound 1-(50))

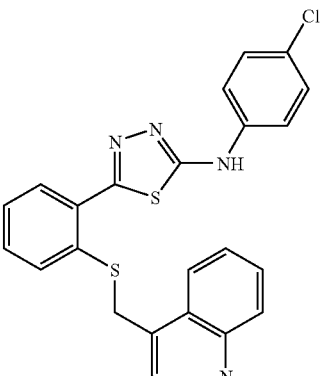

¹H-NMR (300 MHz, DMSO-d₆)
δ 4.75 (s, 2H), 7.35 (d, J=4.6 Hz, 1H), 7.38-7.46 (m, 4H), 7.57-7.82 (m, 5H), 7.87 (m, 1H), 8.03 (d, J=8.5 Hz, 1H), 8.29 (d, J=5.4 Hz, 1H), 8.79 (d, J=4.6 Hz, 1H), 10.59 (s, 1H)

N-(3-Chlorophenyl)-5-(2-(quinolin-4-yl)methylthiophenyl)-1,3,4-thiadiazol-2-amine (Compound 1-(51))

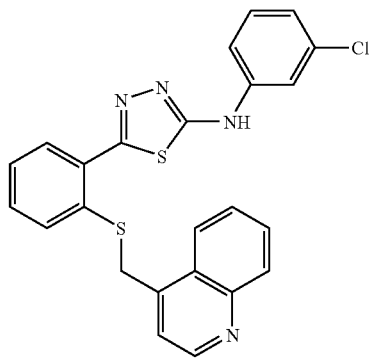

¹H-NMR (300 MHz, DMSO-d₆)
δ 4.73 (s, 2H), 7.06 (d, J=8.6 Hz, 1H), 7.30-7.50 (m, 5H), 7.56-7.66 (m, 2H), 7.74 (m, 1H), 7.88-7.94 (m, 2H), 8.00 (d, J=8.1 Hz, 1H), 8.25 (d, J=8.1 Hz, 1H), 8.73 (d, J=4.4 Hz, 1H), 10.66 (s, 1H)

5-(2-(Quinolin-4-yl)methylthiophenyl)-N-(4-trifluoromethylphenyl)-1,3,4-thiadiazol-2-amine (Compound 1-(52))

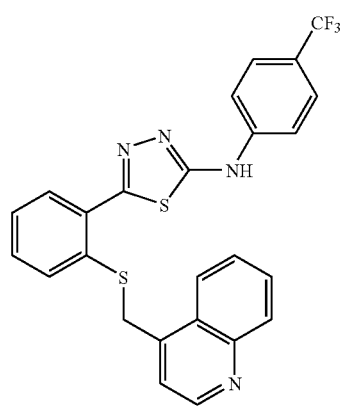

¹H-NMR (300 MHz, DMSO-d₆)
δ 4.73 (s, 2H), 7.31 (d, J=4.4 Hz, 1H), 7.40-7.50 (m, 2H), 7.58-7.66 (m, 2H), 7.68-7.76 (m, 3H), 7.80-7.96 (m, 3H), 8.00 (d, J=8.3 Hz, 1H), 8.25 (d, J=8.3 Hz, 1H), 8.73 (d, J=4.6 Hz, 1H), 10.87 (s, 1H)

5-(2-(2-Acetamidopyridin-4-yl)methylthiophenyl)-N-phenyl-1,3,4-thiadiazol-2-amine (Compound 1-(53))

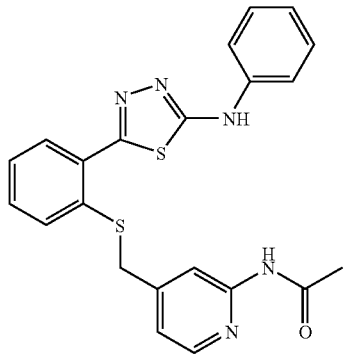

¹H-NMR (300 MHz, DMSO-d₆)
δ 2.05 (s, 3H), 4.25 (s, 2H), 6.96-7.06 (m, 2H), 7.32-7.46 (m, 4H), 7.57 (d, J=8.1 Hz, 1H), 7.65 (d, J=8.8 Hz, 2H), 7.86 (d, J=7.9 Hz, 1H), 8.08 (s, 1H), 8.17 (d, J=5.3 Hz, 1H), 10.43 (s, 1H), 10.50 (s, 1H)

5-(2-(2-Fluoropyridin-4-yl)methylthiophenyl)-N-phenyl-1,3,4-thiadiazol-2-amine (Compound 1-(54))

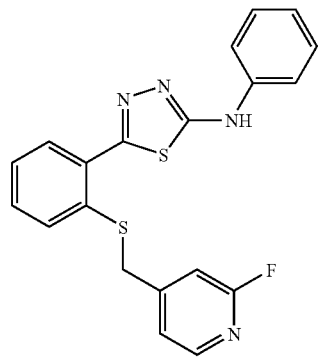

¹H-NMR (300 MHz, DMSO-d₆)
δ 4.31 (s, 2H), 7.03 (t, J=7.3 Hz, 1H), 7.05 (s, 1H), 7.25 (m, 1H), 7.32-7.48 (m, 4H), 7.57 (m, 1H), 7.66 (d, J=7.7 Hz, 2H), 7.86 (dd, J=7.5, 1.7 Hz, 1H), 8.13 (d, J=5.0 Hz, 1H), 10.52 (s, 1H)

5-(2-(2-Acetamidopyridin-4-yl)methylthiophenyl)-N-(4-trifluoromethylphenyl)-1,3,4-thiadiazol-2-amine (Compound 1-(55))

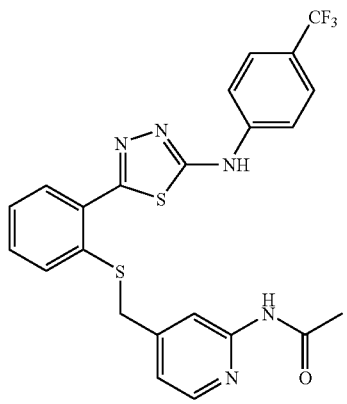

¹H-NMR (300 MHz, DMSO-d₆)

δ 2.04 (s, 3H), 4.26 (s, 2H), 6.97 (d, J=5.1 Hz, 1H), 7.38 (t, J=7.7 Hz, 1H), 7.45 (t, J=7.7 Hz, 1H), 7.59 (d, J=7.7 Hz, 1H), 7.72 (d, J=8.6 Hz, 2H), 7.84-7.92 (m, 3H), 8.08 (s, 1H), 8.16 (d, J=5.1 Hz, 1H), 10.44 (s, 1H), 10.93 (s, 1H)

5-(2-(2-Acetamidopyridin-4-yl)methylthiophenyl)-N-(4-chlorophenyl)-1,3,4-thiadiazol-2-amine (Compound 1-(56))

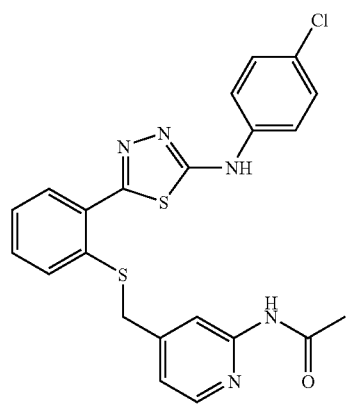

¹H-NMR (300 MHz, DMSO-d₆)

δ 2.05 (s, 3H), 4.25 (s, 2H), 6.97 (d, J=5.1 Hz, 1H), 7.32-7.48 (m, 4H), 7.57 (d, J=7.7 Hz, 1H), 7.71 (d, J=7.9 Hz, 2H), 7.86 (d, J=7.7 Hz, 1H), 8.08 (s, 1H), 8.17 (d, J=5.1 Hz, 1H), 10.65 (s, 1H)

5-(2-(Pyridin-4-yl)methylthiophenyl)-N-(3-trifluoromethylphenyl)-1,3,4-thiadiazol-2-amine (Compound 1-(57))

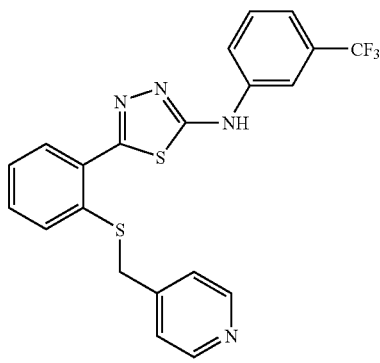

¹H-NMR (300 MHz, DMSO-d₆)

δ 4.27 (s, 2H), 7.29 (d, J=5.9 Hz, 2H), 7.34-7.50 (m, 3H), 7.56-7.64 (m, 2H), 7.80 (m, 1H), 7.89 (dd, J=7.7, 1.5 Hz, 1H), 8.26 (br s, 1H), 8.46 (d, J=5.9 Hz, 2H), 10.88 (s, 1H)

5-(2-(2-Acetamidopyridin-4-yl)methylthiophenyl)-N-(3-trifluoromethylphenyl)-1,3,4-thiadiazol-2-amine (Compound 1-(58))

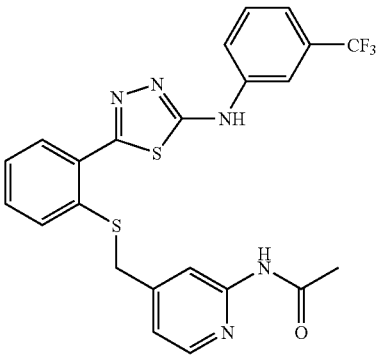

¹H-NMR (300 MHz, DMSO-d₆)

δ 2.04 (s, 3H), 4.25 (s, 2H), 6.97 (d, J=5.1 Hz, 1H), 7.34-7.48 (m, 3H), 7.56-7.64 (m, 2H), 7.80 (t, J=7.7 Hz, 1H), 7.89 (t, J=7.7 Hz, 1H), 8.08 (br s, 1H), 8.16 (d, J=5.1 Hz, 1H), 8.25 (br s, 1H), 10.43 (s, 1H), 10.87 (s, 1H)

5-(2-(2-Acetamidopyridin-4-yl)methylthiophenyl)-N-(3-chlorophenyl)-1,3,4-thiadiazol-2-amine (Compound 1-(59))

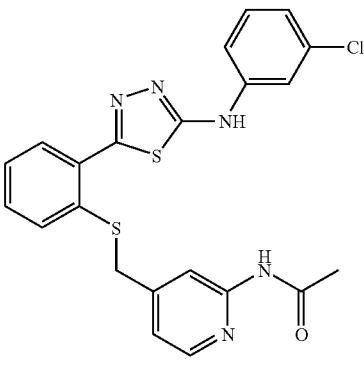

¹H-NMR (300 MHz, DMSO-d₆)

δ 2.04 (s, 3H), 4.25 (s, 2H), 6.97 (d, J=5.1 Hz, 1H), 7.07 (br d, J=8.8 Hz, 1H), 7.34-7.50 (m, 4H), 7.58 (br d, J=7.5 Hz, 1H), 7.87 (dd, J=7.3, 1.5 Hz, 1H), 7.95 (dd, J=2.0, 2.0 Hz, 1H), 8.07 (s, 1H), 8.16 (d, J=5.1 Hz, 1H), 10.43 (s, 1H), 10.72 (s, 1H)

91

5-(2-(Pyridin-4-yl)methylthiophenyl)-N-(4-trifluoromethoxyphenyl)-1,3,4-oxadiazol-2-amine (Compound 1-(60))

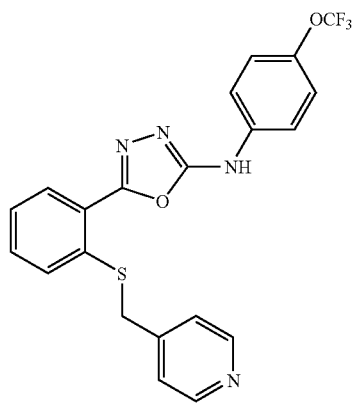

¹H-NMR (300 MHz, DMSO-d₆)

δ 4.37 (s, 2H), 7.32-7.45 (m, 5H), 7.50 (t, J=7.7 Hz, 1H), 7.56 (d, J=7.7 Hz, 1H), 7.71 (d, J=9.0 Hz, 2H), 7.78 (d, J=7.7 Hz, 1H), 8.49 (d, J=5.9 Hz, 2H), 10.93 (s, 1H)

5-(2-(Pyridin-4-yl)methylthiophenyl)-N-(4-trifluoromethoxyphenyl)-1,3,4-thiadiazol-2-amine (Compound 1-(61))

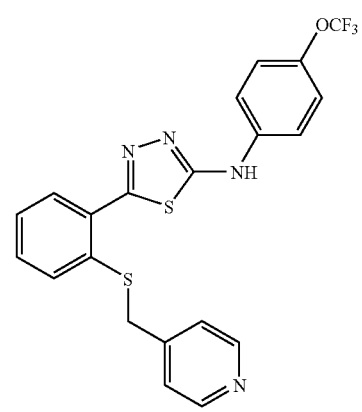

¹H-NMR (300 MHz, DMSO-d₆)

δ 4.26 (s, 2H), 7.29 (d, J=5.1 Hz, 2H), 7.34-7.48 (m, 4H), 7.57 (d, J=7.7 Hz, 1H), 7.78 (d, J=9.0 Hz, 2H), 7.87 (d, J=7.5 Hz, 1H), 8.46 (d, J=5.1 Hz, 2H), 10.70 (s, 1H)

92

5-(2-(2-Acetamidopyridin-4-yl)methylthiophenyl)-N-(4-trifluoromethoxyphenyl)-1,3,4-thiadiazol-2-amine (Compound 1-(62))

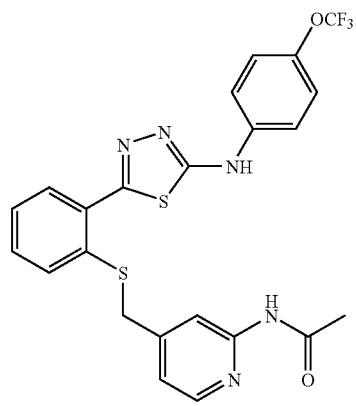

¹H-NMR (300 MHz, DMSO-d₆)

δ 2.05 (s, 3H), 4.25 (s, 2H), 6.97 (d, J=5.1 Hz, 1H), 7.33-7.48 (m, 4H), 7.58 (d, J=7.7 Hz, 1H), 7.78 (d, J=8.8 Hz, 2H), 7.87 (d, J=7.7 Hz, 1H), 8.08 (s, 1H), 8.16 (d, J=5.1 Hz, 1H), 10.43 (s, 1H), 10.70 (s, 1H)

5-(2-(2-Acetamidopyridin-4-yl)methylthiophenyl)-N-(4-trifluoromethoxyphenyl)-1,3,4-oxadiazol-2-amine (Compound 1-(63))

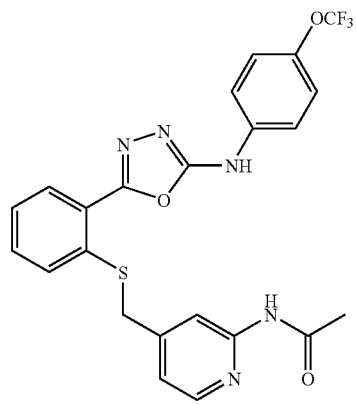

¹H-NMR (300 MHz, DMSO-d₆)

δ 2.06 (s, 3H), 4.35 (s, 2H), 7.13 (br d, J=5.1 Hz, 1H), 7.32-7.43 (m, 3H), 7.49 (br t, J=7.7 Hz, 1H), 7.56 (br d, J=7.7 Hz, 1H), 7.71 (d, J=9.0 Hz, 2H), 7.79 (br d, J=7.8 Hz, 1H), 8.17 (br s, 1H), 8.21 (br d, J=5.1 Hz, 1H), 10.47 (s, 1H), 10.93 (s, 1H)

N-Phenyl-5-(3-(pyridin-4-yl)methylthiothiophen-2-yl)-1,3,4-oxadiazol-2-amine (Compound 1-(64))

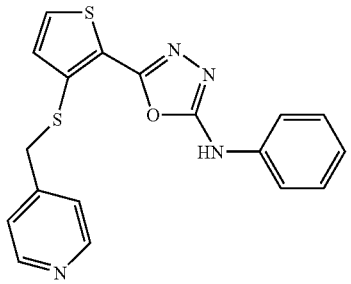

¹H-NMR (300 MHz, DMSO-d$_6$)

δ 10.68 (1H, s), 8.49 (2H, d, J=5.7 Hz), 7.85 (1H, d, J=5.4 Hz), 7.60 (2H, d, J=8.1 Hz), 7.41-7.28 (4H, m), 7.02 (1H, t, J=7.2 Hz), 4.25 (2H, s)

N-Phenyl-5-(3-(pyridin-4-yl)methylthiothiophen-2-yl)-1,3,4-thiadiazol-2-amine (Compound 1-(67))

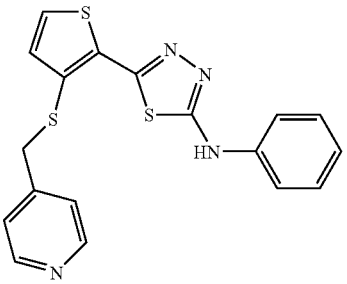

¹H-NMR (300 MHz, DMSO-d$_6$)

δ 10.73 (1H, s), 8.46 (2H, d, J=4.8 Hz), 7.70 (1H, d, J=5.4 Hz), 7.65 (2H, d, J=7.8 Hz), 7.36 (2H, t, J=7.8 Hz), 7.24-7.20 (3H, m), 7.01 (1H, t, J=7.8 Hz), 4.26 (2H, s)

5-(3-(2-Acetamidopyridin-4-yl)methylthiothiophen-2-yl)-N-phenyl-1,3,4-oxadiazol-2-amine (Compound 1-(65))

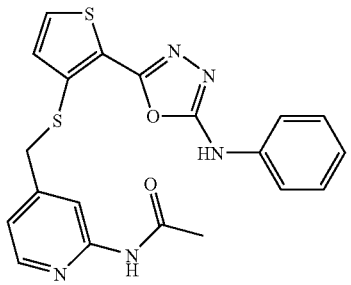

¹H-NMR (300 MHz, DMSO-d$_6$)

δ 10.63 (1H, s), 10.38 (1H, s), 8.16 (1H, d, J=5.2 Hz), 8.08 (1H, s), 7.78 (1H, d, J=5.2 Hz), 7.55 (2H, d, J=7.9 Hz), 7.33 (2H, t, J=7.9 Hz), 7.21 (1H, d, J=5.2 Hz), 7.08-6.97 (2H, m), 4.35 (2H, s), 2.02 (3H, s)

5-(3-(2-Acetamidopyridin-4-yl)methylthiothiophen-2-yl)-N-phenyl-1,3,4-thiadiazole-2-amine (Compound 1-(68))

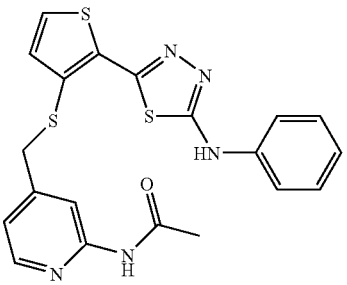

¹H-NMR (300 MHz, DMSO-d$_6$)

δ 10.50 (1H, s), 10.41 (1H, s), 8.14 (1H, d, J=5.2 Hz), 8.02 (1H, s), 7.72 (1H, d, J=5.2 Hz), 7.60 (1H, d, J=7.8 Hz), 7.36 (2H, t, J=7.8 Hz), 7.20 (1H, d, J=5.2 Hz), 7.01 (1H, t, J=7.8 Hz), 6.87 (1H, d, J=5.2 Hz), 4.24 (2H, s), 2.03 (3H, s)

N-Phenyl-5-(3-(quinolin-4-yl)methylthiothiophen-2-yl)-1,3,4-oxadiazol-2-amine (Compound 1-(66))

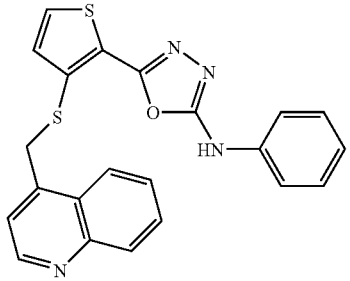

¹H-NMR (300 MHz, DMSO-d$_6$)

δ 10.62 (1H, s), 8.80 (1H, d, J=4.2 Hz), 8.32 (1H, d, J=8.2 Hz), 8.03 (1H, d, J=8.2 Hz), 7.87 (1H, d, J=5.1 Hz), 7.77 (1H, t, J=7.2 Hz), 7.66 (1H, t, J=7.2 Hz), 7.58-7.52 (3H, m), 7.38-7.30 (3H, m), 7.00 (1H, t, J=7.2 Hz), 4.92 (2H, s)

N-Phenyl-5-(3-(quinolin-4-yl)methylthiothiophen-2-yl)-1,3,4-thiadiazol-2-amine (Compound 1-(69))

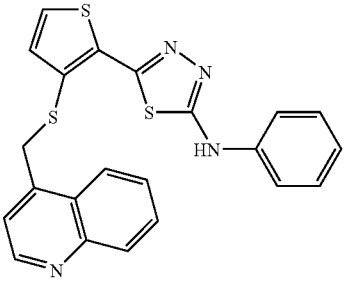

¹H-NMR (300 MHz, DMSO-d$_6$)

δ 10.52 (1H, s), 8.70 (1H, d, J=4.4 Hz), 8.27 (1H, d, J=8.3 Hz), 7.97 (1H, d, J=8.3 Hz), 7.78 (1H, d, J=5.2 Hz), 7.72-7.63 (2H, m), 7.49 (1H, d, J=8.1 Hz), 7.36-7.30 (4H, m), 7.21 (1H, dd, J=5.2 Hz), 7.01 (1H, t, J=7.2 Hz), 4.72 (2H, s)

N-(4-Chlorophenyl)-5-(3-(pyridin-4-yl)methylthio-thiophen-2-yl)-1,3,4-oxadiazol-2-amine (Compound 1-(70))

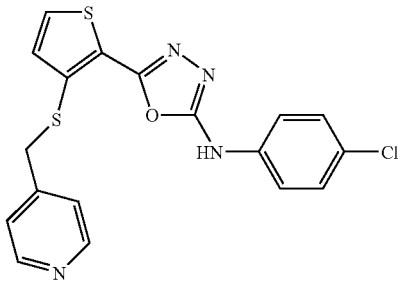

¹H-NMR (300 MHz, DMSO-d₆)

δ 10.90 (1H, s), 8.49 (1H, d, J=5.3 Hz), 7.86 (1H, d, J=5.1 Hz), 7.62 (2H, d, J=8.8 Hz), 7.42-7.40 (5H, m), 7.29 (1H, d, J=5.3 Hz), 4.42 (2H, s)

5-(3-(2-Acetamidopyridin-4-yl)methylthiothiophen-2-yl)-N-(4-chlorophenyl)-1,3,4-oxadiazol-2-amine (Compound 1-(71))

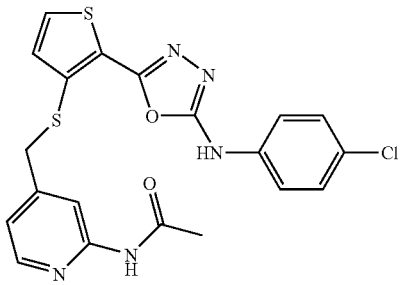

¹H-NMR (300 MHz, DMSO-d₆)

δ 10.90 (1H, s), 10.47 (1H, s), 8.18 (1H, m), 7.85 (1H, d, J=5.3 Hz), 7.63 (2H, d, J=9.0 Hz), 7.40 (2H, d, J=9.0 Hz), 7.19-7.02 (2H, m), 4.39 (2H, s), 2.01 (3H, s)

N-(4-Chlorophenyl)-5-(3-(quinolin-4-yl)methylthio-thiophen-2-yl)-1,3,4-oxadiazol-2-amine (Compound 1-(72))

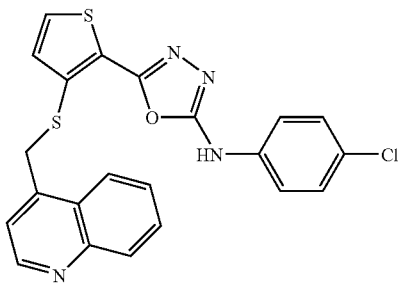

¹H-NMR (300 MHz, DMSO-d₆)

δ 10.79 (1H, s), 8.80 (1H, d, J=4.4 Hz), 8.31 (1H, d, J=7.7 Hz), 8.03 (1H, d, J=8.1 Hz), 7.88 (1H, d, J=5.1 Hz), 7.76 (1H, t, J=7.7 Hz), 7.68-7.57 (3H, m), 7.52 (1H, d, J=4.4 Hz), 7.39-7.37 (3H, m), 4.92 (2H, s)

N-(4-Chlorophenyl)-5-(3-(pyridin-4-yl)methylthio-thiophen-2-yl)-1,3,4-thiadiazol-2-amine (Compound 1-(73))

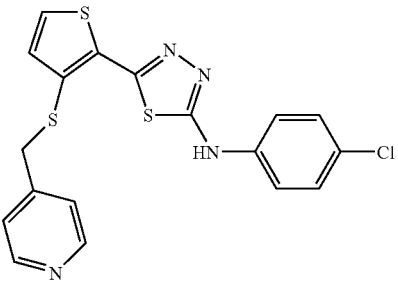

¹H-NMR (300 MHz, DMSO-d₆)

δ 10.63 (1H, s), 8.44 (2H, d, J=4.5 Hz), 7.74 (1H, d, J=5.3 Hz), 7.67-7.66 (2H, m), 7.43-7.38 (2H, m), 7.23-7.21 (3H, m), 4.26 (2H, s)

5-(3-(Pyridin-4-yl)methylthiothiophen-2-yl)-N-(4-trifluoromethoxyphenyl)-1,3,4-oxadiazol-2-amine (Compound 1-(74))

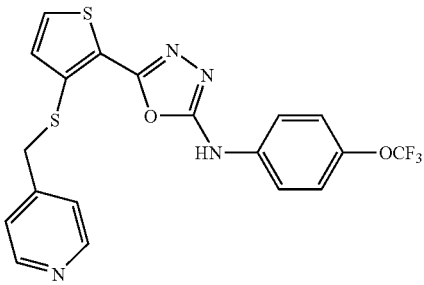

¹H-NMR (300 MHz, DMSO-d₆)

δ 8.49 (2H, d, J=5.3 Hz), 7.78 (1H, d, J=5.1 Hz), 7.70 (2H, d, J=9.0 Hz), 7.39-7.29 (5H, m), 7.30 (1H, d, J=5.1 Hz), 4.43 (2H, s)

5-(3-(2-Acetamidopyridin-4-yl)methylthiothiophen-2-yl)-N-(4-trifluoromethoxyphenyl)-1,3,4-oxadiazol-2-amine (Compound 1-(75))

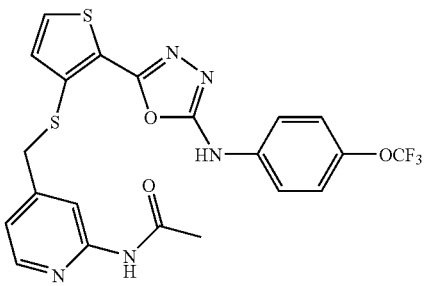

¹H-NMR (300 MHz, DMSO-d₆)

δ 10.92 (1H, s), 10.46 (1H, s), 8.20 (1H, d, J=5.3 Hz), 8.15 (1H, s), 7.86 (1H, d, J=5.4 Hz), 7.70 (2H, d, J=9.3 Hz), 7.38 (2H, d, J=9.3 Hz), 7.29 (1H, d, J=5.4 Hz), 7.10 (1H, d, J=4.6 Hz), 4.42 (2H, s), 2.05 (3H, s)

5-(3-(Quinolin-4-yl)methylthiothiophen-2-yl)-N-(4-trifluoromethoxyphenyl)-1,3,4-oxadiazol-2-amine (Compound 1-(76))

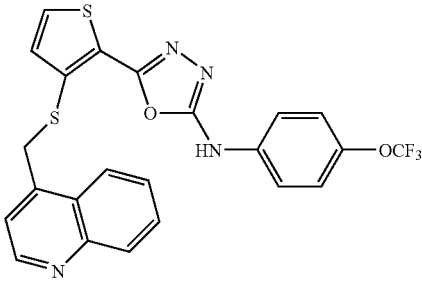

¹H-NMR (300 MHz, DMSO-d₆)

δ 10.86 (1H, s), 8.80 (1H, d, J=4.4 Hz), 8.32 (1H, d, J=8.1 Hz), 8.03 (1H, d, J=8.3 Hz), 7.91-7.89 (1H, m), 7.79-7.63 (4H, m), 7.52 (1H, d, J=4.4 Hz), 7.39-7.32 (3H, m), 4.92 (2H, s)

5-(3-(Pyridin-4-yl)methylthiothiophen-2-yl)-N-(3-trifluoromethylphenyl)-1,3,4-oxadiazol-2-amine (Compound 1-(77))

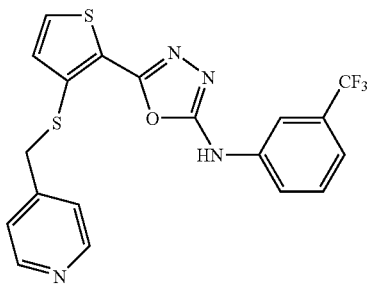

¹H-NMR (300 MHz, DMSO-d₆)

δ 11.11 (1H, s), 8.49 (2H, t, J=5.7 Hz), 8.07 (1H, s), 7.83 (1H, d, J=5.3 Hz), 7.78 (1H, t, J=7.9 Hz), 7.60 (1H, t, J=7.9 Hz), 7.41-7.36 (3H, m), 7.30 (1H, d, J=5.3 Hz), 4.43 (2H, s)

5-(3-(2-Acetamidopyridin-4-yl)methylthiothiophen-2-yl)-N-(3-trifluoromethylphenyl)-1,3,4-oxadiazol-2-amine (Compound 1-(78))

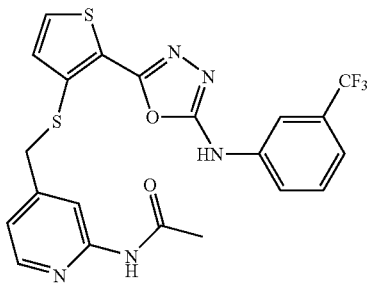

¹H-NMR (300 MHz, DMSO-d₆)

δ 11.11 (1H, s), 10.45 (1H, m), 8.21-8.05 (3H, m), 7.83 (1H, d, J=5.3 Hz), 7.78 (1H, d, J=7.9 Hz), 7.60 (1H, t, J=7.9 Hz), 7.38-7.29 (2H, m), 7.09 (1H, d, J=5.3 Hz), 4.42 (2H, s), 2.05 (3H, s)

5-(3-(Quinolin-4-yl)methylthiothiophen-2-yl)-N-(3-trifluoromethylphenyl)-1,3,4-oxadiazol-2-amine (Compound 1-(79))

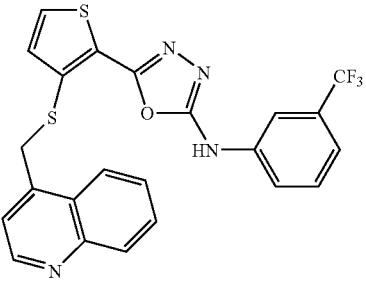

¹H-NMR (300 MHz, DMSO-d₆)

δ 8.79 (1H, d, J=4.4 Hz), 8.30 (1H, d, J=8.3 Hz), 8.04-8.01 (2H, m), 7.88 (1H, d, J=5.3 Hz), 7.78-7.73 (2H, m), 7.65 (1H, t, J=7.8 Hz), 7.57 (1H, t, J=7.8 Hz), 7.51 (1H, d, J=4.4 Hz), 7.38 (1H, d, J=5.3 Hz), 7.33 (1H, d, J=7.8 Hz), 7.37-7.35 (2H, m), 4.92 (2H, s)

5-(3-(Pyridin-4-yl)methylthiothiophen-2-yl)-N-(3-trifluoromethylphenyl)-1,3,4-thiadiazol-2-amine (Compound 1-(80))

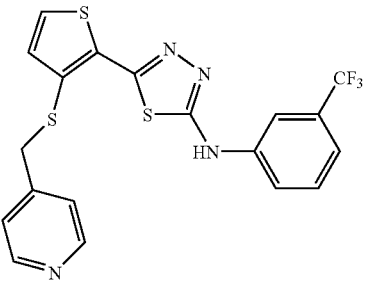

¹H-NMR (300 MHz, DMSO-d₆)

δ 8.44 (1H, d, J=5.3 Hz), 8.23 (1H, s), 7.76-7.74 (2H, m), 7.59 (1H, t, J=7.9 Hz), 7.36 (1H, d, J=7.9 Hz), 7.23 (3H, d, J=5.1 Hz), 7.22 (1H, d, J=5.3 Hz), 4.27 (2H, s)

5-(3-(2-Acetamidopyridin-4-yl)methylthiothiophen-2-yl)-N-(3-trifluoromethylphenyl)-1,3,4-thiadiazol-2-amine (Compound 1-(81))

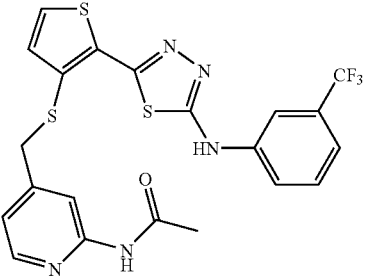

¹H-NMR (300 MHz, DMSO-d₆)

δ 10.85 (1H, s), 10.40 (1H, s), 8.23 (1H, s), 8.13 (1H, d, J=5.1 Hz), 8.01 (1H, s), 7.76-7.74 (2H, m), 7.60 (1H, t, J=7.8

Hz), 7.36 (1H, d, J=7.8 Hz), 7.27 (1H, d, J=5.3 Hz), 6.87 (1H, d, J=5.1 Hz), 4.25 (2H, s), 2.03 (3H, s)

N-(4-Chlorophenyl)-5-(2-(pyridin-4-yl)methylthio-thiophen-3-yl)-1,3,4-oxadiazol-2-amine (Compound 1-(82))

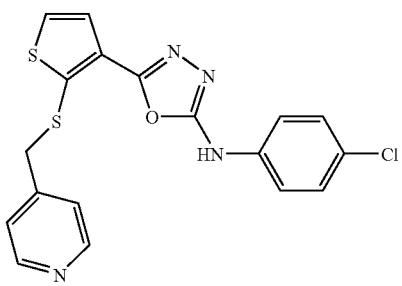

¹H-NMR (300 MHz, DMSO-d₆)

δ 8.44 (2H, d, J=5.7 Hz), 7.68-7.66 (3H, m), 7.44-7.43 (3H, m), 7.26 (2H, d, J=5.7 Hz), 4.32 (2H, s)

5-(2-(2-Acetamidopyridin-4-yl)methylthiothiophen-3-yl)-N-(4-chlorophenyl)-1,3,4-oxadiazol-2-amine (Compound 1-(83))

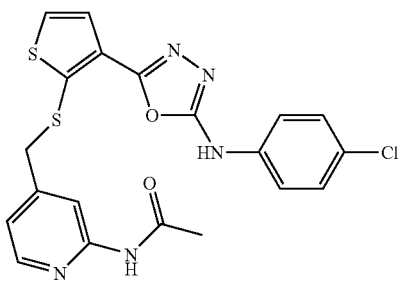

¹H-NMR (300 MHz, DMSO-d₆)

δ 10.83 (1H, s), 10.44 (1H, s), 8.15 (1H, d, J=4.6 Hz), 8.05 (1H, s), 7.68-7.64 (3H, m), 7.43-7.41 (3H, m), 6.95 (1H, d, J=4.6 Hz), 4.30 (2H, s), 2.04 (3H, s)

5-(2-(2-Acetamidopyridin-4-yl)methylthiothiophen-3-yl)-N-(3-trifluoromethylphenyl)-1,3,4-oxadiazol-2-amine (Compound 1-(84))

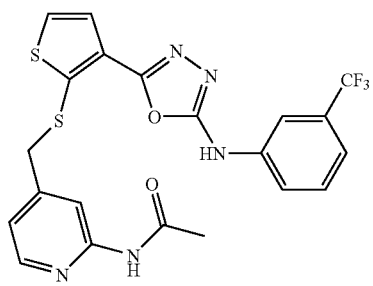

¹H-NMR (300 MHz, DMSO-d₆)

δ 11.07 (1H, s), 10.43 (1H, s), 8.14-8.07 (3H, m), 7.83 (1H, d, J=7.7 Hz), 7.69 (1H, d, J=5.5 Hz), 7.61 (1H, t, J=8.0 Hz), 7.42-7.37 (2H, m), 6.94 (1H, d, J=5.0 Hz), 4.31 (2H, s), 2.03 (3H, s)

5-(3-(Pyridin-4-yl)methylthiothiophen-2-yl)-N-(4-trifluoromethoxyphenyl)-1,3,4-thiadiazol-2-amine (Compound 1-(85))

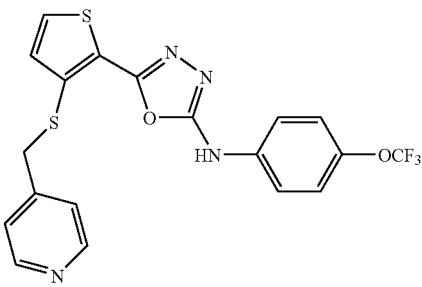

¹H-NMR (300 MHz, DMSO-d₆)

δ 10.69 (1H, s), 8.43 (2H, d, J=5.1 Hz), 7.80-7.70 (2H, m), 7.37 (2H, d, J=8.4 Hz), 7.31 (1H, d, J=5.3 Hz), 7.24 (1H, d, J=5.3 Hz), 7.20 (2H, d, J=5.1 Hz), 4.26 (2H, s)

5-(3-(2-Acetamidopyridin-4-yl)methylthiothiophen-2-yl)-N-(4-trifluoromethoxyphenyl)-1,3,4-thiadiazol-2-amine (Compound 1-(86))

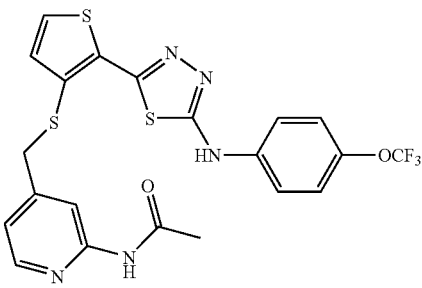

¹H-NMR (300 MHz, DMSO-d₆)

Example 4

5-(2-(2-Cyclopropylaminopyridin-4-yl)methylthiophenyl)-N-phenyl-1,3,4-oxadiazol-2-amine (Compound 1-(87))

To 5-(2-(2-fluoropyridin-4-yl) methylthiophenyl)-N-phenyl-1,3,4-oxadiazol-2-amine (80 mg, 0.19 mmol; Compound 1-(48)) was added cyclopropylamine (200 μL) at room temperature and then the mixture was stirred at 150° C. for 2 hours. The reaction solution was concentrated under a reduced pressure and the residue was purified with a silica gel column chromatography (hexane/ethyl acetate) and to give 5.0 mg (6%) of the titled compound as a colorless solid.

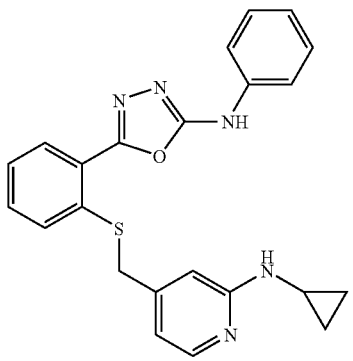

¹H-NMR (300 MHz, DMSO-d₆)
δ 0.50-0.70 (m, 4H), 2.50-2.70 (m, 1H), 4.22 (s, 2H), 6.59 (d, J=5.1 Hz, 1H), 6.61 (s, 1H), 6.76 (br s, 1H), 7.30-7.40 (m, 4H), 7.46-7.58 (m, 2H), 7.62 (d, J=7.7 Hz, 2H), 7.77 (d, J=6.4 Hz, 1H), 7.90 (d, J=5.1 Hz, 1H), 10.70 (s, 1H)

The following Compounds 1-(88) and (89) were obtained by a production method similar to that of Compound 1-(87) using compounds selected from Compounds 1-(48) and (54) and commercially available compounds.

5-(2-(2-Morpholinopyridin-4-yl)methylthiophenyl)-N-phenyl-1,3,4-oxadiazol-2-amine (Compound 1-(88))

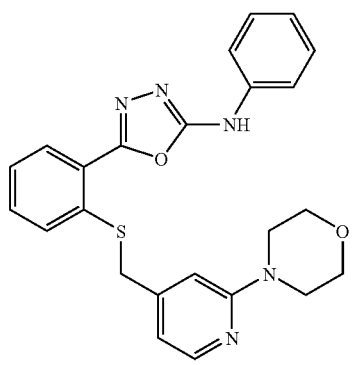

¹H-NMR (300 MHz, DMSO-d₆)
δ 3.35-3.42 (m, 4H), 3.63-3.70 (m, 4H), 4.24 (s, 2H), 6.73 (d, J=5.1 Hz, 1H), 6.87 (s, 1H), 7.02 (t, J=7.3 Hz, 1H), 7.32-7.40 (m, 3H), 7.51 (t, J=7.3 Hz, 1H), 7.56-7.64 (m, 3H), 7.78 (d, J=7.3 Hz, 1H), 8.05 (d, J=5.1 Hz, 1H), 10.69 (s, 1H)

5-(2-(2-Morpholinopyridin-4-yl)methylthiophenyl)-N-phenyl-1,3,4-thiadiazol-2-amine (Compound 1-(89))

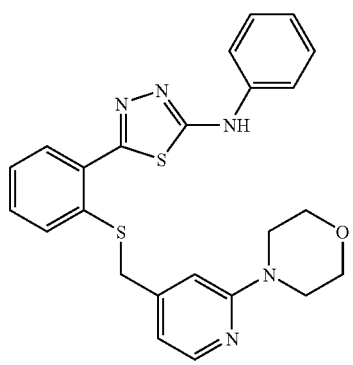

¹H-NMR (300 MHz, DMSO-d₆)
δ 3.30-3.36 (m, 4H), 3.61-3.67 (m, 4H), 4.13 (s, 2H), 6.63 (d, J=5.0 Hz, 1H), 6.68 (s, 1H), 7.02 (t, J=7.3 Hz, 1H), 7.32-7.49 (m, 4H), 7.59 (t, J=7.2 Hz, 1H), 7.66 (d, J=8.4 Hz, 2H), 7.88 (d, J=7.9 Hz, 1H), 8.01 (d, J=5.1 Hz, 1H), 10.52 (s, 1H)

Example 5

5-(2-(2-Aminopyridin-4-yl)methylthiopyridin-3-yl)-N-phenyl-1,3,4-oxadiazol-2-amine hydrochloride (Compound 1-(90))

To a solution of 5-(2-(2-t-butoxycarbonylaminopyridin-4-yl) methylthiopyridin-3-yl)-N-phenyl-1,3,4-oxadiazol-2-amine (140 mg, 0.30 mmol; Compound 1-(7)) in dioxane (1.0 mL) was added a 4M dioxane solution of hydrogen chloride (1.0 mL, 4.0 mmol) at room temperature and then the mixture was stirred over night. The precipitated solid was filtered off to give 130 mg (quantitative) of the titled compound as a colorless solid.

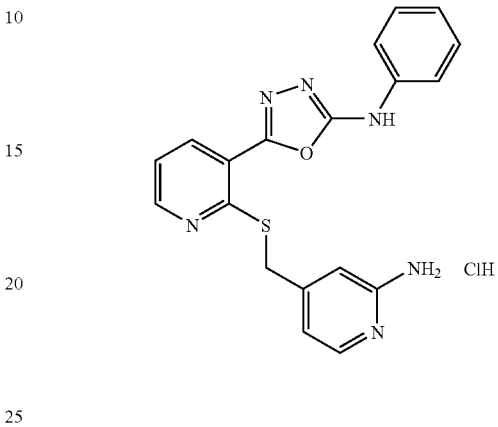

¹H-NMR (300 MHz, DMSO-d₆)
δ 4.51 (s, 2H), 6.93 (t, J=6.6 Hz, 1H), 7.00-7.10 (m, 3H), 7.34-7.44 (m, 3H), 7.63 (d, J=7.7 Hz, 2H), 7.86 (d, J=6.8 Hz, 1H), 8.00 (br s, 1H), 8.13 (dd, J=7.9, 1.7 Hz, 1H), 8.60 (dd, J=4.8, 1.7 Hz, 1H), 10.85 (s, 1H), 13.52 (br s, 1H)

The following Compounds 1-(91) and (92) were obtained by a production method similar to that of Compound 1-(90) using compounds selected from Compounds 1-(8) and (9) and commercially available compounds.

5-(2-(2-Aminopyridin-4-yl)methylthiopyridin-3-yl)-N-(4-chlorophenyl)-1,3,4-oxadiazol-2-amine hydrochloride (Compound 1-(91))

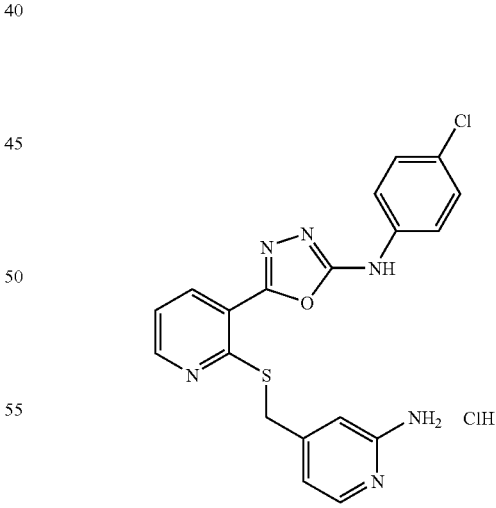

¹H-NMR (300 MHz, DMSO-d₆)
δ 4.51 (s, 2H), 6.92 (m, 1H), 7.06 (s, 1H), 7.39-7.43 (m, 3H), 7.66 (d, J=9.0 Hz, 2H), 7.86 (d, J=6.6 Hz, 1H), 8.00 (br s, 2H), 8.13 (m, 1H), 8.60 (m, 1H), 11.06 (s, 1H), 13.48 (br s, 1H)

5-(2-(2-Aminopyridin-4-yl)methylthiopyridin-3-yl)-N-(3-trifluoromethylphenyl)-1,3,4-oxadiazol-2-amine hydrochloride (Compound 1-(92))

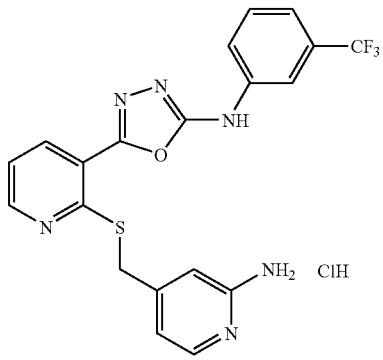

¹H-NMR (300 MHz, DMSO-d₆)
δ 4.52 (s, 2H), 6.93 (d, J=6.6 Hz, 1H), 7.06 (s, 1H), 7.37-7.50 (m, 2H), 7.63 (t, J=7.9 Hz, 1H), 7.82-7.89 (m, 2H), 8.00 (br s, 2H), 8.10-8.16 (m, 2H), 8.62 (dd, J=4.8, 1.7 Hz, 1H), 11.30 (s, 1H), 13.48 (br s, 1H)

Example 6

5-(2-(Quinolin-4-yl)methoxyphenyl)-N-(3-trifluoromethylphenyl)-1,3,4-oxadiazol-2-amine (Compound 1-(93))

To a solution of 2-(5-(3-trifluoromethylphenylamino)-1,3,4-oxadiazol-2-yl) phenol (100 mg, 0.31 mmol; Reference Compound 9-(1)) and 4-chloromethylquinoline (55 mg, 0.31 mmol) in N,N-dimethylformamide (1.0 mL) was added potassium carbonate (86 mg, 0.62 mmol) at room temperature and then the mixture was stirred at 60° C. over night. The reaction solution was cooled to a room temperature and diluted with ethyl acetate (100 mL). The ethyl acetate solution was washed with a saturated brine solution (30 mL), dried over anhydrous sodium sulfate and concentrated under a reduced pressure. The residue was purified with a silica gel column chromatography (hexane/ethyl acetate) to give 39 mg (27%) of the titled compound as a colorless solid.

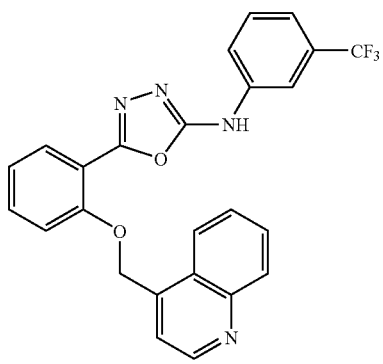

¹H-NMR (300 MHz, DMSO-d₆)
δ 5.90 (s, 2H), 6.94 (t, J=7.7 Hz, 1H), 7.03 (d, J=8.3 Hz, 1H), 7.39 (m, 1H), 7.49 (d, J=4.6 Hz, 1H), 7.50-7.58 (m, 2H), 7.62 (t, J=7.9 Hz, 1H), 7.72 (m, 1H), 7.80-7.88 (m, 2H), 8.08 (d, J=8.6 Hz, 1H), 8.17 (br s, 1H), 8.25 (d, J=8.3 Hz, 1H), 8.81 (d, J=4.6 Hz, 1H), 10.07 (s, 1H)

The following Compound 1-(94) was obtained by a production method similar to that of Compound 1-(93) using compounds selected from Reference Compounds 9-(1), 2-acetamido-4-methanesulfonyloxymethylpyridine (CAS#864461-12-1; WO2005/085201) and commercially available compounds.

5-(2-(2-Acetamidopyridin-4-yl)methoxyphenyl)-N-(3-trifluoromethylphenyl)-1,3,4-oxadiazol-2-amine (Compound 1-(94))

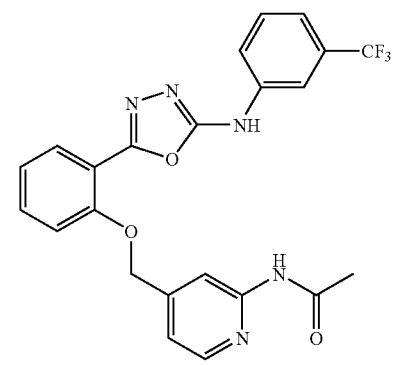

¹H-NMR (300 Mz, DMSO-d₆)
δ 2.05 (s, 3H), 5.37 (s, 2H), 6.94-6.98 (m, 1H), 7.04 (d, J=8.3 Hz, 1H), 7.09 (dd, J=5.1, 2.3 Hz, 1H), 7.40 (dd, J=8.0, 1.7 Hz, 1H), 7.55-7.59 (m, 2H), 7.65 (dd, J=8.1, 7.5 Hz, 1H), 7.81 (d, J=5.9 Hz, 1H), 8.07 (s, 1H), 8.11 (s, 1H), 8.23 (d, J=5.1 Hz, 1H), 10.07 (s, 1H), 10.50 (s, 1H)

Preparation Examples

Hereinafter, typical preparation examples of the present compound will be described.

Tablet

| Prescription 1 (in 100 mg) | |
| --- | --- |
| Present compound | 1 mg |
| Lactose | 66.4 mg |
| Cornstarch | 20 mg |
| Carboxymethyl cellulose calcium | 6 mg |
| Hydroxypropyl cellulose | 4 mg |
| Magnesium stearate | 0.6 mg |

A tablet of the above-mentioned formulation is coated using 2 mg of a coating agent (for example, a conventional coating agent such as hydroxypropylmethyl cellulose, macrogol, or a silicone resin), whereby an objective coat tablet can be obtained. In addition, a desired tablet can be obtained by appropriately changing the type and amount of the present compound and additives.

Capsule

| Prescription 2 (in 150 mg) | |
| --- | --- |
| Present compound | 5 mg |
| Lactose | 145 mg |

A desired capsule can be obtained by appropriately changing the mixture ratio of the present compound and lactose.

Eye Drop

| Prescription 3 (in 100 ml) | |
|---|---|
| Present compound | 100 mg |
| Sodium chloride | 900 mg |
| Polysorbate 80 | 200 mg |
| Sodium hydroxide | q.s. |
| Hydrochloric acid | q.s. |
| Sterile purified water | q.s. |

A desired eye drop can be obtained by appropriately changing the type and amount of the present compound and additives.

[Pharmacological Tests]
Evaluation Test of Inhibitory Effect of Tyrosine Kinase (KDR) Activity As one of the widely-used methods of evaluating inhibitory effect of tyrosine kinase (KDR) activity by drugs, the ELISA method has been reported. The inhibitory effect of tyrosine kinase (KDR) activity of each of the present compounds was evaluated using the commercially available kit (purchased from CARNABIO SCIENCE Co. Ltd. JAPAN) for evaluating inhibitory effect of tyrosine kinase (KDR) activity.

(Preparation of Test Compound Solution)

Each test compound (2 mg) were dissolved in dimethyl sulfoxide (hereinafter abbreviated as DMSO), and the 2 mg/ml stock solution were prepared. Each obtained solution was diluted with 8 μL of DMSO. Each solution (0.4 mg/ml compound) was diluted 25 times with assay buffer to give the test compound solution. For the vehicle, 4% DMSO-Assay Buffer solution was prepared.

(Preparation of ATP/Substrate Solution)

Thaw commercially available ATP/Substrate (purchased from CARNABIO SCIENCE Co. Ltd. JAPAN), then 250 μL of it was added to 1 mL of assay buffer to give ATP/substrate solution. ATP/substrate solution was kept on ice before use.

(Preparation of Enzyme Solution)

7 μL of commercially available tyrosine kinase (purchased from CARNABIO SCIENCE Co. Ltd. JAPAN) was added to 2.793 mL of assay buffer to give enzyme solution. Enzyme solution was kept on ice before use.

(Preparation of Blocking Buffer)

BSA (Sigma, A-7030) was dissolved with wash buffer (50 mM Tris-HCl (pH7.5), 150 mM NaCl, 0.2% Tween-20) to give x100 BSA solution, and the solution was kept at −80° C. Thaw 400 μL of x100 BSA solution before use, it was added to 40 mL of wash buffer to give blocking buffer.

(Preparation of Detection Mixture)

40 μL of commercially available HRP-conjugated antibody (purchased from CARNABIO SCIENCE Co. Ltd. JAPAN) was added to 12 mL of blocking buffer to give detection mixture.

(Method of Test and Method of Measurement)

1) Add 10 μL of each test compound solution, 10 μL of ATP/substrate solution and 20 μL of enzyme solution to each well of ELISA plate (streptavidin-coated 96-well plate, PerkinElmer, 4009-0010). Incubate for 1 hour at room temperature (4 mg/L test compound solution, 15 mM Tris-HCl (pH7.5), 0.01% Tween 20, 2 mM DTT, concentration of substrate: 250 nM, 1 μM ATP, 5 mM Mg). For the vehicle, the above mentioned 4% DMSO-assay buffer solution was added instead of test compound solution.

2) Aspirate each well and wash with wash buffer, repeating the process three times for four washes.

3) Add 200 μL of blocking buffer to each well and cover the plate and incubate for 30 minutes.

4) Aspirate each well, add 100 μL of detection mixture to each well and incubate the plate for 30 minutes.

5) Aspirate each well and wash with wash buffer 4 times.

6) Add 100 μL of color reagent to each well. Incubate for 5 minutes and then add 0.1 M $H_2SO_4$ to each well.

7) Measure the absorbance of each well, using a plate reader set to 450 nM.

(Calculation of Kinase Inhibition Rate)

Rate of the reaction positive control well with kinase was considered 0% inhibition, rate of the reaction negative control well with assay buffer instead of kinase was considered 100% inhibition, and so the inhibition rates of test compound well were calculated based on the absorbance of them.

(Calculation Equation)

A: Absorbance of the reaction positive control well

B: Absorbance of the reaction negative control well

C: Absorbance of the test compound well tyrosine kinase inhibition rates (%)=100 [1-(C-A)/(B-A)]

(Test Results and Discussion)

As an example of the test results, Table 1 shows the tyrosine kinase inhibition rates (% inhibition) of the test compounds (Compound 1-1, Compound 1-3, Compound 1-4, Compound 1-6, Compound 1-7, Compound 1-10, Compound 1-13, Compound 1-14, Compound 1-16, Compound 1-17, Compound 1-18, Compound 1-20, Compound 1-21, Compound 1-32, Compound 1-33, Compound 1-34, Compound 1-35, Compound 1-36, Compound 1-37, Compound 1-38, Compound 1-39, Compound 1-40, Compound 1-41, Compound 1-45, Compound 1-46, Compound 1-47, Compound 1-91, Compound 1-92.

TABLE 1

| Compound | % inhibition |
|---|---|
| 1-1 | 55 |
| 1-3 | 80 |
| 1-4 | 75 |
| 1-6 | 65 |
| 1-7 | 60 |
| 1-10 | 76 |
| 1-13 | 72 |
| 1-14 | 90 |
| 1-16 | 95 |
| 1-17 | 94 |
| 1-18 | 99 |
| 1-20 | 86 |
| 1-21 | 93 |
| 1-32 | 55 |
| 1-33 | 95 |
| 1-34 | 86 |
| 1-35 | 58 |
| 1-36 | 68 |
| 1-37 | 84 |
| 1-38 | 53 |
| 1-39 | 43 |
| 1-40 | 88 |
| 1-41 | 82 |
| 1-45 | 91 |
| 1-46 | 98 |
| 1-47 | 75 |
| 1-91 | 86 |
| 1-92 | 98 |

As shown in Table 1, the present compounds exhibited an excellent tyrosine kinase inhibitory action. Accordingly, the present compounds have an excellent angiogenesis inhibitory effect.

INDUSTRIAL APPLICABILITY

The present compound is useful as therapeutic agents for diseases associated with neovascularization, such as therapeutic agents for cancer, rheumatoid arthritis, age-related macular degeneration, diabetic retinopathy, retinopathy of prematurity, retinal vein occlusion, polypoidal choroidal vasculopathy, diabetic macular edema, plaque psoriasis, atherosclerosis, and the like.

The invention claimed is:

1. A compound represented by the following formula (I) or a salt thereof:

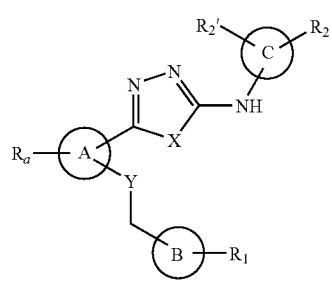

(I)

wherein the ring A represents a benzene ring, a thiophene ring, or a pyridine ring;
$R_a$ represents a hydrogen atom, a halogen atom, an alkyl group, or an alkoxy group;
the ring B represents a pyridine ring, a pyrimidine ring, or a quinoline ring;
the ring C represents a benzene ring, a pyridine ring, a quinoline ring, or an isoquinoline ring;
X represents an oxygen atom or a sulfur atom; when X is an oxygen atom, Y represents a sulfur atom or an oxygen atom; when X is a sulfur atom, Y represents a sulfur atom;
$R_1$ represents a hydrogen atom, a halogen atom, an amino group, a cycloalkylamino group, an alkylcarbonylamino group, an alkyloxycarbonylamino group, an alkylaminocarbonyl group, or a non-aromatic heterocyclic group;
$R_2$ and $R_2'$ are the same or different and represent a hydrogen atom, a halogen atom, an alkyl group, a halogeno-alkyl group, or a halogeno-alkoxy group.

2. A compound represented by the following formula (I') or a salt thereof:

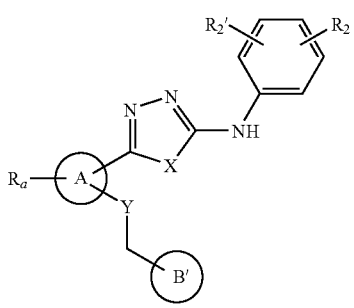

(I')

wherein the ring A represents

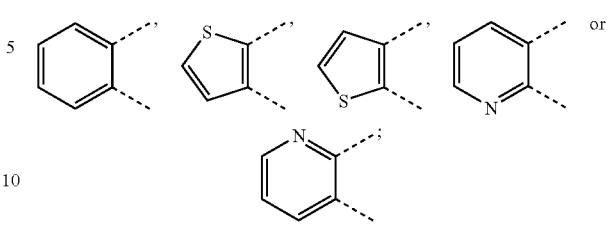

$R_a$ represents a hydrogen atom, a halogen atom, an alkyl group, or an alkoxy group;
the ring B' represents

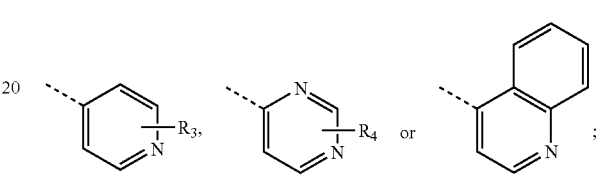

X represents an oxygen atom or a sulfur atom; when X is an oxygen atom, Y represents a sulfur atom or an oxygen atom; when X is a sulfur atom, Y represents a sulfur atom;
$R_2$ and $R_2'$ are the same or different and represent a hydrogen atom, a halogen atom, an alkyl group, a halogeno-alkyl group, or a halogeno-alkoxy group;
$R_3$ represents a hydrogen atom, a halogen atom, an amino group, a cycloalkylamino group, an alkylcarbonylamino group, an alkyloxycarbonylamino group, an alkylaminocarbonyl group, or a non-aromatic heterocyclic group; and
$R_4$ represents a hydrogen atom, a halogen atom, an amino group, a cycloalkylamino group, an alkylcarbonylamino group, an alkyloxycarbonylamino group, an alkylaminocarbonyl group, or a non-aromatic heterocyclic group.

3. The compound or the salt thereof according to claim 2, wherein, in the formula (I'),
the ring A represents

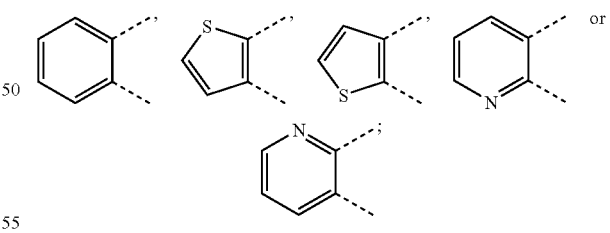

$R_a$ represents a hydrogen atom, a halogen atom, or an alkoxy group;
the ring B' represents

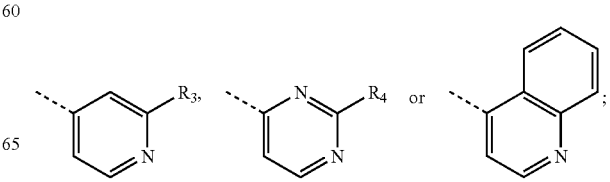

X represents an oxygen atom or a sulfur atom; when X is an oxygen atom, Y represents a sulfur atom or an oxygen atom; when X is a sulfur atom, Y represents a sulfur atom;

$R_2$ and $R_2'$ are the same or different and represent a hydrogen atom, a halogen atom, an alkyl group, a halogeno-alkyl group, or a halogeno-alkoxy group;

$R_3$ represents a hydrogen atom, a halogen atom, an amino group, a cycloalkylamino group, an alkylcarbonylamino group, an alkyloxycarbonylamino group, an alkylaminocarbonyl group, or a non-aromatic heterocyclic group; and $R_4$ represents a hydrogen atom or an amino group.

4. The compound or the salt thereof according to claim 3, wherein, in the formula (I'), the ring A represents

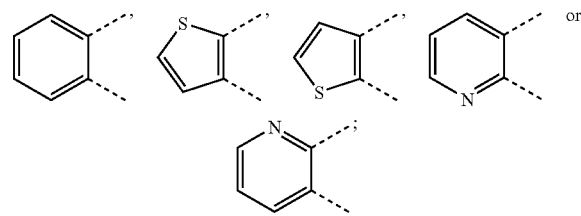

$R_a$ represents a hydrogen atom, a bromine atom, or a methoxy group;

the ring B' represents

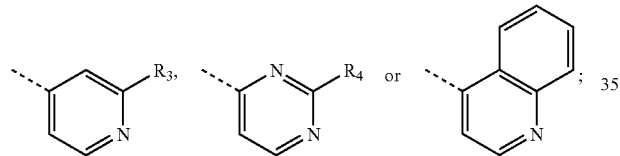

X represents an oxygen atom or a sulfur atom; when X is an oxygen atom, Y represents a sulfur atom or an oxygen atom; when X is a sulfur atom, Y represents a sulfur atom;

$R_2$ and $R_2'$ are the same or different and represent a hydrogen atom, a bromine atom, tert-butyl group, a trifluoromethyl group, or a trifluoromethoxy group;

$R_3$ represents a hydrogen atom, a fluorine atom, an amino group, a cyclopropylamino group, a methylcarbonylamino group, a tert-butoxycarbonylamino group, a methylaminocarbonyl group, or a morpholin-4-yl group; and $R_4$ represents a hydrogen atom or an amino group.

5. A compound or a salt thereof, wherein the compound is selected from the group consisting of N-phenyl-5-(2-(pyridin-4-yl)methoxyphenyl)-1,3,4-oxadiazol-2-amine,
N-(4-chlorophenyl)-5-(2-(pyridin-4-yl)methoxyphenyl)-1,3,4-oxadiazol-2-amine,
5-(2-(pyridin-4-yl)methoxyphenyl)-N-(3-trifluoromethylphenyl)-1,3,4-oxadiazol-2-amine,
N-phenyl-5-(2-(quinolin-4-yl)methoxyphenyl)-1,3,4-oxadiazol-2-amine,
N-phenyl-5-(3-(pyridin-4-yl)methoxythiophen-2-yl)-1,3,4-oxadiazol-2-amine,
5-(2-(2-acetamidopyridin-4-yl)methoxyphenyl)-N-phenyl-1,3,4-oxadiazol-2-amine,
5-(2-(2-t-butoxycarbonylaminopyridin-4-yl)methylthiopyridin-3-yl)-N-phenyl-1,3,4-oxadiazol-2-amine,
5-(2-(quinolin-4-yl)methoxyphenyl)-N-(3-trifluoromethylphenyl)-1,3,4-oxadiazol-2-amine,
5-(2-(2-acetamidopyridin-4-yl)methoxyphenyl)-N-(3-trifluoromethylphenyl)-1,3,4-oxadiazol-2-amine,
N-phenyl-5-(2-(pyridin-4-yl)methylthiophenyl)-1,3,4-oxadiazol-2-amine,
5-(2-(pyridin-4-yl)methylthiophenyl)-N-(3-trifluoromethylphenyl)-1,3,4-oxadiazol-2-amine,
N-(4-t-butylphenyl)-5-(2-(pyridin-4-yl)methylthiophenyl)-1,3,4-oxadiazol-2-amine,
N-phenyl-5-(2-(pyridin-4-yl)methylthiophenyl)-1,3,4-thiadiazol-2-amine,
N-(4-chlorophenyl)-5-(2-(pyridin-4-yl)methylthiophenyl)-1,3,4-thiadiazol-2-amine,
N-(3-chlorophenyl)-5-(2-(pyridin-4-yl)methylthiophenyl)-1,3,4-thiadiazol-2-amine,
5-(2-(pyridin-4-yl)methylthiophenyl)-N-(4-trifluoromethylphenyl)-1,3,4-thiadiazol-2-amine,
N-(4-t-butylphenyl)-5-(2-(pyridin-4-yl)methylthiophenyl)-1,3,4-thiadiazol-2-amine,
N-phenyl-5-(2-(quinolin-4-yl)methylthiophenyl)-1,3,4-oxadiazol-2-amine,
N-(4-chlorophenyl)-5-(2-(pyridin-4-yl)methylthiophenyl)-1,3,4-oxadiazol-2-amine,
N-(4-chlorophenyl)-5-(2-(quinolin-4-yl)methylthiophenyl)-1,3,4-oxadiazol-2-amine,
5-(2-(quinolin-4-yl)methylthiophenyl)-N-(3-trifluoromethylphenyl)-1,3,4-oxadiazol-2-amine,
5-(2-(2-acetamidopyridin-4-yl)methylthiophenyl)-N-phenyl-1,3,4-oxadiazol-2-amine,
5-(2-(2-acetamidopyridin-4-yl)methylthiophenyl)-N-(4-chlorophenyl)-1,3,4-oxadiazol-2-amine,
5-(2-(2-acetamidopyridin-4-yl)methylthiophenyl)-N-(3-trifluoromethylphenyl)-1,3,4-oxadiazol-2-amine,
5-(2-(2-aminopyrimidin-4-yl)methylthiophenyl)-N-phenyl-1,3,4-oxadiazol-2-amine,
5-(2-(2-fluoropyridin-4-yl)methylthiophenyl)-N-phenyl-1,3,4-oxadiazol-2-amine,
N-phenyl-5-(2-(quinolin-4-yl)methylthiophenyl)-1,3,4-thiadiazol-2-amine,
N-(4-chlorophenyl)-5-(2-(quinolin-4-yl)methylthiophenyl)-1,3,4-thiadiazol-2-amine,
N-(3-chlorophenyl)-5-(2-(quinolin-4-yl)methylthiophenyl)-1,3,4-thiadiazol-2-amine,
5-(2-(quinolin-4-yl)methylthiophenyl)-N-(4-trifluoromethylphenyl)-1,3,4-thiadiazol-2-amine,
5-(2-(2-acetamidopyridin-4-yl)methylthiophenyl)-N-phenyl-1,3,4-thiadiazol-2-amine,
5-(2-(2-fluoropyridin-4-yl)methylthiophenyl)-N-phenyl-1,3,4-thiadiazol-2-amine,
5-(2-(2-cyclopropylaminopyridin-4-yl)methylthiophenyl)-N-phenyl-1,3,4-oxadiazol-2-amine,
5-(2-(2-morpholinopyridin-4-yl)methylthiophenyl)-N-phenyl-1,3,4-oxadiazol-2-amine,
5-(2-(2-morpholinopyridin-4-yl)methylthiophenyl)-N-phenyl-1,3,4-thiadiazol-2-amine,
5-(2-(2-t-butoxycarbonylaminopyridin-4-yl)methylthiopyridin-3-yl)-N-(4-chlorophenyl)-1,3,4-oxadiazol-2-amine,
5-(2-(2-t-butoxycarbonylaminopyridin-4-yl)methylthiopyridin-3-yl)-N-(3-trifluoromethylphenyl)-1,3,4-oxadiazol-2-amine,
N-phenyl-5-(2-(pyridin-4-yl)methylthiopyridin-3-yl)-1,3,4-oxadiazol-2-amine,
N-(4-chlorophenyl)-5-(2-(pyridin-4-yl)methylthiopyridin-3-yl)-1,3,4-oxadiazol-2-amine, 5-(2-(pyridin-4-yl)methylthiopyridin-3-yl)-N-(3-trifluoromethylphenyl)-1,3,4-oxadiazol-2-amine,
N-phenyl-5-(2-(quinolin-4-yl)methylthiopyridin-3-yl)-1,3,4-oxadiazol-2-amine,
N-(4-chlorophenyl)-5-(2-(quinolin-4-yl)methylthiopyridin-3-yl)-1,3,4-oxadiazol-2-amine,
5-(2-(quinolin-4-yl)methylthiopyridin-3-yl)-N-(3-trifluoromethylphenyl)-1,3,4-oxadiazol-2-amine,
5-(2-(2-acetamidopyridin-4-yl)methylthiopyridin-3-yl)-N-phenyl-1,3,4-oxadiazol-2-amine,
5-(2-(2-acetamidopyridin-4-yl)methylthiopyridin-3-yl)-N-(4-chlorophenyl)-1,3,4-oxadiazol-2-amine,
5-(2-(2-acetamidopyridin-4-yl)methylthiopyridin-3-yl)-N-(3-trifluoromethylphenyl)-1,3,4-oxadiazol-2-amine,
5-(2-(3-methylaminocarbonylpyridin-4-yl)methylthiopyridin-3-yl)-N-phenyl-1,3,4-oxadiazol-2-amine,
N-(4-chlorophenyl)-5-(2-(2-methylaminocarbonylpyridin-4-yl)methylthiopyridin-3-yl)-1,3,4-oxadiazol-2-amine,
5-(2-(2-methylaminocarbonylpyridin-4-yl)methylthiopyridin-3-yl)-N-(3-trifluoromethylphenyl)-1,3,4-oxadiazol-2-amine,
N-(2-chloro-5-trifluoromethylphenyl)-5-(2-(pyridin-4-yl)methoxyphenyl)-1,3,4-oxadiazol-2-amine,
N-(4-t-butylphenyl)-5-(2-(pyridin-4-yl)methoxyphenyl)-1,3,4-oxadiazol-2-amine,
5-(3-(pyridin-4-yl)methoxythiophen-2-yl)-N-(3-trifluoromethylphenyl)-1,3,4-oxadiazol-2-amine,
5-(2-(2-aminopyridin-4-yl)methylthiopyridin-3-yl)-N-phenyl-1,3,4-oxadiazol-2-amine hydrochloride,
5-(2-(2-aminopyridin-4-yl)methylthiopyridin-3-yl)-N-(4-chlorophenyl)-1,3,4-oxadiazol-2-amine hydrochloride,
5-(2-(2-aminopyridin-4-yl)methylthiopyridin-3-yl)-N-(3-trifluoromethylphenyl)-1,3,4-oxadiazol-2-amine hydrochloride,
5-(5-bromo-2-(pyridin-4-yl)methoxyphenyl)-N-phenyl-1,3,4-oxadiazol-2-amine,
5-(5-methoxy-2-(pyridin-4-yl)methoxyphenyl)-N-phenyl-1,3,4-oxadiazol-2-amine,
N-phenyl-5-(3-(pyridin-4-yl)methoxypyridin-2-yl)-1,3,4-oxadiazol-2-amine,
5-(3-(pyridin-4-yl)methoxypyridin-2-yl)-N-(3-trifluoromethylphenyl)-1,3,4-oxadiazol-2-amine,
5-(2-(2-acetamidopyridin-4-yl)methylthiopyridin-3-yl)-N-(4-trifluoromethoxyphenyl)-1,3,4-oxadiazol-2-amine,
N-(4-(2-(5-phenylamino-1,3,4-oxadiazol-2-yl)thiophen-3-yloxy)methylpyridin-2-yl)acetamide,
N-(4-(2-(5-(3-trifluoromethylphenyl)amino-1,3,4-oxadiazol-2-yl)thiophen-3-yl)oxymethylpyridin-2-yl)acetamide,
5-(2-(2-acetamidopyridin-4-yl)methylthiophenyl)-N-(4-trifluoromethylphenyl)-1,3,4-thiadiazol-2-amine,
5-(2-(2-acetamidopyridin-4-yl)methylthiophenyl)-N-(4-chlorophenyl)-1,3,4-thiadiazol-2-amine,
5-(2-(pyridin-4-yl)methylthiophenyl)-N-(3-trifluoromethylphenyl)-1,3,4-thiadiazol-2-amine,
5-(2-(2-acetamidopyridin-4-yl)methylthiophenyl)-N-(3-trifluoromethylphenyl)-1,3,4-thiadiazol-2-amine,
5-(2-(2-acetamidopyridin-4-yl)methylthiophenyl)-N-(3-chlorolphenyl)-1,3,4-thiadiazol-2-amine,
5-(2-(pyridin-4-yl)methylthiophenyl)-N-(4-trifluoromethoxyphenyl)-1,3,4-oxadiazol-2-amine,
5-(2-(pyridin-4-yl)methylthiophenyl)-N-(4-trifluoromethoxyphenyl)-1,3,4-thiadiazol-2-amine,
5-(2-(2-acetamidopyridin-4-yl)methylthiophenyl)-N-(4-trifluoromethoxyphenyl)-1,3,4-thiadiazol-2-amine,
5-(2-(2-acetamidopyridin-4-yl)methylthiophenyl)-N-(4-trifluoromethoxyphenyl)-1,3,4-oxadiazol-2-amine,
N-phenyl-5-(3-(pyridin-4-yl)methylthiothiophen-2-yl)-1,3,4-oxadiazol-2-amine,
5-(3-(2-acetamidopyridin-4-yl)methylthiothiophen-2-yl)-N-phenyl-1,3,4-oxadiazol-2-amine,
N-phenyl-5-(3-(quinolin-4-yl)methylthiothiophen-2-yl)-1,3,4-oxadiazol-2-amine,
N-phenyl-5-(3-(pyridin-4-yl)methylthiothiophen-2-yl)-1,3,4-thiadiazol-2-amine,
5-(3-(2-acetamidopyridin-4-yl)methylthiothiophen-2-yl)-N-phenyl-1,3,4-thiadiazol-2-amine,
N-phenyl-5-(3-(quinolin-4-yl)methylthiothiophen-2-yl)-1,3,4-thiadiazol-2-amine,
N-(4-chlorophenyl)-5-(3-(pyridin-4-yl)methylthiothiophen-2-yl)-1,3,4-oxadiazol-2-amine,
5-(3-(2-acetamidopyridin-4-yl)methylthiothiophen-2-yl)-N-(4-chlorophenyl)-1,3,4-oxadiazol-2-amine,
N-(4-chlorophenyl)-5-(3-(quinolin-4-yl)methylthiothiophen-2-yl)-1,3,4-oxadiazol-2-amine,
N-(4-chlorophenyl)-5-(3-(pyridin-4-yl)methylthiothiophen-2-yl)-1,3,4-thiadiazol-2-amine,
5-(3-(pyridin-4-yl)methylthiothiophen-2-yl)-N-(4-trifluoromethoxyphenyl)-1,3,4-oxadiazol-2-amine,
5-(3-(2-acetamidopyridin-4-yl)methylthiothiophen-2-yl)-N-(4-trifluoromethoxyphenyl)-1,3,4-oxadiazol-2-amine,
5-(3-(quinolin-4-yl)methylthiothiophen-2-yl)-N-(4-trifluoromethoxyphenyl)-1,3,4-oxadiazol-2-amine,
5-(3-(pyridin-4-yl)methylthiothiophen-2-yl)-N-(3-trifluoromethylphenyl)-1,3,4-oxadiazol-2-amine,
5-(3-(2-acetamidopyridin-4-yl)methylthiothiophen-2-yl)-N-(3-trifluoromethylphenyl)-1,3,4-oxadiazol-2-amine,
5-(3-(quinolin-4-yl)methylthiothiophen-2-yl)-N-(3-trifluoromethylphenyl)-1,3,4-oxadiazol-2-amine,
5-(3-(pyridin-4-yl)methylthiothiophen-2-yl)-N-(3-trifluoromethylphenyl)-1,3,4-thiadiazol-2-amine,
5-(3-(2-acetamidopyridin-4-yl)methylthiothiophen-2-yl)-N-(3-trifluoromethylphenyl)-1,3,4-thiadiazol-2-amine,
N-(4-chlorophenyl)-5-(2-(pyridin-4-yl)methylthiothiophen-3-yl)-1,3,4-oxadiazol-2-amine,
5-(2-(2-acetamidopyridin-4-yl)methylthiothiophen-3-yl)-N-(4-chlorophenyl)-1,3,4-oxadiazol-2-amine,
5-(2-(2-acetamidopyridin-4-yl)methylthiothiophen-3-yl)-N-(3-trifluoromethylphenyl)-1,3,4-oxadiazol-2-amine,
5-(3-(pyridin-4-yl)methylthiothiophen-2-yl)-N-(4-trifluoromethoxylphenyl)-1,3,4-thiadiazol-2-amine, and
5-(3-(2-acetamidopyridin-4-yl)methylthiothiophen-2-yl)-N-(4-trifluoromethoxylphenyl)-1,3,4-thiadiazol-2-amine.

6. A pharmaceutical composition comprising the compound or the salt thereof according to any one of claims 1 to 5 and a pharmaceutically acceptable carrier.

* * * * *